US010278882B2

(12) United States Patent
Nagata et al.

(10) Patent No.: US 10,278,882 B2
(45) Date of Patent: *May 7, 2019

(54) ASSIST WEAR ITEM, CONTROL METHOD FOR CONTROLLER OF ASSIST WEAR ITEM, AND RECORDING MEDIUM

(71) Applicant: Panasonic Intellectual Property Management Co., Ltd., Osaka (JP)

(72) Inventors: Takayuki Nagata, Osaka (JP); Stephen William John, Kyoto (JP); Katsuhiko Asai, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 672 days.

This patent is subject to a terminal disclaimer.

(21) Appl. No.: 15/006,231

(22) Filed: Jan. 26, 2016

(65) Prior Publication Data

US 2016/0242986 A1    Aug. 25, 2016

(30) Foreign Application Priority Data

Feb. 19, 2015   (JP) ................................ 2015-031101

(51) Int. Cl.
*A61H 3/00*   (2006.01)
*A61H 1/02*   (2006.01)
(Continued)

(52) U.S. Cl.
CPC ................. *A61H 3/00* (2013.01); *A61F 2/70* (2013.01); *A61F 2/72* (2013.01); *A61F 5/01* (2013.01);
(Continued)

(58) Field of Classification Search
CPC .......... A61H 1/00; A61H 1/0262; A61H 3/00; A61H 3/008; A61H 3/06; A61F 5/01;
(Continued)

(56) References Cited

U.S. PATENT DOCUMENTS

2003/0125781 A1* 7/2003 Dohno ............. A63B 21/00181
607/75
2007/0265140 A1* 11/2007 Kim ......................... A61H 1/02
482/8

(Continued)

FOREIGN PATENT DOCUMENTS

JP    2002-120183    4/2002
JP    2003-250842    9/2003
(Continued)

*Primary Examiner* — Justine R Yu
*Assistant Examiner* — Zachary E Love
(74) *Attorney, Agent, or Firm* — Wenderoth, Lind & Ponack, L.L.P.

(57) ABSTRACT

An assist wear item is worn on a portion of a living body and has an inner surface brought into contact with the portion. The assist wear item includes assisting actuators, contact sensors, and a controller. Each assisting actuator is driven to expand and contract. The assisting actuators are linearly arranged along an expansion/contraction direction of a muscle at the portion. Each contact sensor detects a contact with an outer surface of the assist wear item. The contact sensors include a first contact sensor and a second contact sensor. The controller increases or decreases a driving power of expansion/contraction driving of an assisting actuator corresponding to a region ranging from the first contact sensor to the second contact sensor if the controller continuously receives a detection result indicating a contact from at least one contact sensor between the first and second contact sensors during a certain time period.

18 Claims, 40 Drawing Sheets

(51) Int. Cl.
*A61F 2/70* (2006.01)
*A61F 2/72* (2006.01)
*A61F 5/01* (2006.01)
*A61F 2/68* (2006.01)
*A61F 2/50* (2006.01)

(52) U.S. Cl.
CPC .... *A61H 1/0262* (2013.01); *A61F 2002/5066* (2013.01); *A61F 2002/6872* (2013.01); *A61F 2002/701* (2013.01); *A61F 2002/704* (2013.01); *A61F 2005/0155* (2013.01)

(58) Field of Classification Search
CPC ...... A61F 2/70; A61F 2/72; A61F 2002/5066; A61F 2002/6872; A61F 2002/701; A61F 2002/704; B25J 9/00; B25J 11/00
USPC ........................................................ 601/5, 34
See application file for complete search history.

(56) References Cited

U.S. PATENT DOCUMENTS

| | | | |
|---|---|---|---|
| 2010/0249675 A1 | 9/2010 | Fujimoto et al. | |
| 2013/0116852 A1* | 5/2013 | Dijk | A61H 23/02 700/301 |
| 2014/0171838 A1* | 6/2014 | Aleksov | A61H 1/0244 601/33 |
| 2014/0288664 A1 | 9/2014 | Miyazawa | |
| 2015/0163621 A1* | 6/2015 | Wang | H04W 4/80 455/41.3 |
| 2015/0257711 A1* | 9/2015 | Chen | A61B 5/7282 601/134 |
| 2016/0058646 A1* | 3/2016 | Seo | A61H 3/00 623/32 |
| 2018/0239469 A1* | 8/2018 | Connor | G06F 3/044 |

FOREIGN PATENT DOCUMENTS

| | | |
|---|---|---|
| JP | 2009-112578 | 5/2009 |
| JP | 2010-176174 | 8/2010 |
| JP | 2013-146328 | 8/2013 |
| JP | 2013-170391 | 9/2013 |
| JP | 2014-184027 | 10/2014 |
| JP | 2015-128520 | 7/2015 |

* cited by examiner

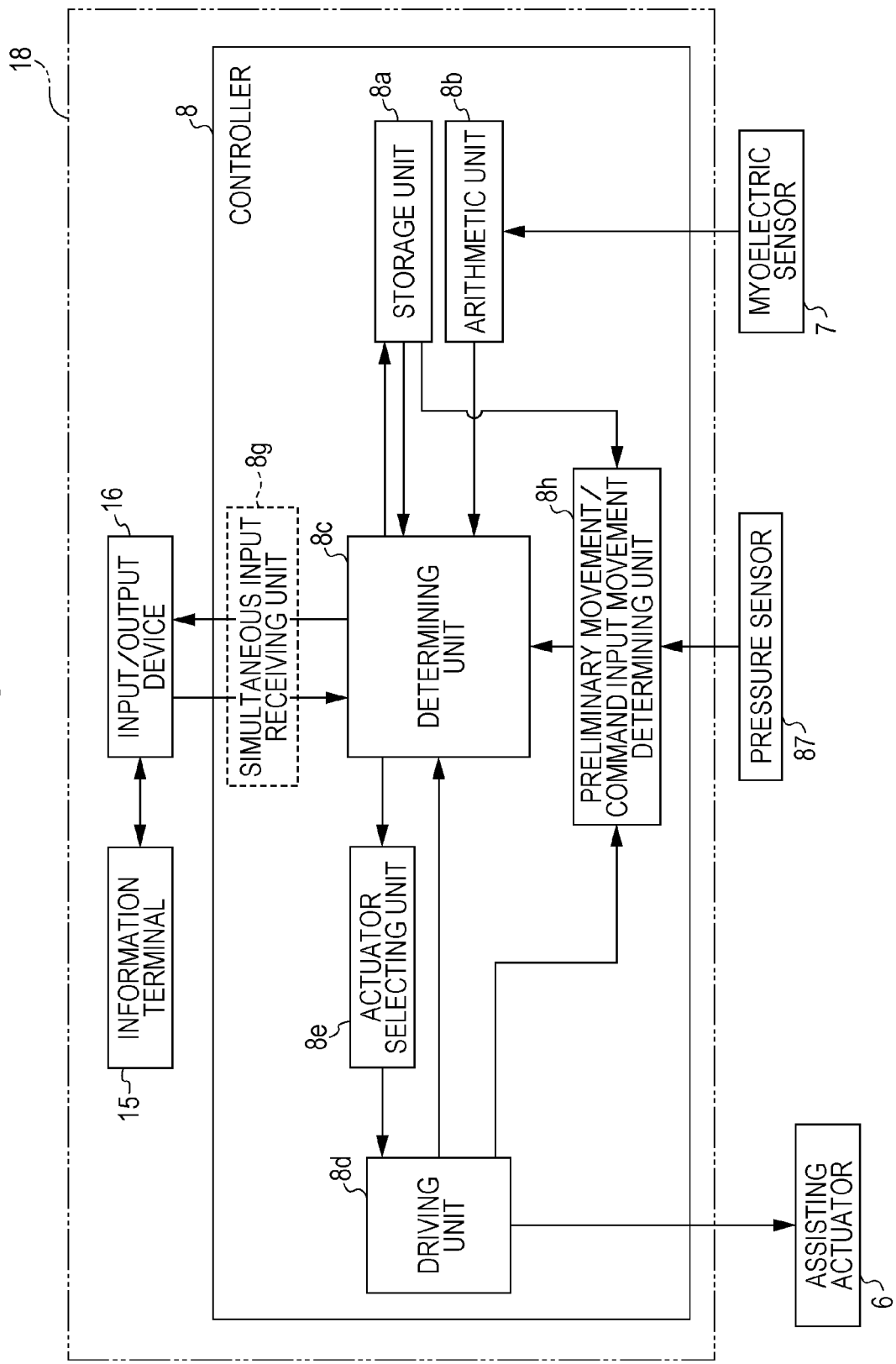

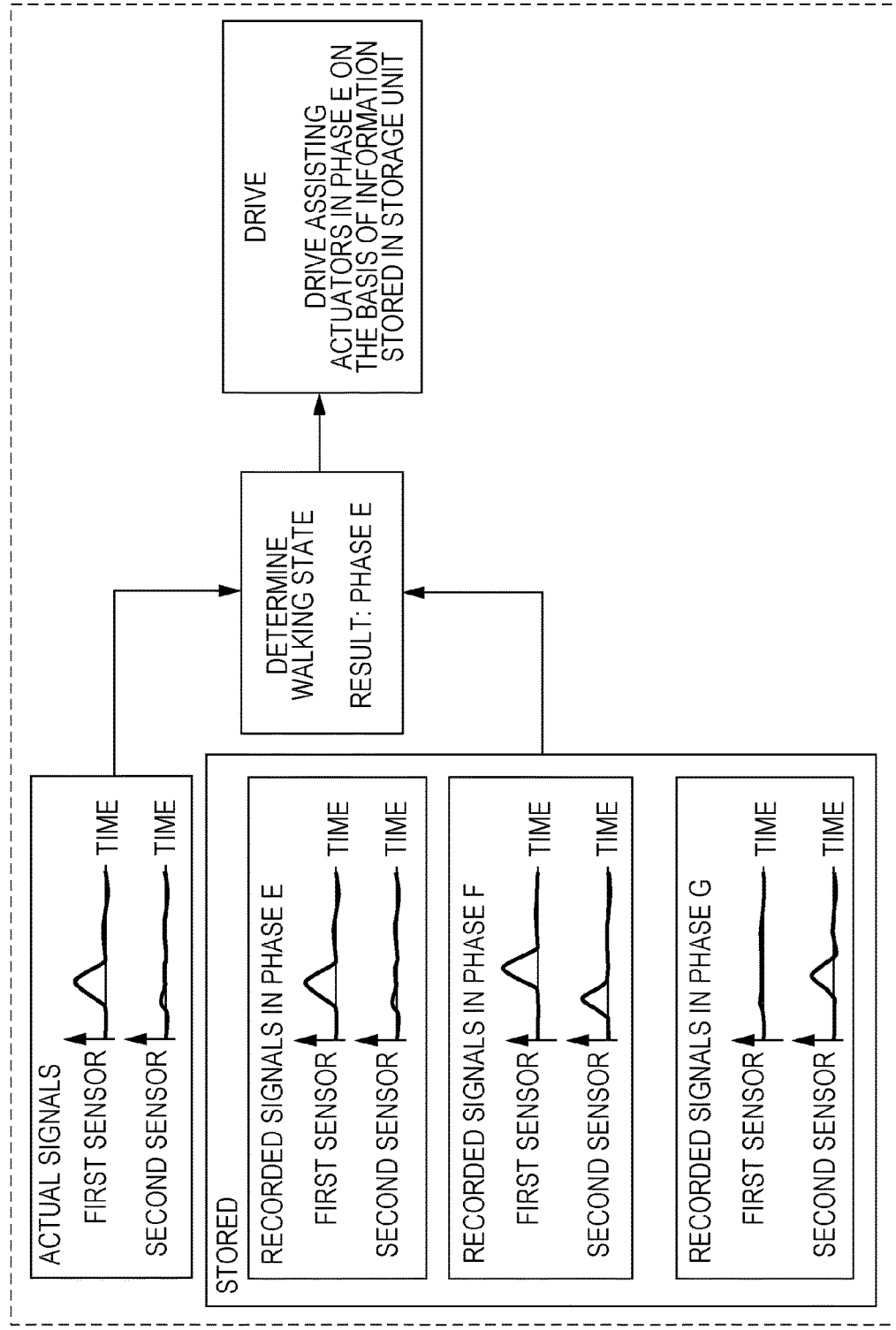

FIG. 4C

| PHASE | TIME PERIOD | FIRST SENSOR | SECOND SENSOR |
|---|---|---|---|
| E | t1 | 1 | 0 |
|  | t2 | 2 | 0 |
|  | t3 | 3 | 0 |
|  | t4 | 2 | 0 |
|  | --- |  |  |

FIG. 4D

| PHASE | TIME PERIOD | ACTUATOR | | | | |
|---|---|---|---|---|---|---|
|  |  | A | B | C | D | E |
| E | t1 | 0 | 0 | 1 | 0 | 0 |
|  | t2 | 0 | 1 | 2 | 1 | 0 |
|  | t3 | 0 | 2 | 3 | 2 | 0 |
|  | t4 | 0 | 1 | 1 | 1 | 0 |
|  | --- |  |  |  |  |  |

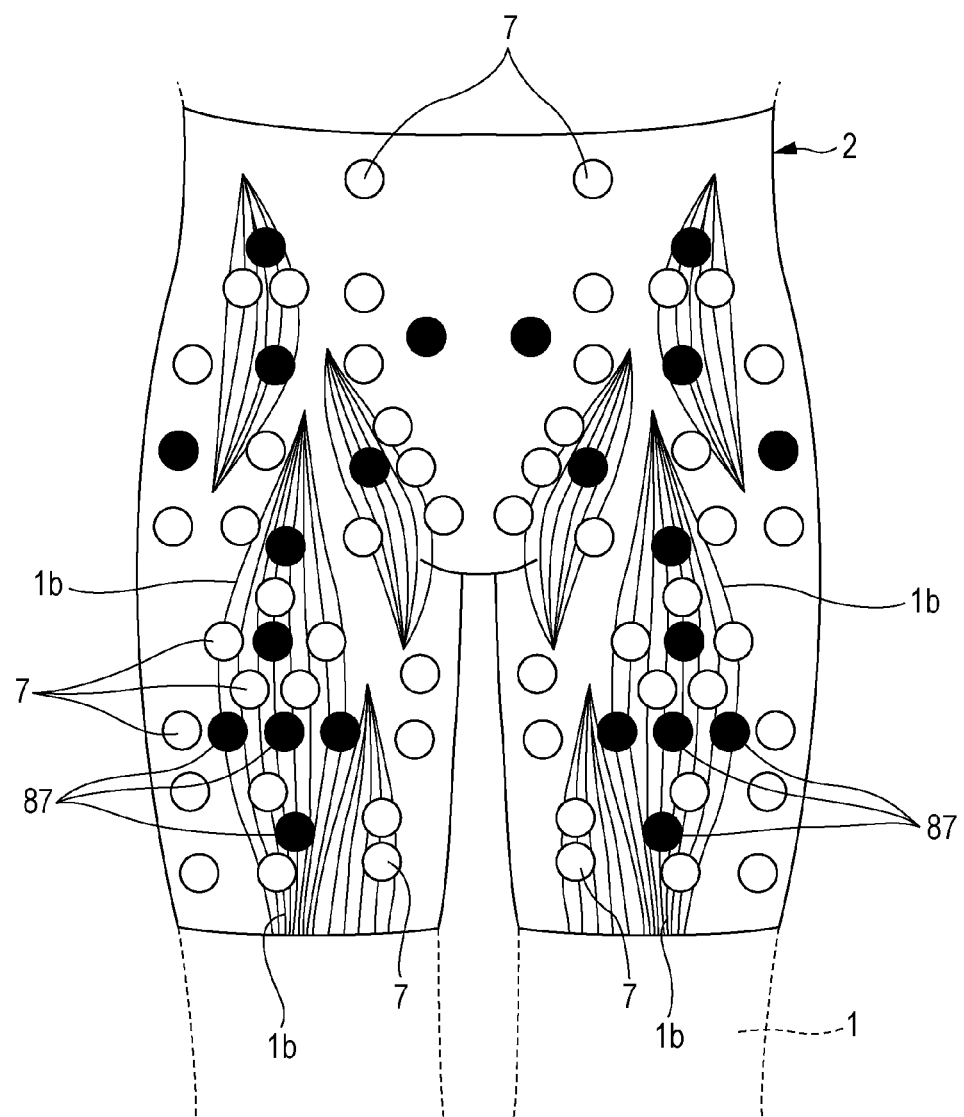

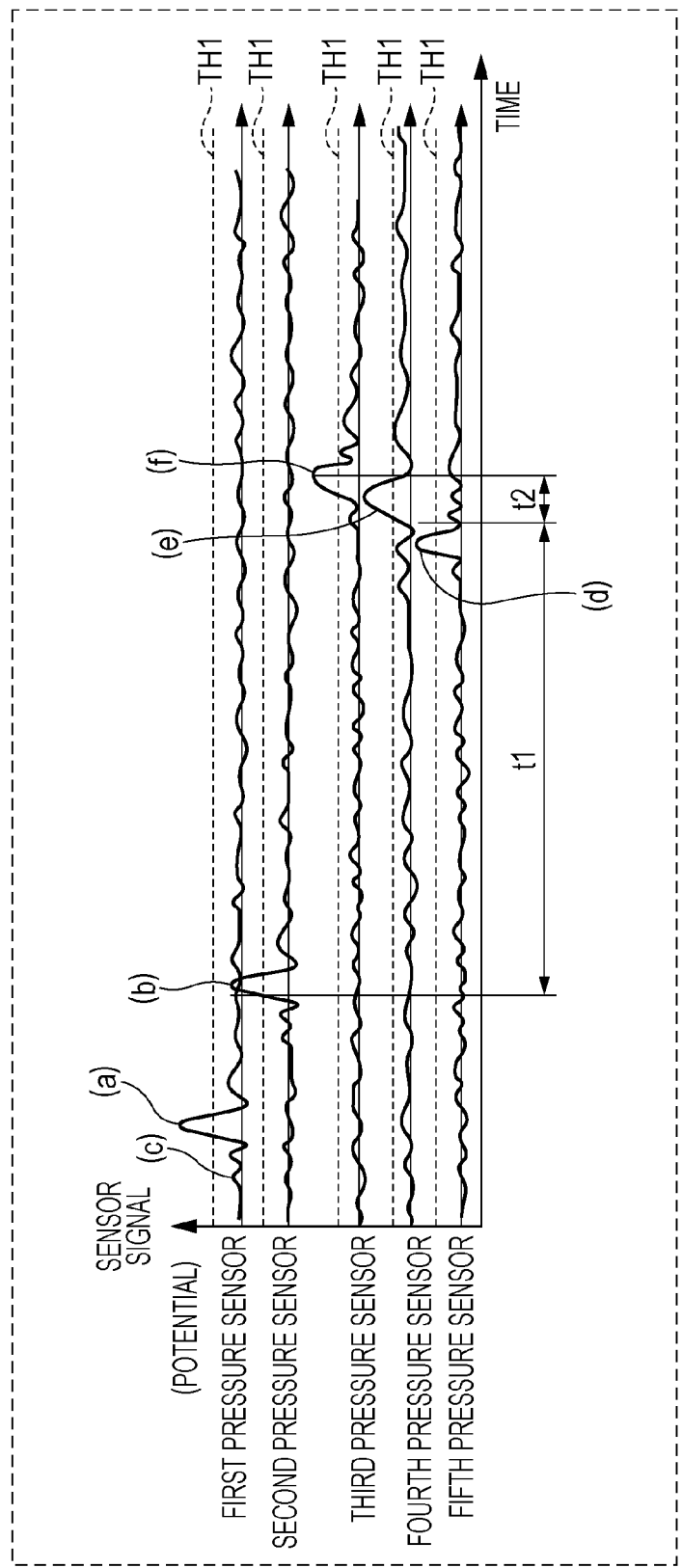

FIG. 34A

| THE NUMBER OF SENSORS DETECTED CONTACT WITHIN SECOND TIME PERIOD | SET VALUE OF ASSIST POWER |
|---|---|
| 1 TO 4 | +10% |
| 5 TO 8 | +20% |
| 9 TO 12 | +30% |
| 13 TO 16 | +40% |
| 17 OR MORE | +50% |

FIG. 34B

| DISTANCE L (cm) BETWEEN FIRST CONTACT SENSOR AND SECOND CONTACT SENSOR | SET VALUE OF ASSIST POWER |
|---|---|
| $0 < L \leq 4$ | +10% |
| $4 < L \leq 8$ | +20% |
| $8 < L \leq 12$ | +30% |
| $12 < L \leq 16$ | +40% |
| $16 < L$ | +50% |

| AMOUNT OF CHANGE IN EXPANSION/CONTRACTION LENGTH | FIRST THRESHOLD |
|---|---|
| 0 TO 10% | A |
| 10 TO 30% | 1.5A |
| 30 TO 50% | 2.0A |
| 50% OR MORE | 3.0A |

ASSIST WEAR ITEM, CONTROL METHOD FOR CONTROLLER OF ASSIST WEAR ITEM, AND RECORDING MEDIUM

BACKGROUND

1. Technical Field

The present disclosure relates to an assist wear item, a control method for a controller of an assist wear item, and a recording medium that are capable of easily adjusting assist power when the assist wear item is worn on a living body and movements of the living body are assisted by supporting generation power of the living body by using the assist power.

2. Description of the Related Art

There is a human body movement assisting apparatus capable of assisting movements in daily life, in which an attachment made of meshed cloth or the like is attached to a joint portion such as a knee of a human body and generation power of the human body is supported by driving an actuator provided on the attachment (see, for example, Japanese Unexamined Patent Application Publication No. 2003-250842).

SUMMARY

However, the related art requires further improvements to easily adjust an increase or decrease in the driving power of expansion/contraction driving of assisting actuators of an assist wear item.

One non-limiting and exemplary embodiment provides an assist wear item capable of easily adjusting an increase or decrease in the driving power of expansion/contraction driving of assisting actuators in the case of assisting movements of a living body.

In one general aspect, the techniques disclosed here feature an assist wear item that is worn on a portion of a living body and that has an inner surface which is brought into contact with the portion. The assist wear item includes a plurality of assisting actuators each of which is driven to expand and contract, the plurality of assisting actuators being linearly arranged along an expansion/contraction direction of a muscle at the portion in a case where the assist wear item is worn on the portion; a plurality of contact sensors each of which detects a contact with an outer surface of the assist wear item, the plurality of contact sensors including a first contact sensor and a second contact sensor that is arranged at a certain distance or more from the first contact sensor; and a controller that increases or decreases a driving power of expansion/contraction driving of an assisting actuator corresponding to a region ranging from the first contact sensor to the second contact sensor among the plurality of assisting actuators if the controller continuously receives a detection result indicating a contact from at least one contact sensor arranged between the first contact sensor and the second contact sensor during an entire time period after the controller receives a detection result indicating a first contact from the first contact sensor until the controller receives a detection result indicating a second contact from the second contact sensor. If the controller receives a detection result indicating a contact with the outer surface of the assist wear item from the first contact sensor during expansion/contraction driving of the assisting actuator, the controller determines that the contact with the outer surface of the assist wear item is the first contact.

According to an embodiment of the present disclosure, an increase or decrease in the driving power of expansion/contraction driving of assisting actuators can be easily adjusted in the case of assisting movements of a living body.

It should be noted that general or specific embodiments may be implemented as a system, a method, an integrated circuit, a computer program, a computer-readable recording medium, or any selective combination thereof. The computer-readable recording medium includes a nonvolatile recording medium, for example, a compact disc-read only memory (CD-ROM) or the like.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4A is a block diagram related to the assist wear item;

FIG. 4B is an explanatory diagram for describing comparison and determination;

FIG. 4C is an explanatory diagram of signals in a certain phase in a time response pattern used for the determination in FIG. 4B;

FIG. 4D is an explanatory diagram of an example of driving assisting actuators in a certain phase based on the determination in FIG. 4B;

FIG. 6 is an explanatory diagram illustrating a relationship between muscles and an arrangement state of sensors on the front side of the wear main body;

FIG. 27 is a graph for describing an example of a relationship among sensor signals which are outputs from five pressure sensors, a first threshold, and a first time period;

FIG. 34A is a diagram illustrating, in the form of a table, a relationship between the numbers of pressure sensors and set values of assist power;

FIG. 34B is a diagram illustrating, in the form of a table, a relationship between maximum distances between pressure sensors and set values of assist power;

DETAILED DESCRIPTION

Figure 1:
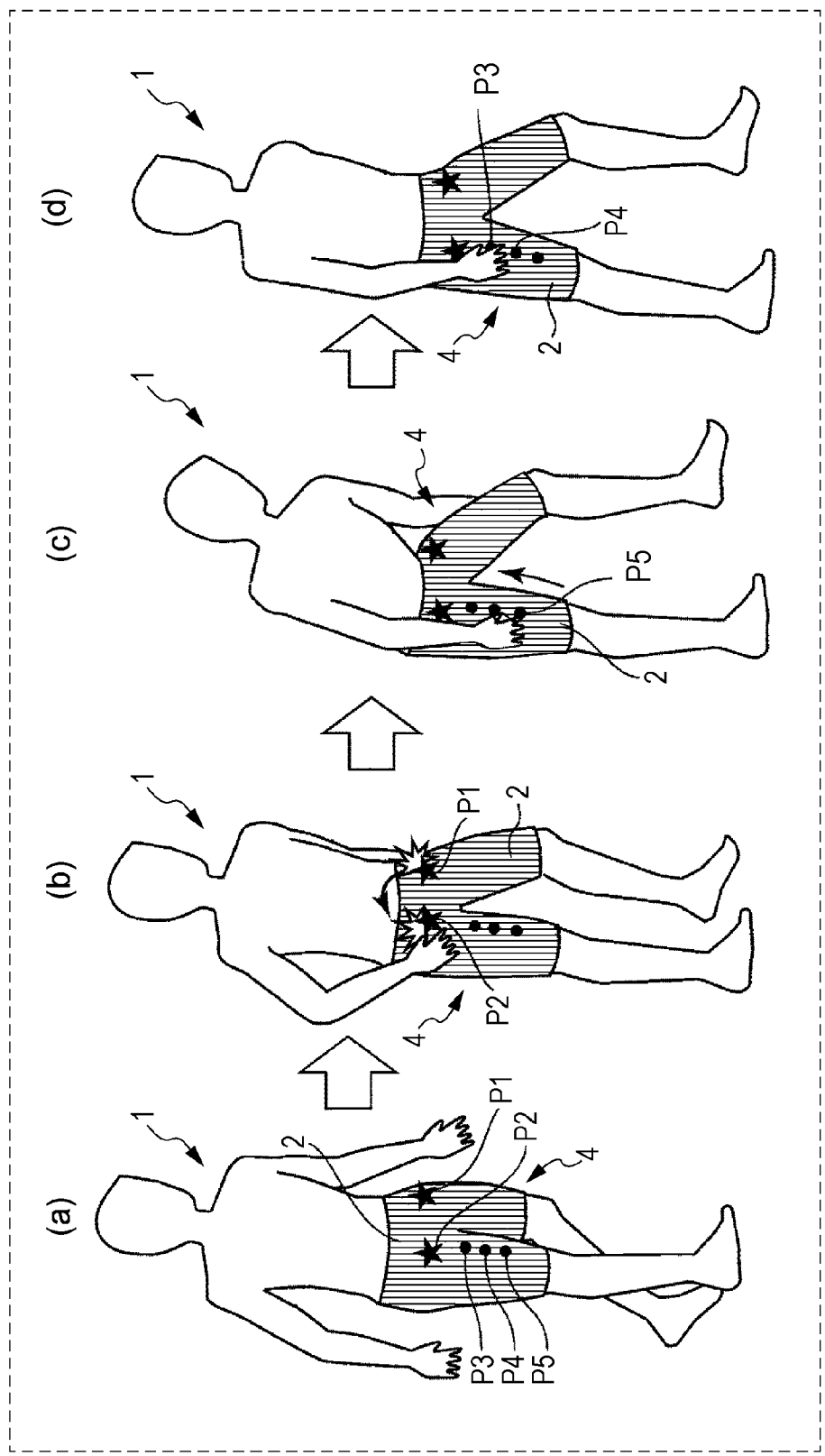
FIG. 1 is a schematic explanatory diagram illustrating movements of a user in a state where the user is wearing an assist wear item according to an embodiment of the present disclosure.

Hereinafter, an embodiment of the present disclosure will be described in detail with reference to the attached drawings. Before describing the embodiment of the present disclosure, various aspects of the present disclosure will be described.

An assist wear item according to an aspect of the present disclosure is an assist wear item that is worn on a portion of a living body and that has an inner surface which is brought into contact with the portion, including:

a plurality of assisting actuators each of which is driven to expand and contract, the plurality of assisting actuators being linearly arranged along an expansion/contraction direction of a muscle at the portion in a case where the assist wear item is worn on the portion;

a plurality of contact sensors each of which detects a contact with an outer surface of the assist wear item, the plurality of contact sensors including a first contact sensor and a second contact sensor that is arranged at a certain distance or more from the first contact sensor; and a controller that increases or decreases a driving power of expansion/contraction driving of an assisting actuator corresponding to a region ranging from the first contact sensor to the second contact sensor among the plurality of assisting actuators if the controller continuously receives a detection result indicating a contact from at least one contact sensor arranged between the first contact sensor and the second contact sensor during an entire time period after the controller receives a detection result indicating a first contact from the first contact sensor until the controller receives a detection result indicating a second contact from the second contact sensor.

If a dedicated terminal (an information terminal, an input/output device, or the like), is used to increase or decrease the driving power of expansion/contraction driving of assisting actuators, it is necessary to specify the part where the driving power is to be increased or decreased and input an amount of increase or decrease in the driving power every time the driving power is to be increased or decreased, which is inconvenient.

According to the above-described aspect, a driving power of expansion/contraction driving of an assisting actuator corresponding to a region ranging from the first contact sensor to the second contact sensor among the plurality of assisting actuators is increased or decreased if the controller continuously receives a detection result indicating a contact from at least one contact sensor arranged between the first contact sensor and the second contact sensor during an entire time period after the controller receives a detection result indicating a first contact from the first contact sensor until the controller receives a detection result indicating a second contact from the second contact sensor.

Accordingly, a user, which is an example of a living body that wears the assist wear item, is able to increase or decrease the driving power of expansion/contraction driving of the assisting actuators only by swiping the assist wear item at the portion where the driving power is to be increased or decreased, that is, without using the dedicated terminal.

In the above-described aspect, if the controller receives a detection result indicating a contact with the outer surface of the assist wear item from the first contact sensor during expansion/contraction driving of the assisting actuator, the controller may determine that the contact with the outer surface of the assist wear item is the first contact.

In many cases, when the user wants to increase or decrease the driving power of expansion/contraction driving of the assisting actuators, the user wants to fine-tune assist power when the user is wearing the assist wear item and performing movements while receiving the assist power (the driving power of expansion/contraction driving the assisting actuators) from the assist wear item. In other words, when the user is not receiving assist power from the assist wear item, it is rare that the user wants to fine-tune the assist power, that is, wants to increase or decrease the driving power of expansion/contraction driving of the assisting actuators.

According to the above-described aspect, if the controller receives a detection result indicating a contact with the outer surface of the assist wear item from the first contact sensor during expansion/contraction driving of the assisting actuator, the controller determines that the contact with the outer surface of the assist wear item is the first contact. Thus, a detection result indicating the first contact is received in a situation where the user wants to fine-tune the assist power, that is, while the user is receiving the assist power from the assist wear item. As a result, in a situation where the user is less likely to want to increase or decrease the driving power of expansion/contraction driving of the assisting actuators, determination of reception of a detection result indicating the first contact is prevented from being made, and accordingly an increase or decrease in the driving power not intended by the user can be prevented.

In the above-described aspect, if the controller receives a detection result indicating a contact with the outer surface of the assist wear item from the first contact sensor within a first time period after the controller receives a detection result indicating a third contact from a third contact sensor among the plurality of contact sensors, the controller may determine that the contact with the outer surface of the assist wear item is the first contact.

Since the assist wear item is worn by the user who performs movements, the outer surface of the assist wear item often receives a contact. For example, it is possible that the user's hand accidentally touches the assist wear item during movements. In such a case, if the driving power is increased or decreased every time the assist wear item receives a contact, an increase or decrease in the driving power not intended by the user may occur.

According to the above-described aspect, if the controller receives a detection result indicating a contact with the outer surface of the assist wear item from the first contact sensor within a first time period after the controller receives a detection result indicating a third contact from a third contact sensor, the controller determines that the contact with the outer surface of the assist wear item is the first contact. This is because, if the user unintendedly touches the assist wear item, there is a low probability that a first contact as the next contact will be detected within a short time period from the third contact after the unintended third contact. On the other hand, if the user intendedly touches the assist wear item, that is, if the user wants to increase or decrease the driving power, it is estimated that the third contact and the first contact following the third contact will be detected within a short time period. On the basis of this, with detection of a first contact by the first contact sensor being performed within the first time period after detection of the third contact, an increase or decrease in the driving power of the assisting actuators not intended by the user can be prevented.

Further, in a case where some contacts with the assist wear item not intended by the user are sequentially detected, the contacts are likely to occur at the same position. Thus, a case where the third contact and the first contact are detected by the same contact sensor is often a case where the contacts are not intended by the user. According to the above-described aspect, the third contact is detected by the third contact sensor, and the first contact is detected by the first contact sensor. That is, the user needs to first touch a portion different from a portion where the driving power is to be increased or decreased, and accordingly an increase or decrease in the driving power not intended by the user can be effectively prevented.

In the above-described aspect, the third contact sensor may be identical to the first contact sensor.

In general, a user who performs an input operation for increasing or decreasing the driving power of expansion/contraction driving of the assisting actuators without using the terminal wants to specify the portion of the assist wear item for which the driving power is to be increased or decreased and then wants to input the amount of increase or decrease in the driving power.

According to the above-described aspect, a third contact and a first contact are detected by the same contact sensor. Thus, if the user touches a certain position, and within the first time period after that, if the user performs a swipe movement starting from the certain position, the driving power at the swipe position is increased or decreased. As a result, the user is able to perform an intuitive operation of touching a portion for which the driving power is to be increased or decreased and then performing a swipe movement in accordance with the amount of increase or decrease.

In the above-described aspect, the controller may increase the driving power of the expansion/contraction driving of the corresponding assisting actuator as the distance between the first contact sensor and the second contact sensor increases.

According to the above-described aspect, when the user wants to increase the deriving power, the user only has to swipe the assist wear item until a desired driving power is obtained, and thus the user is able to perform a more intuitive input operation.

In the above-described aspect, if the controller receives a detection result indicating a contact with the outer surface of the assist wear item from the first contact sensor during expansion driving of the corresponding assisting actuator, the controller may increase a driving power of the expansion driving of the corresponding assisting actuator.

In the above-described aspect, if the controller receives a detection result indicating a contact with the outer surface of the assist wear item from the first contact sensor during contraction driving of the corresponding assisting actuator, the controller may increase a driving power of the contraction driving of the corresponding assisting actuator.

In the above-described aspect, an increase or decrease in the driving power of the expansion/contraction driving of the corresponding assisting actuator may be controlled by changing an expansion/contraction length of the corresponding assisting actuator.

In the above-described aspect, an increase or decrease in the driving power of the expansion/contraction driving of the corresponding assisting actuator may be controlled by changing a spring constant of the corresponding assisting actuator.

In the above-described aspect, the plurality of contact sensors may be a plurality of pressure sensors each of which detects a pressure value of a pressure applied to the outer surface of the assist wear item, and If the controller receives a detection result indicating a pressure value which is a first threshold or larger from each of the plurality of pressure sensors, the controller may determine that there has been a contact with the outer surface of the assist wear item.

According to the above-described aspect, the plurality of pressure sensors are used as the plurality of contact sensors. Here, when the user wants to increase or decrease the driving power of expansion/contraction driving of the assisting actuators, the user is likely to touch the assist wear item more strongly than in the case of accidentally touching it. Thus, for example, if the first threshold is set to a value equal to or larger than a pressure value that is detected when the user accidentally touches the assist wear item, an increase or decrease in the driving power can be prevented when the user accidentally touches the assist wear item.

In the above-described aspect, the assist wear item may further include a plurality of myoelectric sensors each of which detects a voltage value of a voltage generated when the muscle at the portion is moved, the plurality of myoelectric sensors being arranged at positions where the plurality of assisting actuators are arranged or around the positions, and the controller may cause the plurality of assisting actuators to be driven to expand and contract in accordance with the individual voltage values detected by the plurality of myoelectric sensors.

A voltage detected by the myoelectric sensor is a voltage that is generated immediately before the muscle is moved, and is not a voltage that is generated after the muscle is moved. Thus, according to the above-described aspect, driving of the assisting actuators can be controlled on the basis of a detection result indicating a voltage that is generated immediately before the muscle is moved. As a result, trackability of assist by the assisting actuators is increased.

In the above-described aspect, if an amount of change in the voltage value per unit time detected by a first myoelectric sensor among the plurality of myoelectric sensors is equal to or larger than a second threshold, the controller may increase a first threshold that is used by a pressure sensor corresponding to the first myoelectric sensor to detect a pressure value.

A pressure value that is detected by the pressure sensor when the user is moving hard is considered to be larger than a pressure value that is detected by the pressure sensor when the user is not moving hard. For example, a pressure value that is detected when the user is running and a hand of the user accidentally touches the assist wear item is estimated to be larger than a pressure value that is detected when the user is walking and a hand of the user accidentally touches the assist wear item. In this case, if the first threshold is a fixed value, it may be determined or not determined that there has been a touch with the outer surface of the assist wear item depending on the degree of movements of the user.

According to the above-described aspect, when an amount of change in the voltage value per unit time detected by the first myoelectric sensor among the plurality of myoelectric sensors is the second threshold or larger, that is, when the user is moving hard, the first threshold used by the pressure sensor corresponding to the first myoelectric sensor to detect a pressure value is increased. Accordingly, even when the user is moving hard, an increase or decrease in the driving power of expansion/contraction driving of the assisting actuators not intended by the user can be effectively prevented.

In the above-described aspect, the plurality of contact sensors may be a plurality of touch sensors each of which detects an amount of change in capacitance, the plurality of touch sensors being arranged on the outer surface of the assist wear item, and If the controller receives a detection result indicating an amount of change in capacitance that is equal to or larger than a third threshold from each of the plurality of touch sensors, the controller may determine that there has been a contact with the outer surface of the assist wear item.

According to the above-described aspect, the plurality of touch sensors are used as the plurality of contact sensors. Here, when the user wants to increase or decrease the driving power of expansion/contraction driving of the assisting actuators, the user is likely to touch the assist wear item more strongly than in the case of accidentally touching it. Thus, for example, if the third threshold is set to a value equal to or larger than an amount of change in capacitance that is detected when the user accidentally touches the assist wear item, an increase or decrease in the driving power can be prevented when the user accidentally touches the assist wear item.

In the above-described aspect, the assist wear item may include a pair of attachments that are respectively worn on two symmetrical portions of the living body, each of a plurality of assisting actuators arranged on a first attachment in the pair of attachments may be associated with a corresponding one of a plurality of assisting actuators arranged on a second attachment in the pair of attachments, and if a driving power of expansion/contraction driving of a first assisting actuator arranged on the first attachment is increased or decreased, the controller may increase or decrease, in conjunction with the increase or decrease in the first assisting actuator, a driving power of expansion/contraction driving of a second assisting actuator arranged on the second attachment and corresponding to the first assisting actuator.

According to the above-described aspect, in a case where assist pants worn on the individual legs are used as the assist wear item, for example, if the driving power for one of the legs is increased or decreased, the driving power for the other leg is also increased or decreased. Accordingly, if an input operation is performed for one of the legs, an input operation for the other leg can be performed at the same time, and thus an input operation can be performed more easily.

A control method for a controller of an assist wear item according to another aspect of the present disclosure is a control method for a controller of an assist wear item that is worn on a portion of a living body and that has an inner surface which is brought into contact with the portion, the assist wear item including a plurality of assisting actuators each of which is driven to expand and contract, the plurality of assisting actuators being linearly arranged along an expansion/contraction direction of a muscle at the portion in a case where the assist wear item is worn on the portion, a plurality of contact sensors each of which detects a contact with an outer surface of the assist wear item, and the controller, the control method including:

receiving a detection result indicating a first contact from a first contact sensor among the plurality of contact sensors;

if a detection result indicating a contact is continuously received from a contact sensor arranged between the first contact sensor and a second contact sensor that is arranged at a certain distance or more from the first contact sensor during a time period after the receiving until a detection result indicating a second contact is received from the second contact sensor, increasing or decreasing a driving power of expansion/contraction driving of an assisting actuator corresponding to a region ranging from the first contact sensor to the second contact sensor among the plurality of assisting actuators; and if a detection result indicating a contact with the outer surface of the assist wear item is received from the first contact sensor during expansion/contraction driving of the assisting actuator, determining that the contact with the outer surface of the assist wear item is the first contact.

A recording medium according to another aspect of the present disclosure is a recording medium storing a program that causes a device including a processor to perform processing executed by a controller of an assist wear item that is worn on a portion of a living body and that has an inner surface which is brought into contact with the portion, the recording medium being nonvolatile and computer-readable, the assist wear item including a plurality of assisting actuators each of which is driven to expand and contract, the plurality of assisting actuators being linearly arranged along an expansion/contraction direction of a muscle at the portion in a case where the assist wear item is worn on the portion, a plurality of contact sensors each of which detects a contact with an outer surface of the assist wear item, and the controller, the processing including:

receiving a detection result indicating a first contact from a first contact sensor among the plurality of contact sensors;

if a detection result indicating a contact is continuously received from a contact sensor arranged between the first contact sensor and a second contact sensor that is arranged at a certain distance or more from the first contact sensor during a time period after the receiving until a detection result indicating a second contact is received from the second contact sensor, increasing or decreasing a driving power of expansion/contraction driving of an assisting actuator corresponding to a region ranging from the first contact sensor to the second contact sensor among the plurality of assisting actuators; and if a detection result indicating a contact with the outer surface of the assist wear item is received from the first contact sensor during expansion/contraction driving of the assisting actuator, determining that the contact with the outer surface of the assist wear item is the first contact.

The assist wear item may further include a sensor that detects a posture of the portion of the living body, the first contact sensor may be selected in accordance with the posture detected by the sensor, and detection of the first contact may be performed based on an output from the selected first contact sensor.

The assist wear item may further include a myoelectric sensor, the posture of the portion of the living body may be detected based on a waveform of a voltage detected by the myoelectric sensor, and the plurality of assisting actuators may be caused to periodically expand and contract.

An assist wear item according to another aspect of the present disclosure includes:

a first sensor that detects a first contact with the assist wear item and outputs a first signal;

a second sensor that detects a second contact with the assist wear item and outputs a second signal;

a third sensor that detects a third contact with the assist wear item and outputs a third signal;

an actuator that changes a degree of contraction in response to a control signal including information indicating the degree of contraction; and a controller that receives the first signal, the second signal, and the third signal, and outputs the control signal, the controller generating the control signal if the controller receives the first signal after the controller receives an instruction to start driving the actuator, the controller receives the second signal after the controller receives the first signal, and the controller receives the third signal after the controller receives the second signal, wherein the controller determines the information in a manner that the degree of contraction increases as a sum of a first distance between the first sensor and the second sensor and a second distance between the second sensor and the third sensor increases.

Embodiment

Hereinafter, an embodiment of the present disclosure will be described in detail with reference to the drawings.

Schematic Configuration and User Movements

Figure 2:
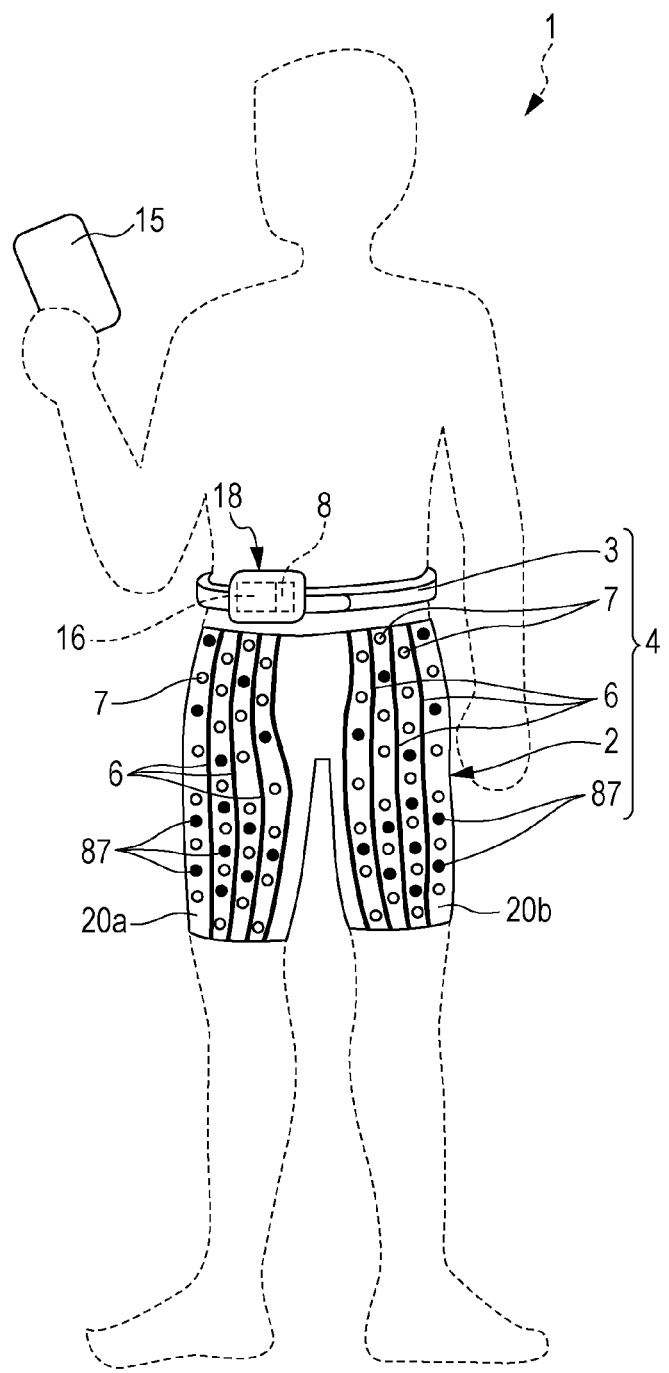
FIG. 2 is an explanatory diagram illustrating a state where the user is wearing the assist wear item according to the embodiment of the present disclosure.
Figure 3:
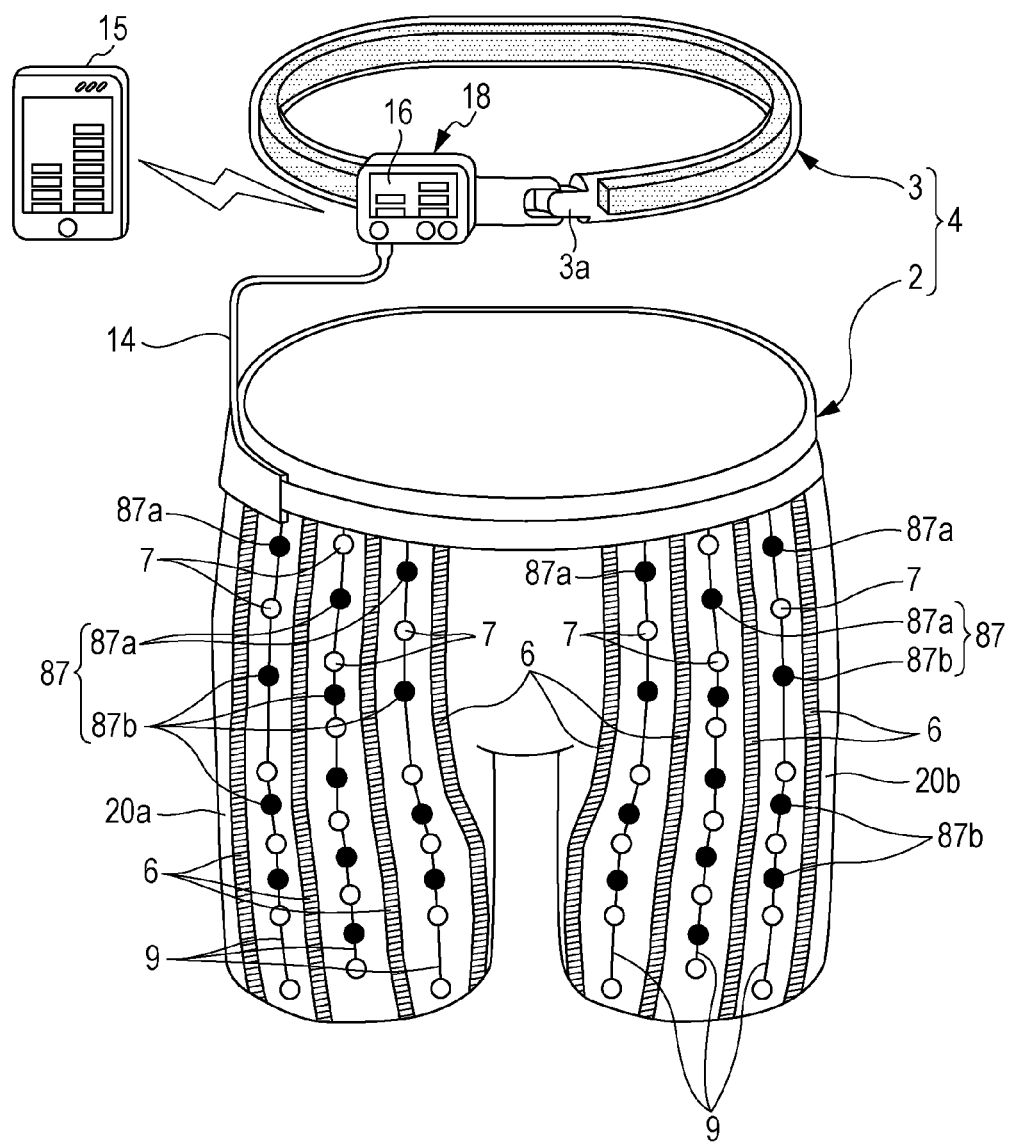
FIG. 3 is a perspective view of the assist wear item illustrated in FIG. 2.

FIG. 1 is a schematic explanatory diagram illustrating movements of a user 1, which is an example of a living body, in a state where the user 1 is wearing an assist wear item 4 according to the embodiment of the present disclosure. FIG. 2 is an explanatory diagram illustrating a state where the user 1 (living body) is wearing the assist wear item 4 according to the embodiment of the present disclosure, and FIG. 3 is a perspective view of the assist wear item 4 illustrated in FIG. 2. The assist wear item 4 is worn on a portion to be assisted and assists movements of muscles. The assist wear item 4 includes, in a wear main body 2, at least a plurality of linear assisting actuators 6, a plurality of pressure sensors 87, and a controller 8.

In the embodiment, a description will be given of, as an example, an assist wear item for assisting walking, in which the wear main body 2 is formed of pants. Note that the wear main body 2 is not limited to pants and may be a jacket, an elbow supporter, or a knee supporter according to an assist function.

In the embodiment, as illustrated in FIG. 2, the user 1 uses the assist wear item 4 by wearing a controller belt 3 including the controller 8 on the waist and wearing the wear main body 2. As illustrated in FIG. 3, the wear main body 2 is provided with many myoelectric sensors 7 and pressure sensors 87 and many linear assisting actuators 6 that are fixed on both front and back sides of the wear main body 2 with certain intervals in a vertical direction of the pants, in other words, in a body axis direction of the user 1 (upward/downward direction in FIG. 3). That is, wiring lines 9 to which the many myoelectric sensors 7 and pressure sensors 87 are connected and the assisting actuators 6 are alternately arranged.

The controller 8 includes a preliminary movement/command input movement determining unit 8h that determines whether each of signals detected by the pressure sensors 87 corresponds to a preliminary movement or a command input movement. Here, a command is an assist power adjustment command and a preliminary movement is a movement performed immediately before input of a command in order to avoid incorrect input of a command. The preliminary movement is not always necessary. However, in the case of a system in which a preliminary movement is performed, each pressure sensor 87 may include a pressure sensor 87a for detecting a preliminary movement and a pressure sensor 87b for detecting a command input movement as illustrated in FIG. 3, and the pressure sensors 87a and 87b may be arranged in different regions so as to avoid incorrect input. In the embodiment, a description will be given of movements by using this configuration as an example.

The plurality of pressure sensors 87 illustrated in FIG. 3 correspond to an example of contact sensors, and may be capacitive touch sensors.

Next, a description will be given of, with reference to FIG. 1, movements performed by the user 1 in the case of adjusting an assist power (a driving power of expansion/contraction driving of the assisting actuators 6) in the assist wear item 4 according to the embodiment of the present disclosure.

First, as illustrated in part (a) of FIG. 1, the user 1 puts on the assist wear item 4, activates a walking assist function, and starts walking. Subsequently, as illustrated in part (b) of FIG. 1, the user 1 performs a preliminary movement (reception operation), for example, taps two portions of the wear main body 2 (for example, positions P1 and P2 near the waist in part (b) of FIG. 1) during an assist operation. Within a few seconds after the preliminary movement, as illustrated in part (c) of FIG. 1, the user 1 swipes a portion near the assisting actuators 6 for which the assist power (the driving power of expansion/contraction driving of the assisting actuators 6, which will be described below) is to be controlled (for example, a front portion of the right thigh in part (c) of FIG. 1), from a lower position P5 via an intermediate position P4 to an upper position P3. Here, to swipe means to move a hand of the user 1 in any direction with the hand being in contact with the wear main body 2. This movement corresponds to a command input movement (assist power adjustment operation). In a case where a pressure sensor 87 detects a contact at a position where the user 1 touches the wear main body 2 and a pressure value obtained by the pressure sensor 87 at the time is initially a first threshold TH1 or larger, the contact is determined to be a first contact. After the first contact has been detected, in a case where the pressure sensor 87 detects a contact immediately before the hand of the user 1 moves away from the wear main body 2 and a pressure value obtained by the pressure sensor 87 at the time is the first threshold TH1 or larger, the contact is determined to be a second contact. The trail from the position of the first contact to the position of the second contact is not specified, for example, it may be linear (up and down, slanting, or lateral direction), arc-shaped, or bended. Although a control method will be described below, the controller 8 determines an assist power adjustment command in accordance with the above-described simple preliminary movement and command input movement, and an assist operation for desired movements is performed with the assist power being adjusted on the basis of the command, as illustrated in part (d) of FIG. 1.

The method according to the embodiment is advantageous in that an assist power can be set by directly swiping a target portion, which is intuitive and simple compared to a method for adjusting an assist power by using an information terminal or an input/output device, and thus the method can be used even during movements (during assist operation).

Such a method is simple but has an issue that an incorrect input is likely to occur. In the embodiment, detection of a preliminary movement and a command input movement is performed only during an assist operation, and a signal detected within a few seconds after the detection of the preliminary movement is determined to be a command input, so as to prevent an incorrect input. Further, the preliminary movement and the command input movement, which are sequentially performed, are distinguished from each other more reliably by making a place for detecting the preliminary movement different from a place for detecting the command input movement and by forming the preliminary movement by a plurality of touch movements and forming the command input movement by a swipe movement. The preliminary movement formed of a plurality of touch movements will be described below. If the plurality of touch movements are formed of, for example, touches in certain rhythm, touches at a plurality of positions in specific order, simultaneous touches at a plurality of positions, or a combination of the touches and a specific movement, an incorrect input can be reliably prevented. In a case where the preliminary movement is performed in this manner, it is not always necessary to make the place for detecting the preliminary movement different from the place for detecting the command input movement.

Hereinafter, individual components will be described in detail.

Arrangement of Assisting Actuators

The plurality of assisting actuators 6 are linearly arranged on the wear main body 2 along an expansion/contraction direction of a muscle at a target portion to be assisted of the user 1 in a case where the user 1 is wearing the wear main body 2, and are driven to expand and contract to assist movements of muscles near the assisting actuators 6. The expansion/contraction direction of a muscle is, for example, a direction from one end portion toward the other end portion of the wear main body 2. An end portion of the wear main body 2 is, in a case where the assist wear item 4 corresponds to pants, a waist portion (upper end portion) or a lower end portion. In a case where the assist wear item 4 corresponds to a tube-like member to be worn around an arm, the end portion of the wear main body 2 is a wrist portion or an end portion on the base side of the arm. In a case where the assist wear item 4 corresponds to a tube-like member to be worn around a trunk, the end portion of the wear main body 2 is an upper or lower end portion. In a case where the assist wear item 4 corresponds to a tube-like member to be worn on a hand, the end portion of the wear main body 2 is a tip of a finger portion or an end portion of the base. That is, in a case where the assist wear item 4 is formed as a tube-like member to be worn around a portion of a human body, the end portion of the wear main body 2 is any end portion in the center axis direction thereof.

Arrangement of Pressure Sensors

The plurality of pressure sensors 87 are arranged on the wear main body 2 so as to detect a contact with the outer surface of the wear main body 2, for example. In other words, the pressure sensors 87 are a plurality of pressure sensors that detect a pressure value of a pressure applied on the outer surface and are arranged on the wear main body 2 with regular or random intervals. The pressure sensors 87 are arranged at the positions where the assisting actuators 6 are arranged or around the positions. The pressure sensors 87 detect a contact (a touch and a swipe movement), having a pressure value which is the first threshold TH1 or larger, with the outer surface of the wear main body 2, and outputs a detection result to the controller 8 (the preliminary movement/command input movement determining unit 8h or a receiving unit 8f in a third modification example described below). That is, the pressure sensors 87 are used to detect a preliminary movement for adjusting the assist power of the assisting actuators 6 and a command input movement performed after the preliminary movement and to determine a command. Some of the pressure sensors 87, which are touched to input a command, are associated with the respective assisting actuators 6. For example, an assisting actuator 6 and the pressure sensors 87 that are arranged near the assisting actuator 6 (for example, within 10 mm) are associated with each other, and information representing the correspondence is stored in a storage unit 8a, which will be described below. Thus, the controller 8 (a command determination controller 88 in the third modification example) controls, on the basis of a swipe movement in which a first contact, a second contact, and an intermediate contact therebetween are detected by at least one of the pressure sensors 87 associated with the assisting actuator 6, an increase or decrease in the driving power of expansion/contraction driving of the assisting actuator 6 corresponding to the at least one pressure sensor 87 related to the detection of contacts. Note that the pressure sensor 87a that is used only for a preliminary movement is not necessarily associated with the assisting actuator 6.

With this configuration, in which some of the pressure sensors 87 are associated with the assisting actuators 6, an increase or decrease in the driving power of expansion/contraction driving of the assisting actuator 6 corresponding to the position touched by the user 1 is controlled. Accordingly, the user 1 may touch the wear main body 2 at the position where the driving power of expansion/contraction driving of the assisting actuators 6 is to be changed (increased or decreased).

The pressure sensor 87 to be associated may be located within a certain distance (for example, within 10 mm) from the target assisting actuator 6. In this way, the pressure sensor 87 and the assisting actuator 6 associated therewith are located within the certain distance. Thus, when the user 1 touches a position where the driving power of expansion/contraction driving of the assisting actuator 6 is to be changed (increased or decreased), the driving power of expansion/contraction driving of the assisting actuator 6 at the touched position is changed (increased or decreased). Accordingly, the driving power of expansion/contraction driving of the assisting actuator 6 can be intuitively adjusted (increased or decreased).

As an example, if the pressure sensor 87a that detects a third contact for a preliminary movement and the pressure sensor 87b that detects a first contact, a second contact, and an intermediate contact therebetween for a command input movement are arranged at different positions, both the sensors are easily distinguished from each other. For example, the pressure sensor 87a that detects a third contact may be arranged in a waist region where no assist is required, whereas the pressure sensor 87b that detects a first contact, a second contact, and an intermediate contact therebetween may be arranged in another region (see FIG. 3). Alternatively, the pressure sensors 87a and 87b are not distinguished from each other on the basis of their positions. If an input with the first threshold TH1 or larger sequentially occurs twice within a certain time period at a certain plurality of pressure sensors 87, it may be determined as a preliminary movement, and after that a first contact, a second contact, and an intermediate contact therebetween may be detected. The pattern of two sequential inputs within a certain time period may be stored in the storage unit 8a as a pattern of a preliminary movement (detection of a third contact). The third contact for a preliminary movement is at least a contact related to detection of a pressure value which is the first threshold TH1 or larger by the pressure sensor 87a.

Arrangement of Myoelectric Sensors

As a more specific example, the assist wear item 4 further includes the plurality of myoelectric sensors 7 (see white circles illustrated in FIGS. 2 and 3). The myoelectric sensors 7 are located so as to come into a direct or indirect contact with a skin of a portion of the user 1, detect a signal generated from the user 1, and output the signal to the controller 8. For example, the myoelectric sensors 7 are arranged at the positions where the individual assisting actuators 6 are arranged or around the positions, and detect whether or not the assist wear item 4 has come into contact with the user 1. The density at which the myoelectric sensors 7 are arranged in a region corresponding to a muscle at a portion of the user 1 may be higher than the density at which the myoelectric sensors 7 are arranged in a region other than the region corresponding to the muscle.

Structure of Wear Main Body

Figure 17:
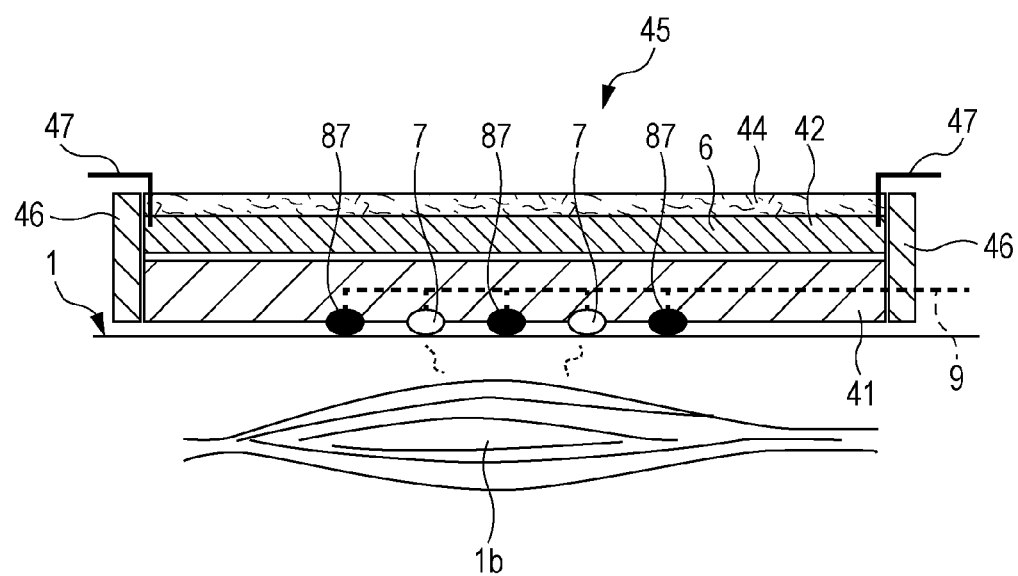
FIG. 17 is a cross-sectional view of an example structure of the wear main body.

FIG. 17 illustrates an example structure 45 of the wear main body 2. As illustrated in FIG. 17, the pressure sensors 87, the myoelectric sensors 7, and the wiring lines 9 for the sensors are arranged in a first layer 41 on the side nearest the user 1. The assisting actuators 6 are arranged in a second layer 42 on the first layer 41. A cover made of cloth or the like for covering the entire second layer 42 is arranged in a third layer 44, which is the outermost layer. With this structure, the example structure 45 has a three-layer structure as a whole. In FIG. 17, reference numeral 46 denotes assisting actuator fixing portions for fixing both ends of the assisting actuators 6, and reference numeral 47 denotes wiring lines for the assisting actuators 6.

Preliminary Movement/Command Input Movement Determining Unit

FIG. 4A is a block diagram related to the assist wear item 4. As illustrated in FIG. 4A, the controller 8 includes at least the preliminary movement/command input movement determining unit 8h. The preliminary movement/command input movement determining unit 8h receives outputs from the pressure sensors 87, and determines whether or not a preliminary movement has been performed and a command input movement has been performed on the basis of the received outputs. Only in a case where a preliminary movement and a command input movement have been performed, the preliminary movement/command input movement determining unit 8h outputs a signal for controlling the driving of the assisting actuators 6 to the assisting actuators 6 via a determining unit 8c, an actuator selecting unit 8e, and a driving unit 8d. In other words, the pressure sensors 87 and the preliminary movement/command input movement determining unit 8h enable input of an assist power increase/decrease command without using an input/output device 16, which will be described below. More specifically, the preliminary movement/command input movement determining unit 8*h* (the receiving unit 8*f* in the third modification example described below) is capable of, during expansion/contraction driving of the assisting actuators 6, receiving a detection result indicating a contact (touch) having a pressure value which is the first threshold TH1 or larger, that is, a third contact, from the pressure sensor 87*a* among the plurality of pressure sensors 87. After receiving the detection result indicating the third contact, the preliminary movement/command input movement determining unit 8*h* (the receiving unit 8*f* in the third modification example described below) is capable of, within a first time period t1 from the time when the detection result indicating the third contact is received, receiving a detection result indicating a contact having a pressure value which is the first threshold TH1 or larger, that is, a first contact, from the pressure sensor 87*b*. After receiving the detection result indicating the first contact, the preliminary movement/command input movement determining unit 8*h* (the receiving unit 8*f* in the third modification example described below) is capable of, within a second time period t2 from the time when the detection result indicating the first contact is received, receiving a detection result indicating a contact (swipe movement) having a pressure value which is the first threshold TH1 or larger from the pressure sensor 87*b*. To be capable of receiving a detection result indicating this contact (swipe movement) means that the preliminary movement/command input movement determining unit 8*h* (the receiving unit 8*f* in the third modification example described below) is capable of receiving a detection result indicating an intermediate contact and a second contact having a pressure value which is the first threshold TH1 or larger from a plurality of pressure sensors 87*b*. At this time, if the intermediate contact and second contact having a pressure value which is the first threshold TH1 or larger are sequentially detected, the controller 8 performs control to increase or decrease the driving power of expansion/contraction driving of the assisting actuators 6 on the basis of the distance between the positions of the first contact as an initial contact and the second contact as a last contact or the speed of movement between the positions of the first contact and the second contact. Here, as an example, pressure sensors are arranged with regular intervals, and the number of pressure sensors that have detected a contact during a swipe movement is counted, so that the distance between the positions of the first contact and the second contact can be easily detected.

FIG. 27 illustrates an example of sensor signals for determining detection of a first contact, an intermediate contact, and a second contact. FIG. 27 is a graph for describing the relationship between sensor signals, which are outputs from five pressure sensors, and the first threshold TH1. As illustrated in FIG. 27, whether or not a detection result indicating a third contact has been received is determined by the preliminary movement/command input movement determining unit 8*h* (the receiving unit 8*f* in the third modification example described below), on the basis of whether or not a pressure value (sensor signal) detected by two pressure sensors 87*a* in a waist region is equal to or larger than the first threshold TH1 and whether or not the order in which the first sensor and the second sensor are touched or the time interval therebetween matches a certain pattern. In FIG. 27, a detection result indicating a third contact is received in states (a) and (b) from the first sensor and the second sensor.

Subsequently, whether or not a detection result indicating a first contact has been received is determined by the preliminary movement/command input movement determining unit 8*h* (the command determination controller 88 in the third modification example described below), on the basis of whether or not a pressure value (sensor signal) detected by, for example, the pressure sensor 87*b* within the first time period t1 after a detection result indicating a pressure value is received as a detection result indicating a third contact from the pressure sensor 87 in a region other than the waist region is equal to or larger than the first threshold TH1. In FIG. 27, a detection result indicating a first contact is received in state (d) from the fifth sensor.

Subsequently, the preliminary movement/command input movement determining unit 8*h* (the command determination controller 88 in the third modification example described below) determines whether or not a detection result indicating an intermediate contact between a first contact and a second contact has been received, on the basis of whether or not a detected pressure value exceeds the first threshold TH1 and whether or not the distance between the pressure sensor that has detected the contact and the pressure sensor that detected a contact the last time is a certain distance or more. Here, the certain distance corresponds to the interval between the pressure sensors 87, for example, a distance corresponding to a range that can be simultaneously covered by a few fingers (about 5 to 10 mm).

Finally, a second contact is an intermediate contact that is last detected within the second time period t2 after the detection result indicating the first contact is received. In FIG. 27, it is assumed that two contacts in states (e) and (f) are detected by the fourth sensor and third sensor, and that, among the pressure sensors 87 related to these contacts, the pressure sensor 87 in state (f) corresponds to the second contact. Since there is detection of the intermediate contact in state (e) between detection of the first contact in state (d) and detection of the second contact in state (f), the number of the pressure sensors 87 related to detection of the intermediate contact in state (e) and detection of the second contact in state (f), that is, two, is counted by the preliminary movement/command input movement determining unit 8*h* (the command determination controller 88 in the third modification example described below). As described above, if the interval of the pressure sensors 87 is set to be almost constant, the distance between contact positions can be determined on the basis of the counted number of the pressure sensors. In some cases, information about movement speed can be used for determination of a command or as input information.

After the second time period t2 has elapsed since the detection of the first contact, an assist power adjustment command corresponding to the counted number of the pressure sensors 87 related to detection of the intermediate and second contacts is transmitted to the determining unit 8*c* from the preliminary movement/command input movement determining unit 8*h* (the command determination controller 88 in the third modification example described below). In response to this command, control is performed to increase or decrease the driving power of expansion/contraction driving of the assisting actuators 6. Here, the second time period t2 is a time period in which input of a command is received after a detection result indicating the first contact in state (d) is received from the first contact sensor (fifth sensor), and the contact that is last detected in the second time period t2 is regarded as the second contact (state (f)).

As an example, the preliminary movement/command input movement determining unit 8*h* maintains the setting in an initial state (the state before a preliminary movement) if a command input movement is not performed within the first time period t1 after a preliminary movement. If a first contact is detected after the preliminary movement, the second time period t2 is started. If an intermediate contact and a second contact, which correspond to a command input movement, are detected within the second time period t2 from the first contact, the preliminary movement/command input movement determining unit 8h counts the number of the pressure sensors 87 related to the intermediate contact and the second contact. After the second time period t2 has elapsed, the preliminary movement/command input movement determining unit 8h makes a setting so as to increase the assist power in accordance with the total number of the pressure sensors 87 related to the intermediate contact and the second contact. At this time, if the preliminary movement/command input movement determining unit 8f (the command determination controller 88 in the third modification example described below) receives a detection result indicating an intermediate contact and a second contact during expansion driving of the assisting actuators 6, the preliminary movement/command input movement determining unit 8h (the command determination controller 88 in the third modification example described below) performs control to increase the driving power of expansion driving of the assisting actuators 6. On the other hand, if the preliminary movement/command input movement determining unit 8f (the command determination controller 88 in the third modification example described below) receives a detection result indicating an intermediate contact and a second contact during contraction driving of the assisting actuators 6, the preliminary movement/command input movement determining unit 8h (the command determination controller 88 in the third modification example described below) performs control to increase the driving power of contraction driving of the assisting actuators 6.

The controller 8 may perform control to increase the driving power of expansion/contraction driving of the assisting actuators 6 as the maximum distance between two arbitrary pressure sensors 87 among the plurality of pressure sensors 87 that have detected an intermediate contact and a second contact increases, instead of performing control in accordance with the number of pressure sensors 87 (see FIG. 34B described below). Alternatively, by using contacts at two points like a pinch-in or pinch-out operation and changing the distance between the two points, an amount of increase in the driving power may be input.

Specific Configuration of Assisting Actuators

Figure 5A:
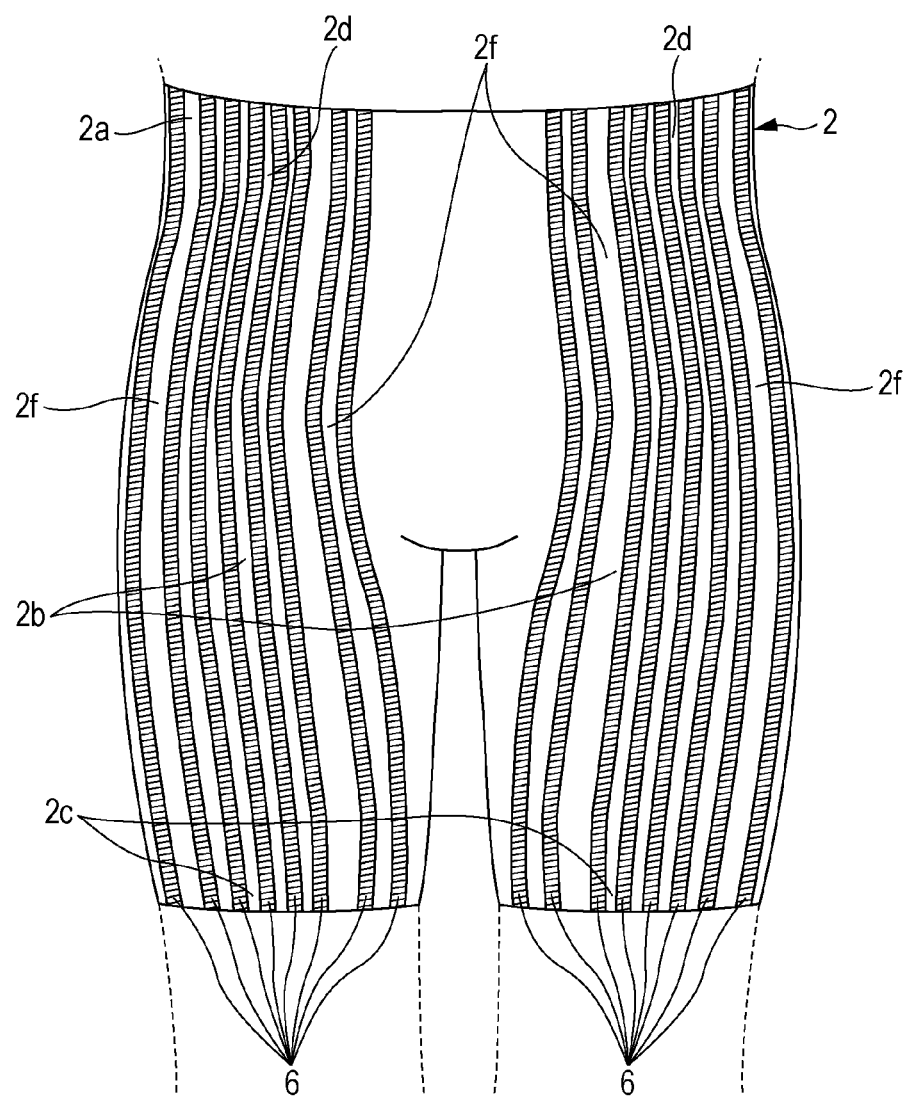
FIG. 5A is an explanatory diagram illustrating an arrangement state of assisting actuators on a front side of a wear main body.
Figure 7:
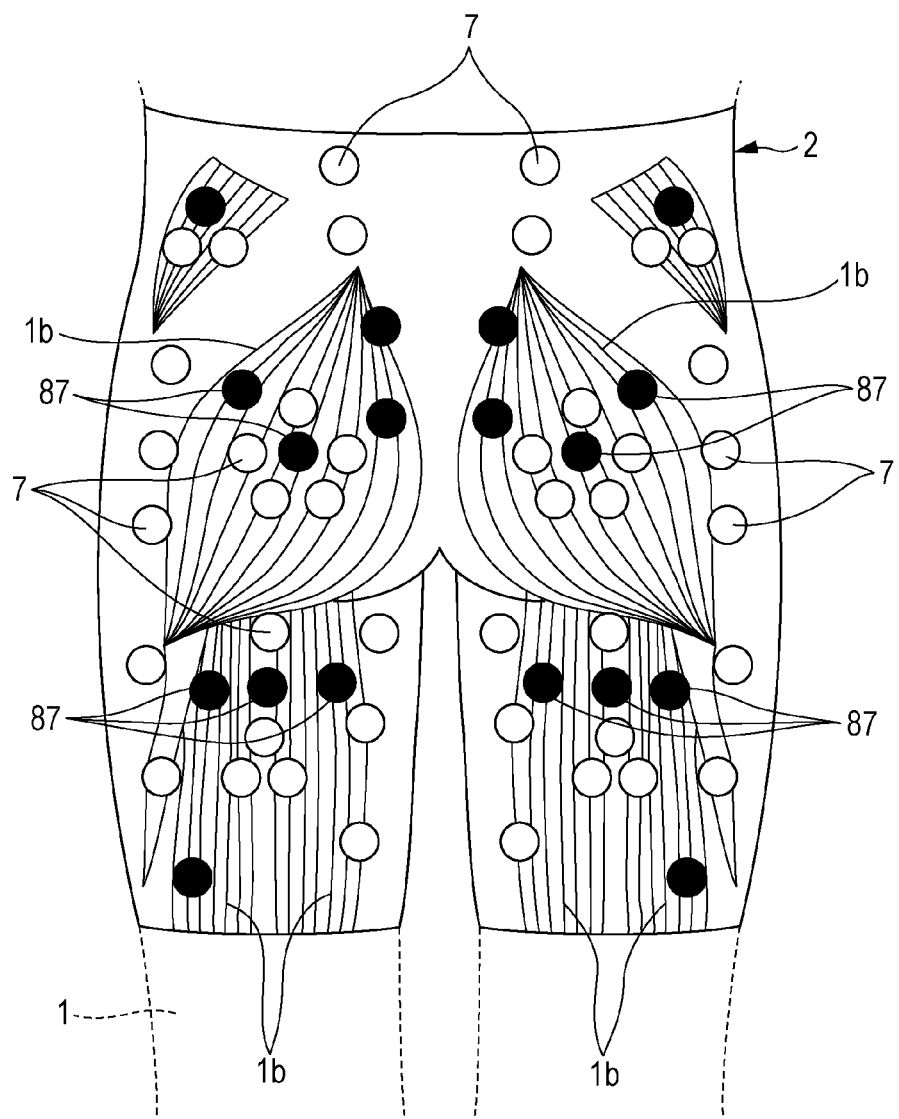
FIG. 7 is an explanatory diagram illustrating a relationship between muscles and an arrangement state of sensors on a back side of the wear main body.

FIG. 5A is an explanatory diagram illustrating an arrangement state of the assisting actuators 6 on the front side of the wear main body 2. FIGS. 6 and 7 are explanatory diagrams respectively illustrating a relationship between muscles and an arrangement state of the myoelectric sensors 7 and the pressure sensors 87 on the front side and back side of the wear main body 2.

Specifically, as illustrated in FIG. 5A, the assisting actuators 6 are densely arranged in portions 2d ranging from the front center of the thighs to a waist portion on the front and back sides of the wear main body 2 and in the portions corresponding to the portions 2d ranging from the back center of the thighs to the waist portion (the region corresponding to muscles), compared to portions 2f other than the portions 2d, so that the assist power of the assisting actuators 6 easily acts on the muscles of the thighs (muscles 1b in FIG. 6). In this way, the assisting actuators 6 are arranged densely or sparsely in accordance with muscles on the basis of an assist function, in other words, so that the assist function is efficiently utilized.

Figure 5B:
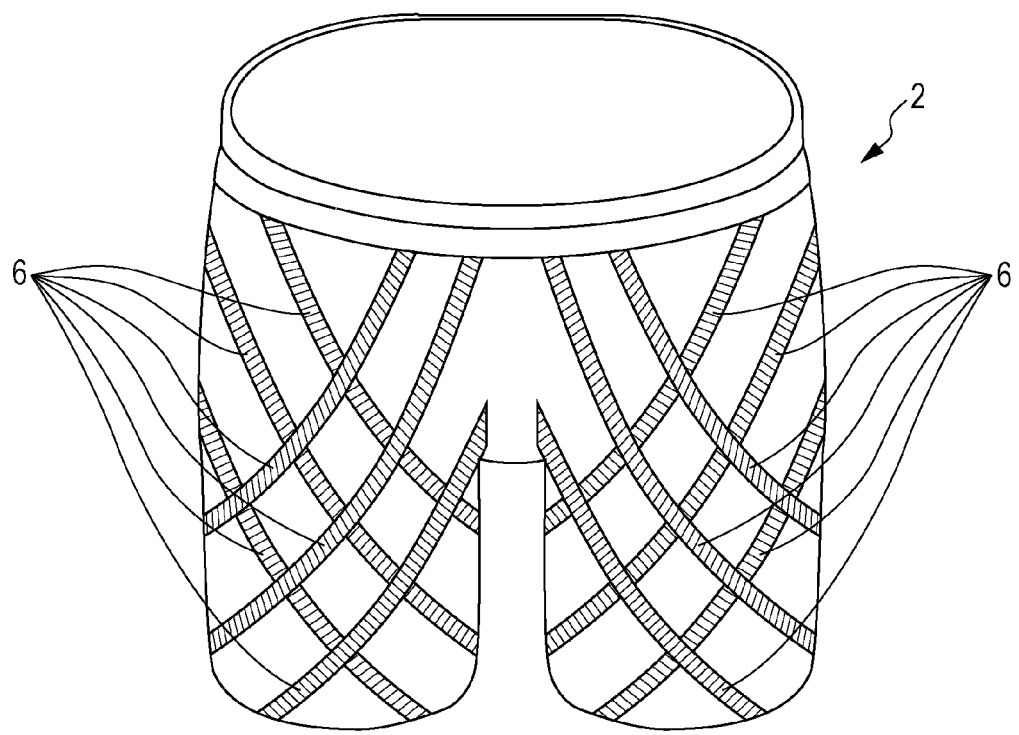
FIG. 5B is a perspective view of an arrangement state of assisting actuators according to a modification example of FIG. 5A.

The assisting actuators 6 may be arranged in almost parallel with one another, or may be arranged so as to cross one another as illustrated in FIG. 5B. In this case, the composite power of the assisting actuators 6 acts in the direction along an expansion/contraction direction of muscles in a target portion to be assisted.

All of the linear assisting actuators 6 used here are the same. Alternatively, different actuators may be used.

In the embodiment, actuators having the same structure are used as the linear assisting actuators 6.

Figure 8:
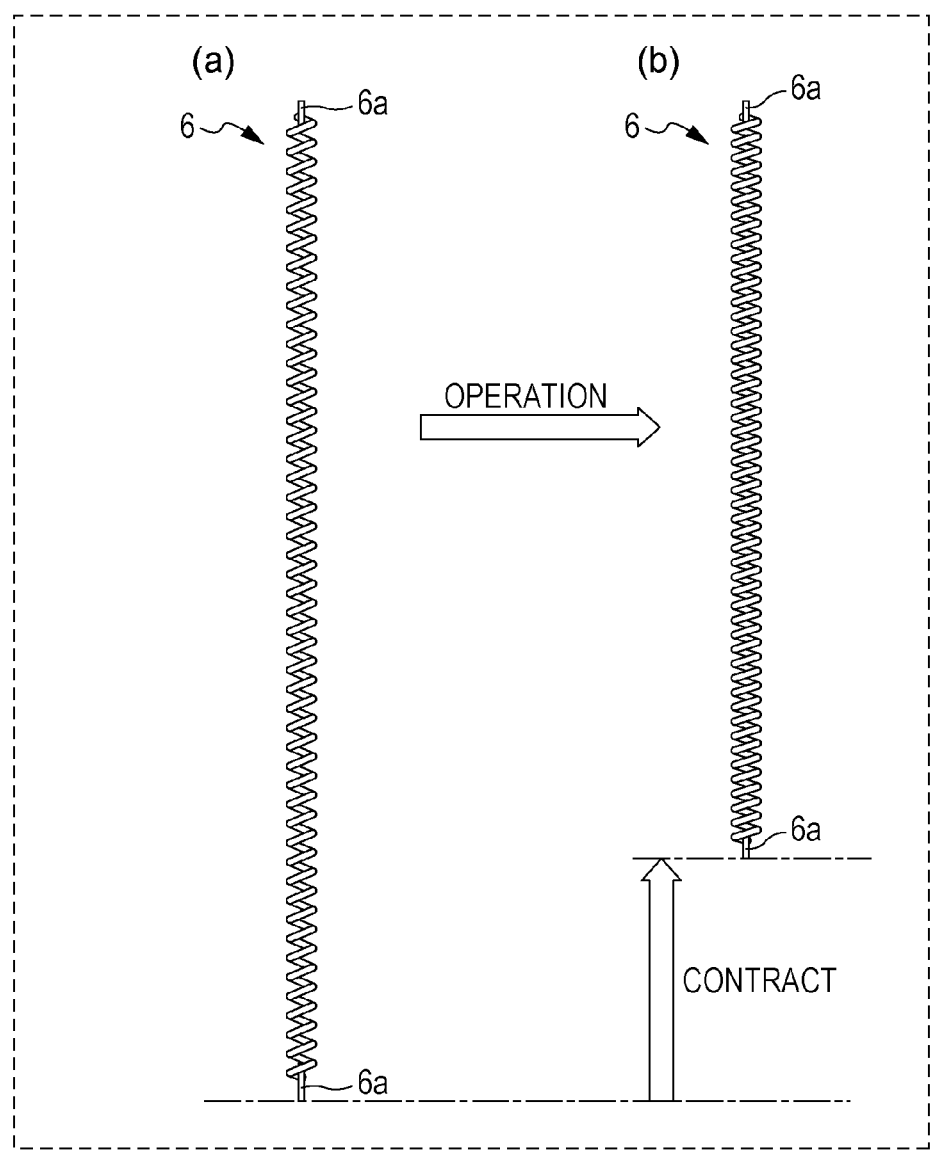
FIG. 8 is an explanatory diagram of an assisting actuator.
Figure 9:
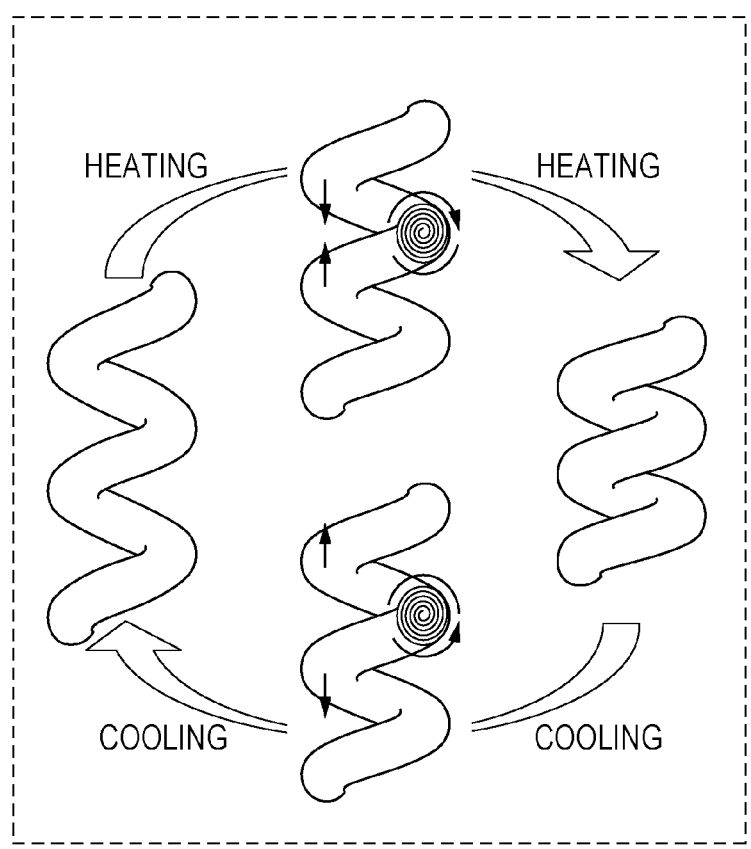
FIG. 9 is an enlarged explanatory diagram of the assisting actuator.
Figure 10:
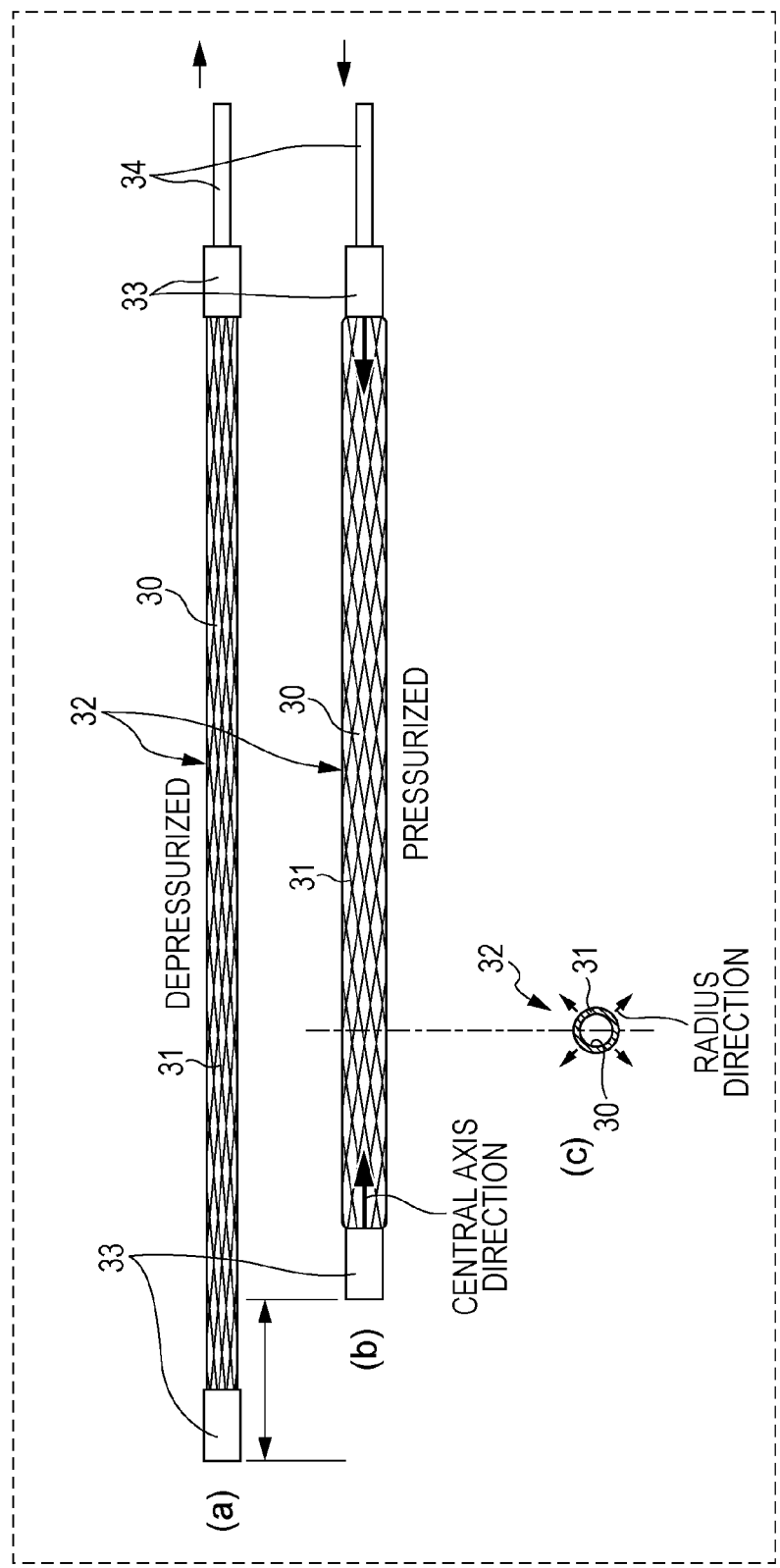
FIG. 10 is an explanatory diagram of another assisting actuator.
Figure 11:
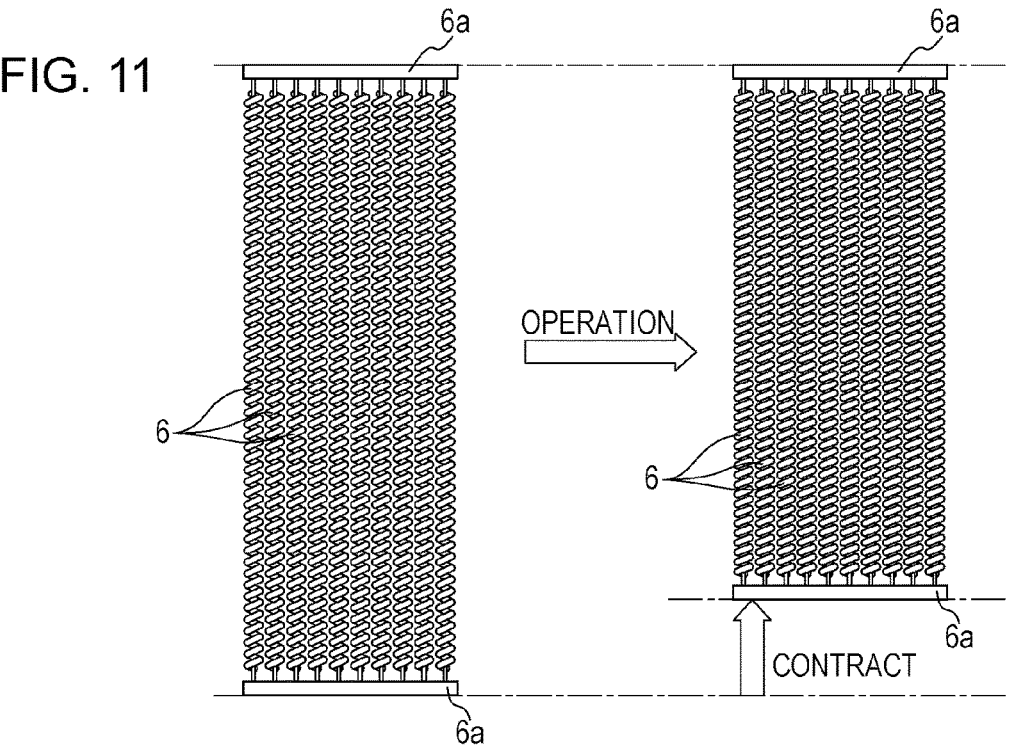
FIG. 11 is an explanatory diagram of assisting actuators according to a modification example of the assisting actuator in FIG. 8.
Figure 12:
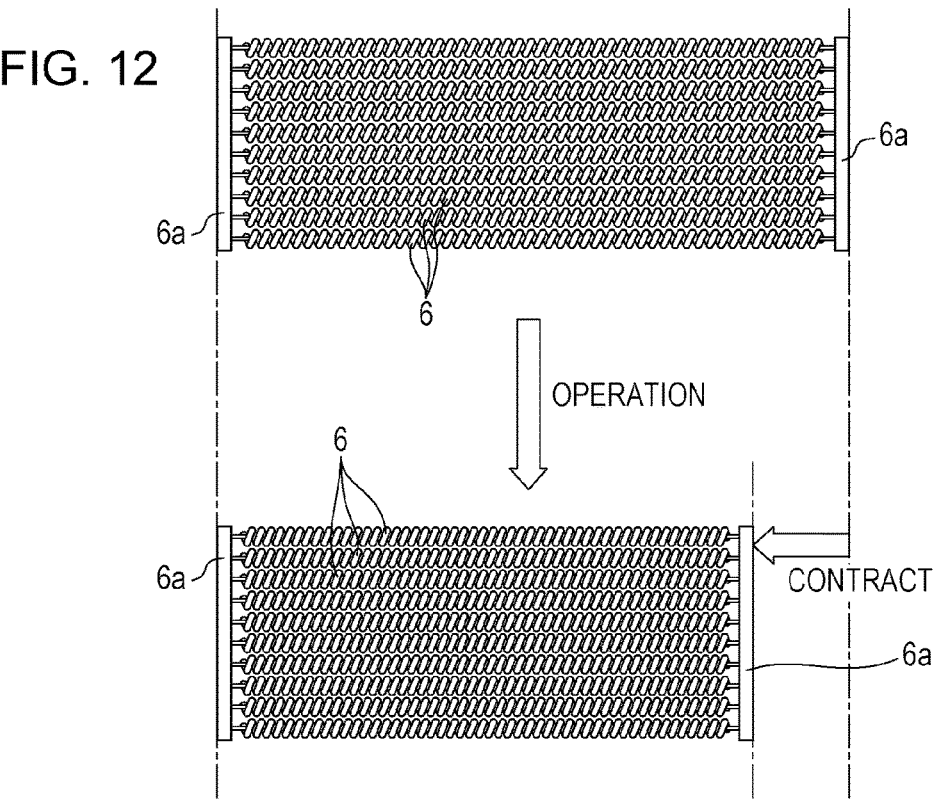
FIG. 12 is an explanatory diagram of assisting actuators according to a modification example of the assisting actuator in FIG. 8.
Figure 13:
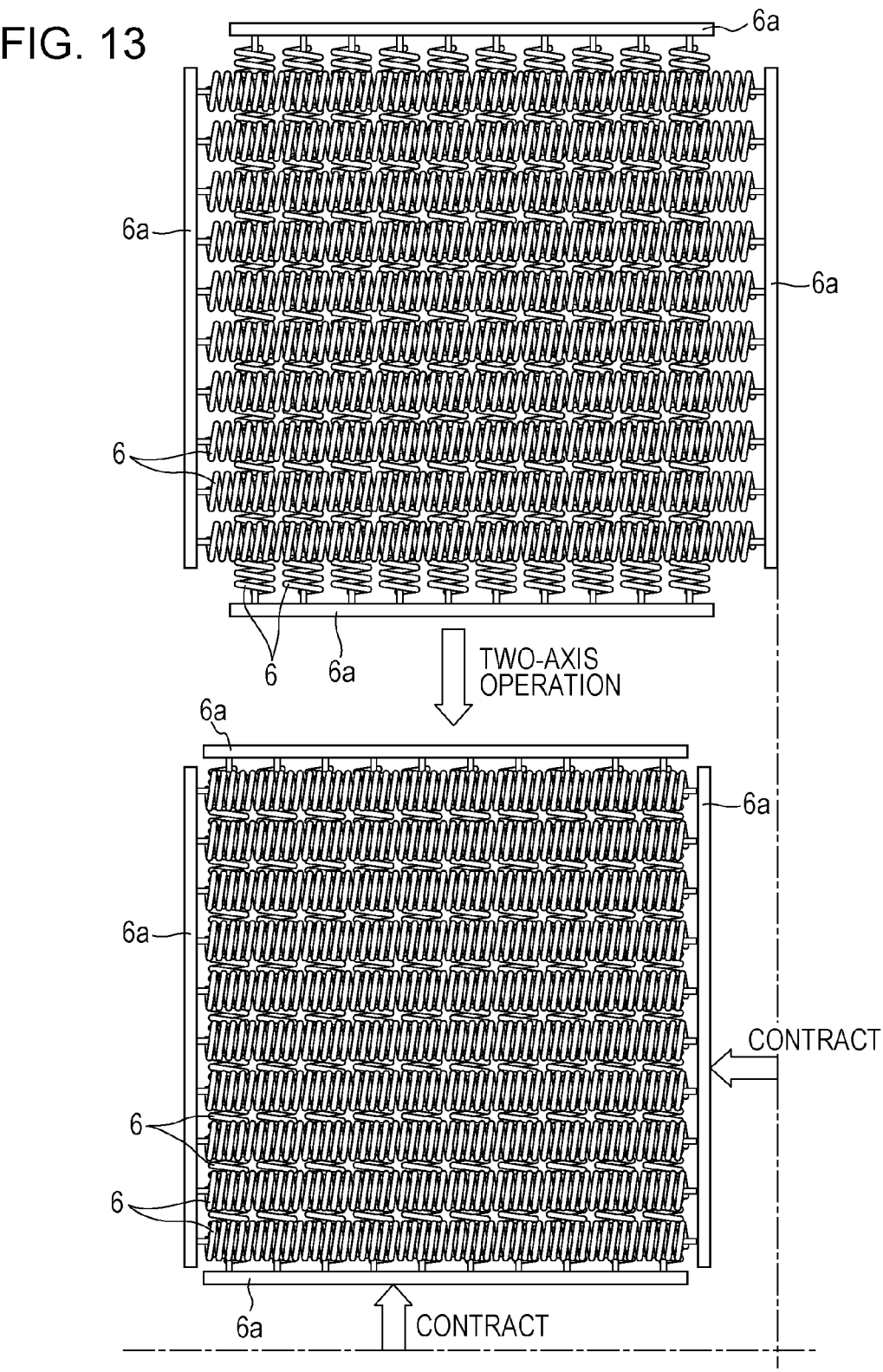
FIG. 13 is an explanatory diagram of assisting actuators according to a modification example of the assisting actuator in FIG. 8.

FIG. 8 is an explanatory diagram of an assisting actuator 6. FIG. 9 is an enlarged explanatory diagram of the assisting actuator 6. FIG. 10 is an explanatory diagram of another actuator. FIGS. 11 to 13 are explanatory diagrams of actuators according to modification examples of the assisting actuator 6 illustrated in FIG. 8. As illustrated in part (a) of FIG. 8, each assisting actuator 6 is formed of, for example, a helically wound linear member having a diameter of 0.233 mm and made of a synthetic resin. When a voltage is applied to electrodes 6a at both ends to energize and heat the assisting actuator 6, the entire length contracts as illustrated in part (b) of FIG. 8. On the other hand, when the assisting actuator 6 is no longer energized and heat is naturally discharged, the assisting actuator 6 expands to the original length. This is because, as illustrated in FIG. 9, heating causes torsion in a circumferential direction of the helically wound resin linear member and accordingly the entire length contracts. Cooling due to natural heat radiation causes the torsion to be cancelled in the circumferential direction and accordingly the entire length expands. Each assisting actuator 6 may be used alone. Alternatively, as illustrated in FIGS. 11 and 12, many assisting actuators 6 may be arranged in parallel in accordance with the level of power to be used and may be allowed to expand and contract in synchronization with one another. Alternatively, as illustrated in FIG. 13, many assisting actuators 6 may be arranged in parallel along two axis directions orthogonal to each other and may be allowed to expand and contract in synchronization with one another in the two axis directions.

An example of such an actuator is a linear actuator that contracts when heat is applied thereto, specifically, a high polymer actuator that is linear and capable of expanding and contracting in an axis direction. More specifically, a coiled actuator that is formed by twisting nylon fiber whose surface is silver coated, that contracts due to torque when current is applied to the silver coating to energize and heat the actuator, and that expands to the original length when the application of current is stopped, may be used. Such an actuator can be easily driven and the output per weight can be increased.

Another example of the actuator is a linear pneumatic actuator that expands and contracts in accordance with adjustment of an air pressure illustrated in FIG. 10. An example of the pneumatic actuator may be a Mckibben actuator 32 in which flanges 33 are fixed at both ends of a rubber tube 30 and a mesh fiber 31 is wound around the outer periphery of the rubber tube 30. In the Mckibben actuator 32, when a fluid (air or the like) is flown from a pipe 34 into the rubber tube 30 through one of the flanges 33, the rubber tube 30 is pressurized and expands. However, since the rubber tube 30 is restrained by the mesh fiber 31, the rubber tube 30 expands in a radius direction (see part (c) of FIG. 10) and significantly contracts in a center axis direction (see part (b) of FIG. 10). On the other hand, when the fluid (air or the like) is discharged from the rubber tube 30 via one of the flanges 33 and the pipe 34, the rubber tube 30 is depressurized, contracts in the radius direction (see part (c) of FIG. 10) together with the mesh fiber 31, and significantly expands in the center axis direction. As a specific example, the Mckibben actuator 32 having an outer diameter of 1.2 mm has already been developed. Such an actuator is capable of easily performing a holding operation by blocking coming in and out of the rubber tube 30 of a fluid.

The assisting actuators 6 described above are arranged in an axis direction of a portion of the user 1 (in other words, an axis direction of a muscle of the portion), but may be arranged in a direction that crosses the axis direction of the portion (for example, any direction such as an orthogonal direction or slanting direction). For example, if the assisting actuators 6 are caused to expand and contract in accordance with movements of the muscles 1*b* illustrated in FIG. 6, the movements of the muscles 1*b* can be assisted.

Specific Configuration of Myoelectric Sensors

The myoelectric sensors 7 measure a myoelectric potential, which is a voltage generated when a muscle is moved and is an example of a biological signal. The myoelectric sensors 7 are capable of detecting an instruction provided from the brain to a muscle, and thus the trackability of assisting muscular movements can be increased. Distortion sensors, acceleration sensors, gyro sensors, or the like may be used instead of the myoelectric sensors 7.

Figure 14:
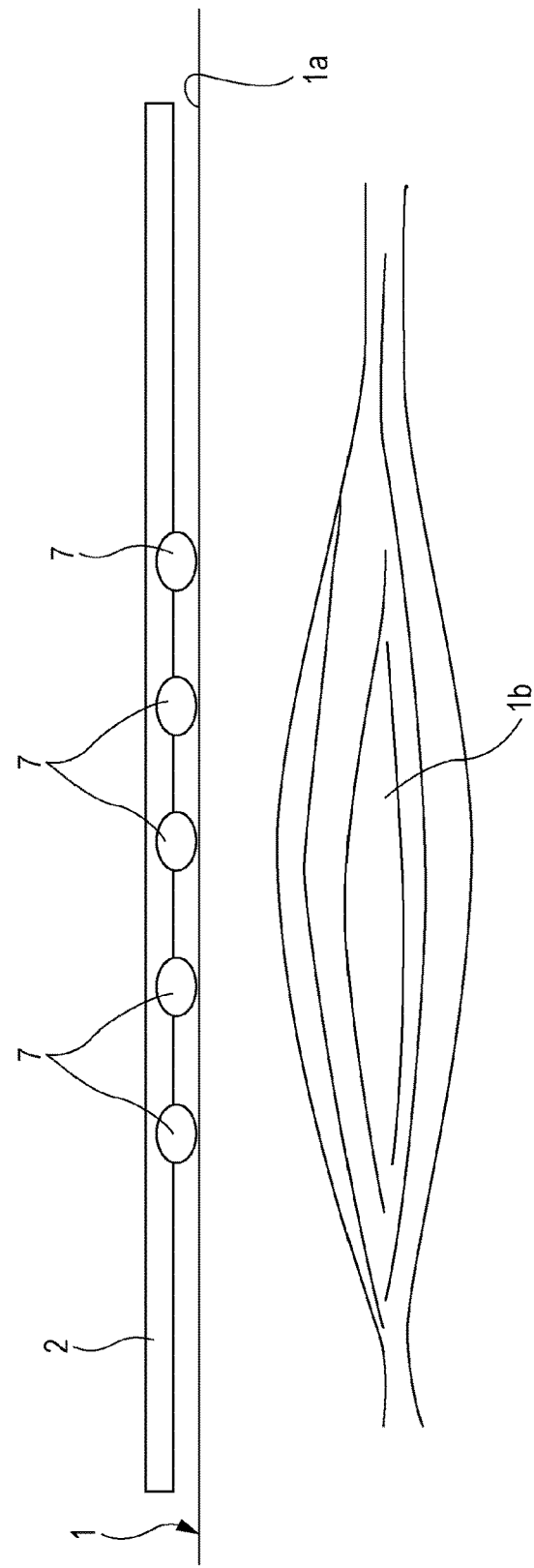
FIG. 14 is an explanatory diagram illustrating a relationship between an arrangement of sensors and a muscle.

The relationship between the arrangement of the myoelectric sensors 7 and a muscle 1*b* is illustrated in FIG. 14. The individual myoelectric sensors 7 are arranged at the positions where movements of the muscle 1*b* can be measured. For example, the myoelectric sensors 7 may be arranged at, among the positions corresponding to the muscle 1*b*, the positions corresponding to the positions where the muscle 1*b* moves the most greatly, so that the myoelectric sensors 7 can easily detect movements of the muscle 1*b*. Specifically, as illustrated in FIGS. 6 and 7, one or plural myoelectric sensors 7 are arranged in a region corresponding to the muscles 1*b* on both the front and back sides of the wear main body 2, so that movements of the muscles 1*b* can be easily measured by the myoelectric sensors 7. More specifically, on the front side of the wear main body 2, the myoelectric sensors 7 are arranged at the positions or regions corresponding to femoral muscles such as rectus femoris. On the back side of the wear main body 2, the myoelectric sensors 7 are arranged at the positions or regions corresponding to muscles of buttocks and hamstrings.

Figure 15:
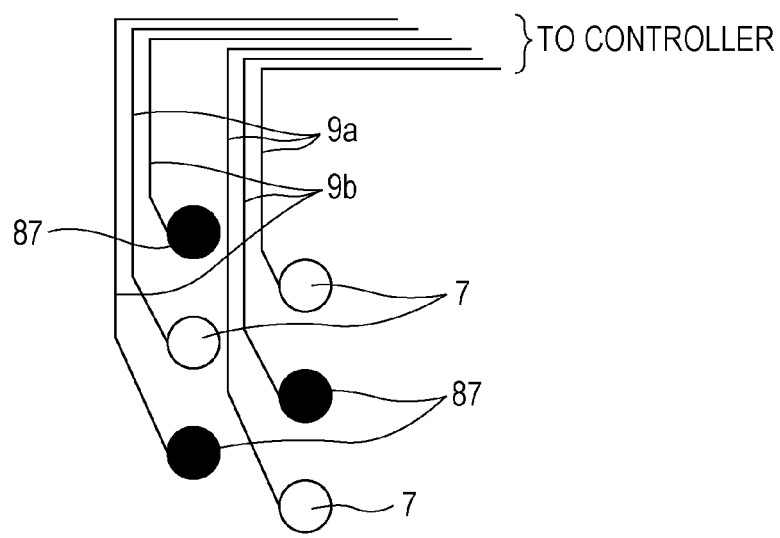
FIG. 15 is an explanatory diagram illustrating wiring lines extending from sensors in the case of analog wiring.
Figure 16:
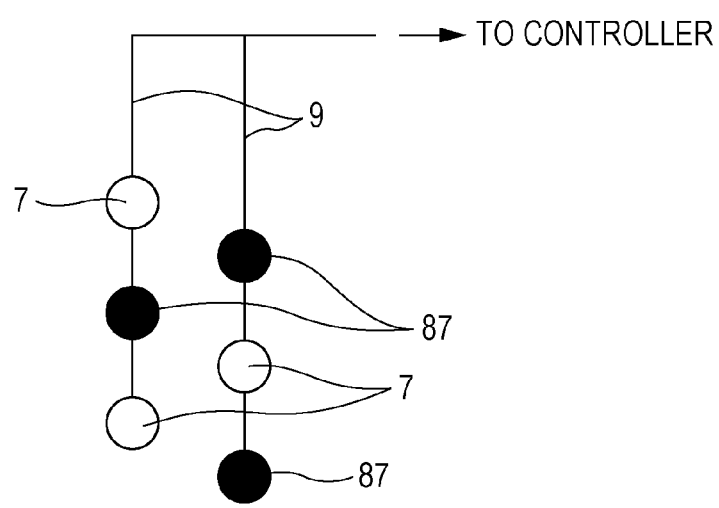
FIG. 16 is an explanatory diagram illustrating wiring lines extending from sensors in the case of digital wiring.

Wiring lines 9*a* extending from the myoelectric sensors 7 and wiring lines 9*b* extending from the pressure sensors 87 are arranged in the manner illustrated in FIG. 15 in the case of analog wiring. With such a configuration, signals of the individual myoelectric sensors 7 and signals of the individual pressure sensors 87 can be independently detected. On the other hand, in the case of digital wiring, wiring lines 9 extending from the individual myoelectric sensors 7 and the individual pressure sensors 87 are common wiring lines using a digital communication bus, as illustrated in FIG. 16. With such a configuration, the number of wiring lines can be decreased.

The wiring lines 9 for all the myoelectric sensors 7, all the pressure sensors 87, and all the assisting actuators 6 converge at the waist portion, which is the upper end portion of the pants, and are connected to the ring-shaped controller belt 3 through a wiring line 14.

Specific Configuration of Controller Belt

The controller belt 3 includes an engagement portion 3*a* at both ends thereof and can be worn on the waist of the user 1 by being engaged at the engagement portion 3*a*. The engagement portion 3*a* may be provided with a switch so that a start signal for the assisting actuators 6 is input to the controller 8 when the engagement portion 3*a* is engaged. Alternatively, a start signal for the assisting actuators 6 may be input by the user 1 from the input/output device 16 described below to the controller 8.

The controller belt 3 includes an operation device 18. As illustrated in FIG. 3, the operation device 18 includes the input/output device 16 that is capable of communicating with an information terminal 15 such as a smartphone and that includes an operation button, a speaker, a light-emitting diode (LED), a display, a wireless communication device, and so forth, and also includes the controller 8 connected to the input/output device 16. The input/output device 16 does not necessarily include the wireless communication device for communicating with the information terminal 15 such as a smartphone, and may receive only a direct input in the input/output device 16. The user 1 directly inputs an instruction to start or end assist into the input/output device 16 or indirectly inputs the instruction to the input/output device 16 via the information terminal 15 and controls driving of the assisting actuators 6 by using the controller 8.

An instruction to start or end an assist operation (driving of the assisting actuators 6) or an instruction to end an assist power adjustment operation is input to the input/output device 16 and is transmitted to the controller 8. Signals to start and end the assist operation (driving of the assisting actuators 6) may be automatically input through, for example, an engagement operation and a release operation of the engagement portion 3*a* of the controller belt 3.

The user 1, which is a human body, is capable of inputting an instruction to start or end an assist operation (driving of the assisting actuators 6) or an instruction to end an assist power adjustment operation into the information terminal 15 such as a smartphone. The instruction input to the information terminal 15 is transmitted from the information terminal 15 to the controller 8. In accordance with a warning instruction from the controller 8, a warning operation may be performed by the information terminal 15.

The controller belt 3 is not always necessary. In this case, the operation device 18 is attached to the wear main body 2 (see FIGS. 39 and 40 described below).

Controller and Determination of User Movement

The controller 8 includes, as illustrated in FIG. 4A, the preliminary movement/command input movement determining unit 8*h*, the storage unit 8*a*, an arithmetic unit 8*b*, the determining unit 8*c*, the actuator selecting unit 8*e*, and the driving unit 8*d*. The controller 8 controls the driving of the assisting actuators 6 on the basis of signals from the myoelectric sensors 7 in response to an instruction from the input/output device 16. Also, the controller 8 determines a preliminary movement and a command input movement as described above and makes a setting about an increase or decrease in the assist power.

The storage unit 8*a* stores thresholds to be used for determination of contact detection in the preliminary movement/command input movement determining unit 8*h* (a first threshold for determination of a preliminary movement and a command input movement, third to fifth thresholds described below, a certain distance, etc.), and also stores a plurality of assist operation modes in which the level of assist power or assist timing varies, or a single assist operation mode. The assist operation modes include, for example, a walking mode and a stairs up/down mode. The storage unit 8*a* stores, for each assist operation mode, a change pattern corresponding to a temporal change in values of the myoelectric sensors 7 calculated by the arithmetic unit 8*b*. Further, the storage unit 8*a* stores a program to be used by the determining unit 8*c* to determine the operation of the assisting actuators 6. Also, the storage unit 8*a* stores, in advance, position information about the individual myoelectric sensors 7 and the individual pressure sensors 87, position information about the assisting actuators 6 corresponding to the individual myoelectric sensors 7, and position information about the assisting actuators 6 corresponding to the individual pressure sensors 87.

The arithmetic unit 8*b* performs, as necessary, arithmetic operation for myoelectric sensor calibration, in which the strongest signal or a relatively strong signal is extracted from among a plurality of output signals from the myoelectric sensors 7, and a weight is applied to the plurality of output signals from the myoelectric sensors 7, and then an average value is calculated. Also, the arithmetic unit 8*b* may perform arithmetic operation for gain adjustment or noise cancelling on the output signals from the myoelectric sensors 7. The calculation result generated by the arithmetic unit 8*b* is transmitted from the arithmetic unit 8*b* to the determining unit 8*c*.

The determining unit 8*c* receives, from the preliminary movement/command input movement determining unit 8*h*, setting information about a driving condition for controlling an increase or decrease in the driving power of expansion/contraction driving of the assisting actuators 6 as command determination result information, and transmits an instruction to the actuator selecting unit 8*e*. Alternatively, the determining unit 8*c* may receive, from the preliminary movement/command input movement determining unit 8*h*, information representing the number of the pressure sensors 87 that have detected an intermediate contact and a second contact (the number of inputs of a command input movement) when the second time period t2 has elapsed, obtain an amount of increase in the assist power corresponding to the number of command input movements on the basis of the relationship information stored in the storage unit 8*a*, and provide an instruction to the actuator selecting unit 8*e* (see FIG. 34A).

In the case of an assist phase, the determining unit 8*c* determines a movement or state of the user 1 by comparing a temporal change in the values of the myoelectric sensors 7 calculated by the arithmetic unit 8*b* with a change pattern corresponding to the assist operation mode read from the storage unit 8*a*. Also, the determining unit 8*c* determines the operation of the assisting actuators 6 on the basis of a program stored in the storage unit 8*a* in advance, and provides an instruction to the actuator selecting unit 8*e* as necessary.

Figure 25:
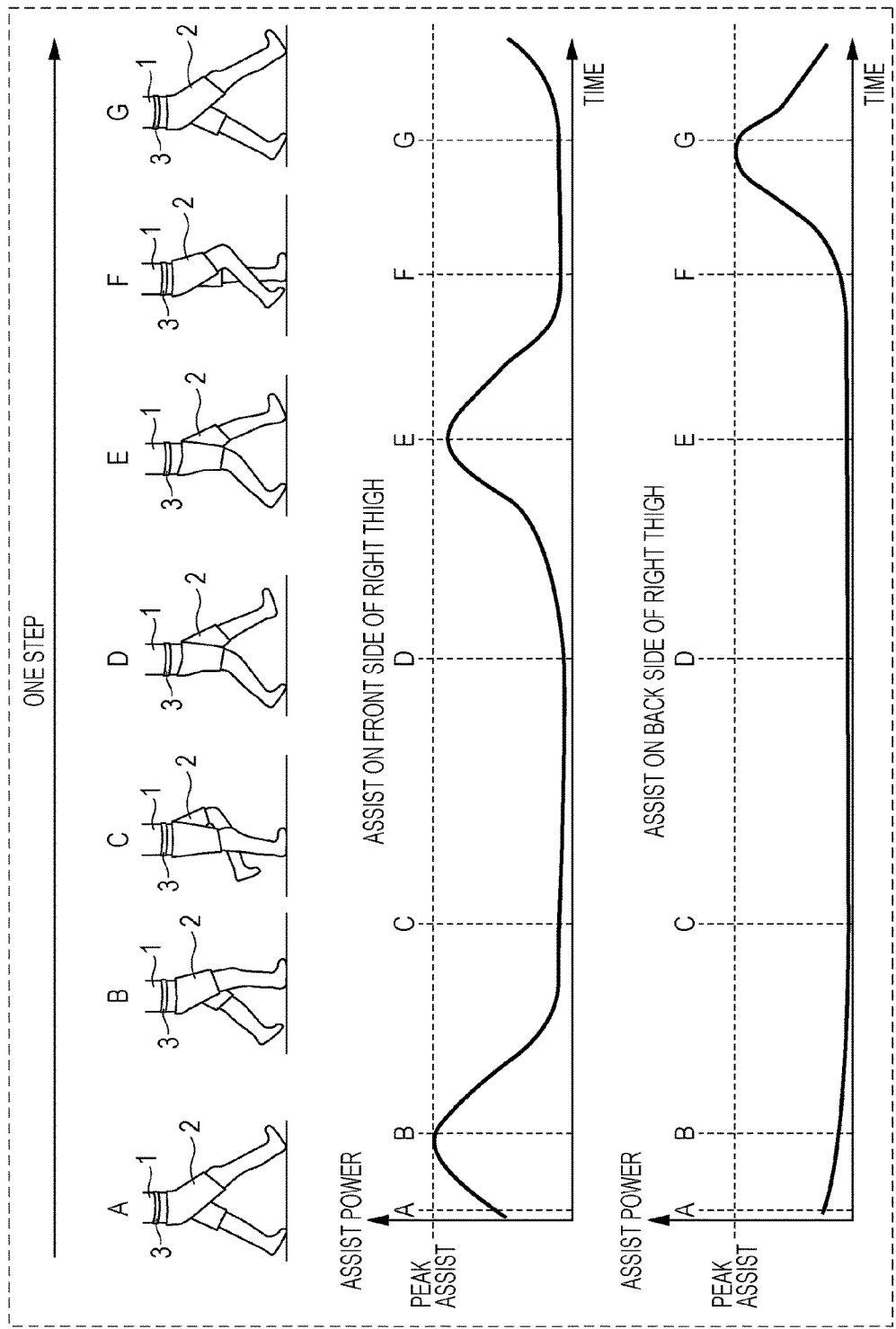
FIG. 25 is an explanatory diagram of a process of assisted walking using the assist wear item.

A specific example of determining a movement or state of the user 1 will be described with reference to FIGS. 25 and 4B to 4D. FIG. 25 is an explanatory diagram of a process of assisted walking using the assist wear item 4, and FIG. 4B is an explanatory diagram for describing comparative determination between actual signals used for determining a walking state in phase E among phases A to G in the process of assisted walking illustrated in FIG. 25 and signals in individual phases stored in the storage unit 8*a* (only phases E, F, and G are illustrated as a representative example). FIG. 4C is an explanatory diagram of signals in phase E of a time response pattern used for the determination illustrated in FIG. 4B, and FIG. 4D is an explanatory diagram of an example of driving the assisting actuators 6 (actuators A to E as a representative example) in phase E based on the determination illustrated in FIG. 4B. As an example, FIG. 4B illustrates actual signals used for determining a walking state in phase E among phases A to G in the process of assisted walking using the assist wear item 4 illustrated in FIG. 25, and signals in individual phases stored in the storage unit 8*a* (only phases E, F, and G are illustrated as a representative example). As an example of "signals of the myoelectric sensors 7 in individual phases stored in the storage unit 8*a*" illustrated in FIG. 4B, signal values of a first sensor (for example, a myoelectric sensor on the front side of the right thigh) in phase E and signal values of a second sensor (for example, a myoelectric sensor on the back side of the right thigh) in phase E are illustrated in FIG. 4C. In FIG. 4C, signal values are expressed by using digital values 0, 1, 2, and 3. As the digital value increases, the signal value of the myoelectric sensor increases. FIG. 4D illustrates an example of driving the assisting actuators 6 (only actuators A to E arranged on the front side of the right thigh are illustrated as a representative example) in phase E. In FIG. 4D, the drive levels of the actuators are expressed by 0, 1, 2, and 3. As the value of the drive level increases, the degree of contraction of the actuator increases.

Referring to FIG. 25, in the case of determining a movement or state of the user 1, the determining unit 8*c* compares actual signals output from the sensors arranged at specific positions, such as the first and second sensors, with the signals corresponding to the first and second sensors in individual phases stored in the storage unit 8*a*. The actual signals are the most similar to the signals in phase E in the time response pattern illustrated in FIG. 4B, and thus the determining unit 8*c* determines that the walking state of the user 1 corresponds to phase E.

On the basis of the determination result generated by the determining unit 8*c* and a program stored in the storage unit 8*a* in advance (here, a walking program), the determining unit 8*c* determines the operation of the assisting actuators 6 on the basis of a drive example of the assisting actuators 6 in phase E (only the actuators A to E are illustrated as a representative example) as illustrated in FIG. 4D, and provides an instruction to the driving unit 8*d* via the actuator selecting unit 8*e*. The driving unit 8*d* drives the corresponding assisting actuators 6 (the actuators A to E as a representative example) in response to the instruction provided from the determining unit 8*c*.

The driving unit 8*d* inputs information indicating which assisting actuator 6 is performing an assist operation and information that is necessary to adjust the assist power, such as the driving power at the time, to the determining unit 8*c* and the preliminary movement/command input movement determining unit 8*h* (the receiving unit 8*f* in the third modification example described below).

The preliminary movement/command input movement determining unit 8*h* is capable of receiving outputs from all the pressure sensors 87, and determines, on the basis of the outputs from the pressure sensors 87, whether or not a third contact as a preliminary movement has been detected by the pressure sensors 87, and whether or not a first contact, an intermediate contact, and a second contact as a command input movement have been detected by the pressure sensors 87. In the case of determining whether or not a first contact, an intermediate contact, and a second contact have been detected, if the second contact has been detected, the preliminary movement/command input movement determining unit 8*h* also determines the number of sensors that have detected the intermediate contact and the second contact. Further, the preliminary movement/command input movement determining unit 8*h* has, for example, a timer function, so as to be able to measure the first time period t1 and the second time period t2.

The operation of the preliminary movement/command input movement determining unit 8*h* (a preliminary movement/command input movement determination operation) will be described in detail below.

Myoelectric Sensor Calibration

Figure 18:
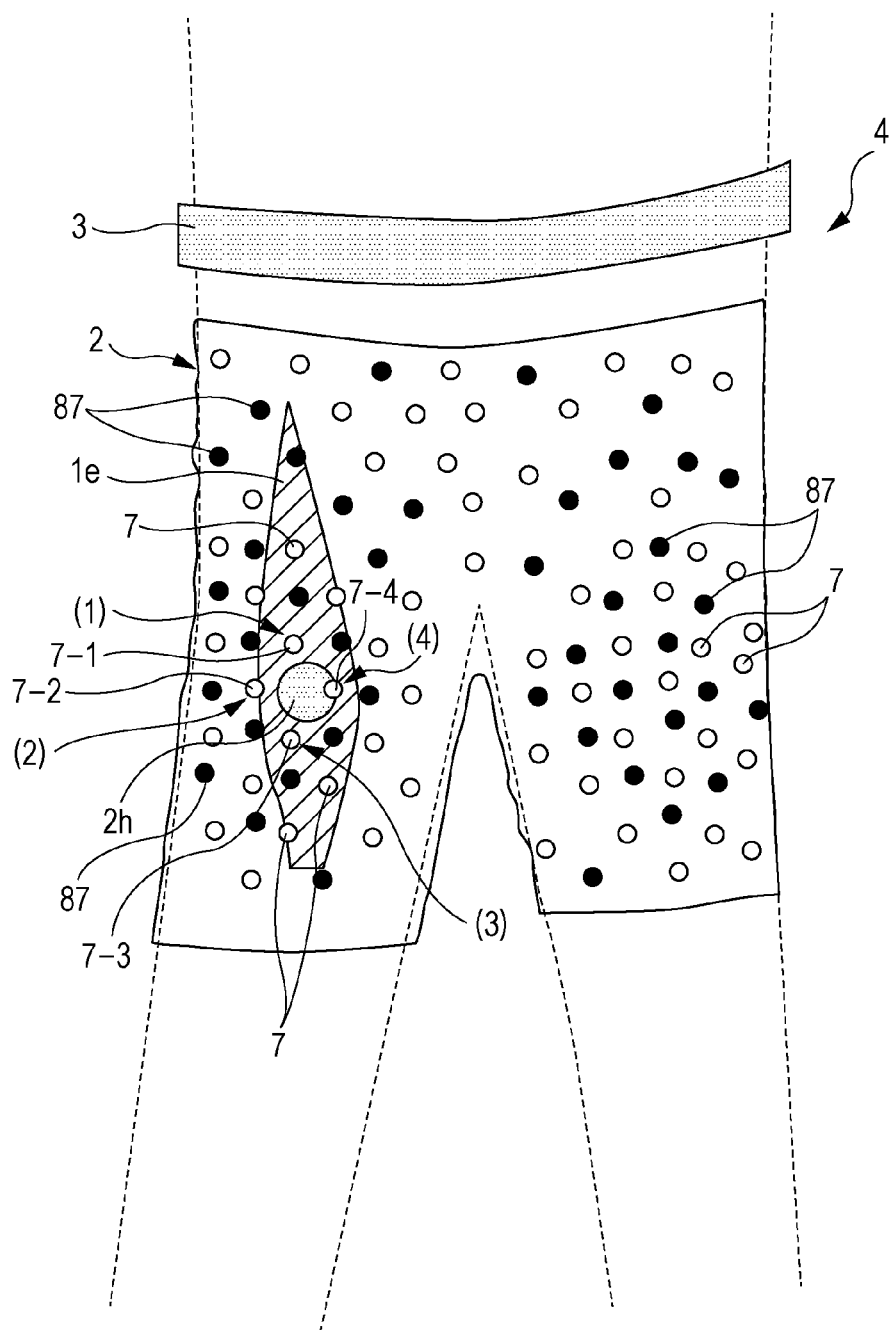
FIG. 18 is an explanatory diagram of sensor calibration.
Figure 19:
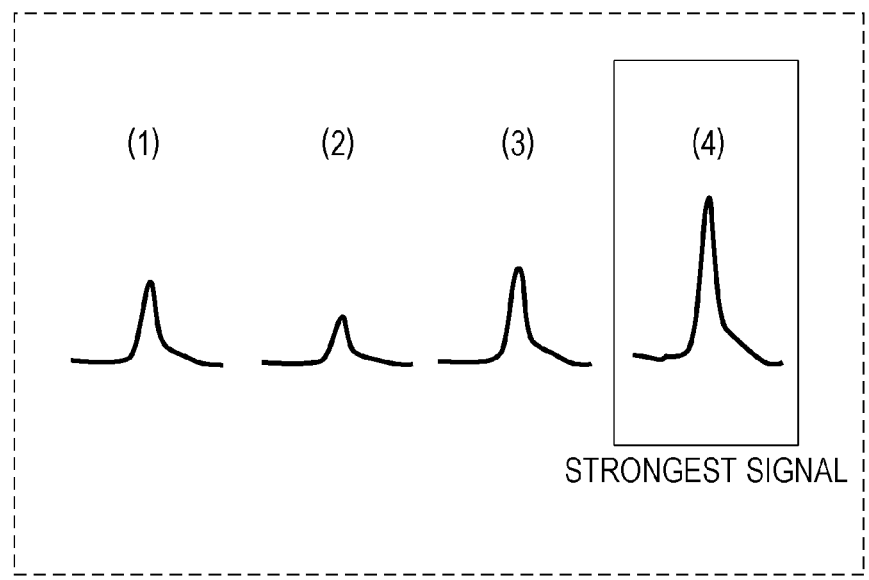
FIG. 19 is an explanatory diagram of a method for processing of sensor output.
Figure 20:
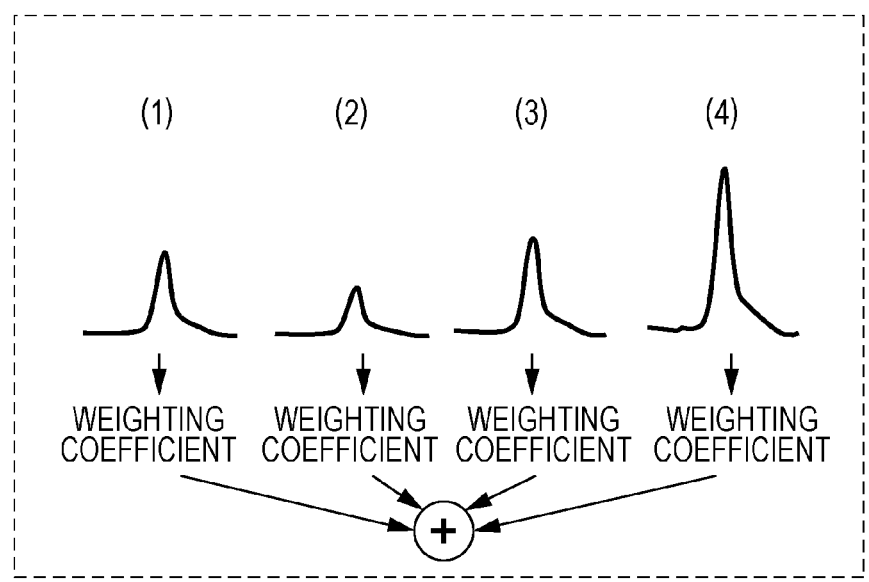
FIG. 20 is an explanatory diagram of another method for processing of sensor output.

FIG. 18 is an explanatory diagram of myoelectric sensor calibration. FIG. 19 is an explanatory diagram of a method for processing of output from the myoelectric sensors. FIG. 20 is an explanatory diagram of another method for processing of output from the myoelectric sensors.

Actually, the positions of the myoelectric sensors 7 vary among users or every time a user wears the assist wear item 4, depending on the features of the user 1 (body shape, sex, age, etc.) or how the wear main body 2 fits the user 1. In such a case, the controller 8 may be able to automatically perform myoelectric sensor calibration so that the user 1 does not need to perform adjustment each time.

For example, as illustrated in FIG. 18, biological signals such as myoelectric potentials are obtained by using the myoelectric sensors 7 arranged near a target region 2h located in accordance with a target muscle 1e, which is a muscle for which muscular movements are assisted. The target region 2h is set at, for example, a region where the signal level of the target muscle 1e is higher than the level of noise generated from the muscles near the target muscle 1e. Specifically, a target region for rectus femoris is set at a point on the rectus femoris and near an intermediate point between a pelvis (anterior inferior iliac spine) and a knee (tuberositas tibiae). The myoelectric sensors 7 arranged in the region which includes the intermediate point at the center and where displacement of the myoelectric sensors 7 may occur (for example, a region having a radius of 2 cm) obtain signals. In FIG. 18, the myoelectric sensors 7 are evenly arranged over the entire area of the wear main body 2.

Subsequently, among the biological signals obtained by the myoelectric sensors 7, the strongest signal is extracted by the arithmetic unit 8b of the controller 8. For example, as illustrated in FIG. 19, when it is assumed that output signals of four myoelectric sensors 7, that is, myoelectric sensors 7-1, 7-2, 7-3, and 7-4, are represented by (1), (2), (3), and (4), the output signal (4) of the myoelectric sensor 7-4 is the strongest signal.

As a result, the myoelectric sensor 7-4 that has detected the strongest output signal (4) is handled by the controller 8 as the myoelectric sensor 7 in the target region 2h. In this way, even if use of only the myoelectric sensors 7 in the target region 2h may cause a malfunction due to insufficient detection of power, correction, that is, myoelectric sensor calibration, can be performed by extracting the strongest signal and selecting, by the controller 8, the corresponding myoelectric sensor 7 as an appropriate myoelectric sensor 7 to be used in consideration of the output signals of the plurality of myoelectric sensors 7 near the target region 2h.

As another method for processing of the myoelectric sensor calibration, instead of extracting only the strongest signal, the arithmetic unit 8b of the controller 8 multiplies each of the output signals (1), (2), (3), and (4) by a weighting coefficient, adds the results, and divides the sum by the number of the output signals, so as to calculate an average value of the output signals, as illustrated in FIG. 20. The average value of the output signals calculated in this manner can be obtained as a corrected output signal, and myoelectric sensor calibration can be performed by using the corrected output signal.

Figure 21:
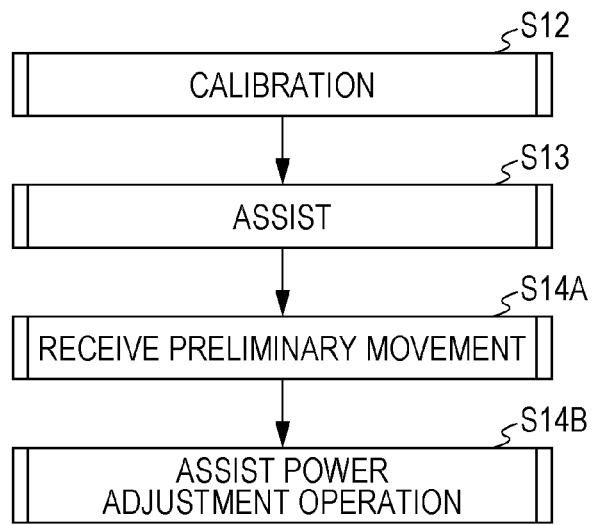
FIG. 21 is a flowchart illustrating a flow of entire operation in wear assist.

For example, the calibration is performed at the timing described below. FIG. 21 is a flowchart illustrating a flow of entire operation in wear assist.

As illustrated in FIG. 21, the wear main body 2 is worn on the user 1 and then myoelectric sensor calibration is performed in the above-described manner in step S12.

Subsequently, in step S13, an assist operation is performed by using the assisting actuators 6. At this time, for example, in a case where there are a plurality of selectable assist operation modes, any one of the modes may be selected by using the input/output device 16. For example, in a case where there are a walking mode and a stairs up/down mode, either of them is selected and then the assist operation is started.

Subsequently, in step S14A, during the assist operation using the assisting actuators 6, a preliminary movement for assist power adjustment is received.

Subsequently, in step S14B, after the preliminary movement has been received, an assist power adjustment operation is performed.

Actuator Calibration

Figure 22:
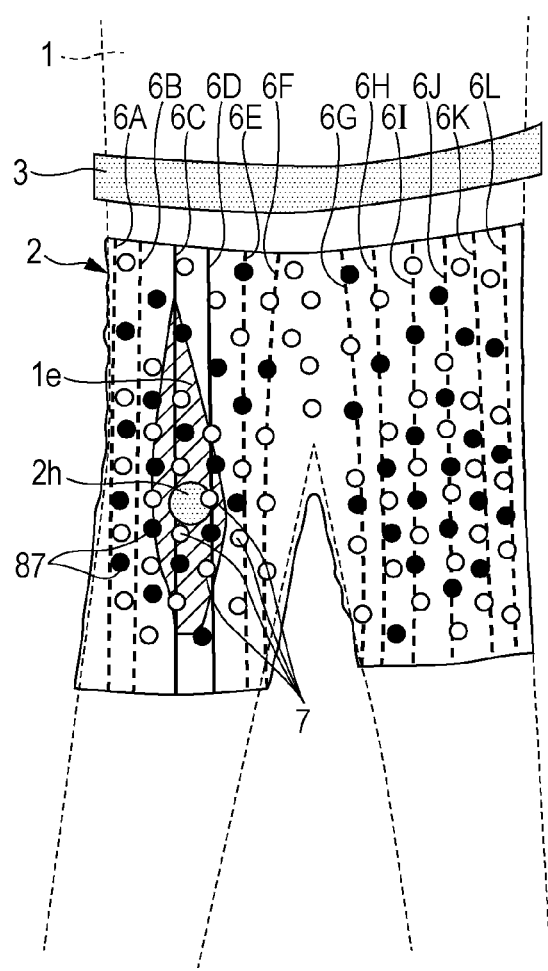
FIG. 22 is an explanatory diagram of the case of selecting different assisting actuators because muscle positions are different among users.
Figure 23:
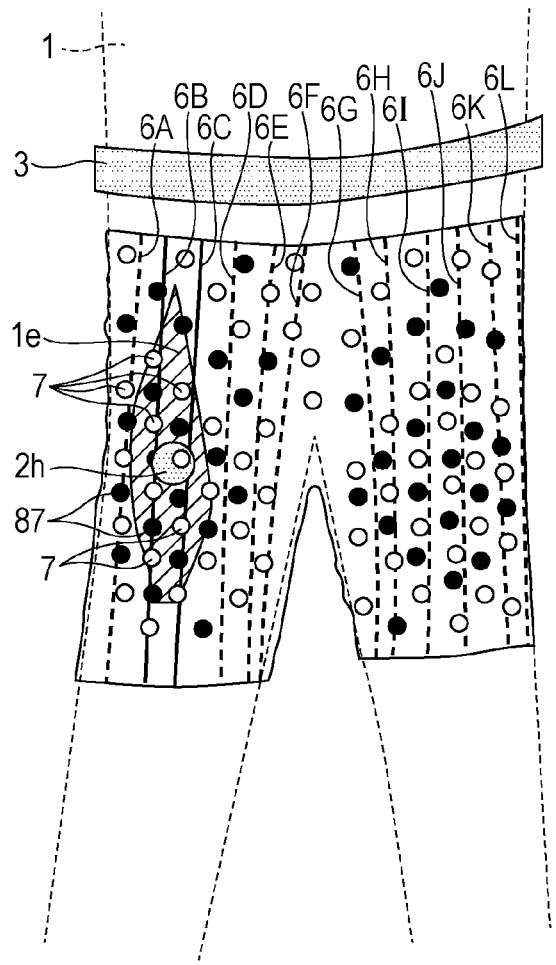
FIG. 23 is an explanatory diagram of the case of selecting different assisting actuators because muscle positions are different among users.
Figure 24:
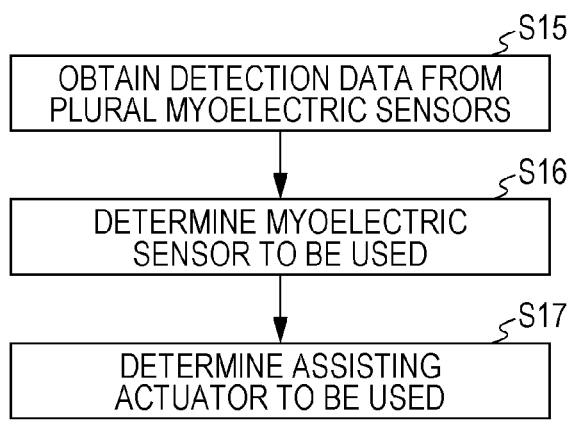
FIG. 24 is a flowchart illustrating a flow of operation of actuator calibration.

FIGS. 22 and 23 are explanatory diagrams in the case of selecting different assisting actuators because the positions of muscles vary among users 1. FIG. 24 is a flowchart illustrating a flow of operation of actuator calibration.

After the myoelectric sensor 7 corresponding to the strongest signal among the output signals of the plurality of myoelectric sensors 7 is extracted, the controller 8 selects the assisting actuator 6 arranged in association with the myoelectric sensor 7 (for example, arranged near the myoelectric sensor 7), and accordingly the assist power of the assisting actuator 6 can be appropriately transmitted from the assisting actuator 6 to the target muscle 1e. For example, as illustrated in FIG. 22, for a certain user 1, two assisting actuators 6C and 6D whose signals are stronger than those of the other assisting actuators 6A, 6B, 6E, and 6F may be used, among the assisting actuators 6A to 6F corresponding to the thigh and the vicinity thereof among the assisting actuators 6 arranged in the vertical direction of the wear main body 2. On the other hand, as illustrated in FIG. 23, for another user 1 whose muscle positions are different from those of the certain user 1, two assisting actuators 6B and 6C whose signals are stronger than those of the other assisting actuators 6A, 6D, 6E, and 6F may be used, among the assisting actuators 6A to 6F corresponding to the thigh and the vicinity thereof among the assisting actuators 6 arranged in the vertical direction of the wear main body 2. In this way, the controller 8 is able to detect the position of the muscle 1b relative to the wear main body 2 and appropriately select the assisting actuator 6 that is the nearest the muscle 1b on the basis of data output from the myoelectric sensors 7. Position information about the individual myoelectric sensors 7 and position information about the assisting actuators 6 corresponding to the individual myoelectric sensors 7 are stored in the storage unit 8a of the controller 8 in advance.

The actuator calibration is performed at the timing described below, for example.

As illustrated in FIG. 24, in step S15, the wear main body 2 is worn on the user 1 and then the controller 8 obtains detection data from the plurality of myoelectric sensors 7 near the target region 2h.

Subsequently, in step 16, the controller 8 determines, as the myoelectric sensor 7 to be used, the myoelectric sensor 7 corresponding to the strongest signal in the detection data of the plurality of myoelectric sensors 7.

Finally, in step S17, the controller 8 (actuator selecting unit 8e) determines, as the assisting actuator 6 to be used, the assisting actuator 6 corresponding to the determined myoelectric sensor 7.

Assisted Walking

FIG. 25 is an explanatory diagram of the process of assisted walking using the assist wear item 4.

As illustrated in FIG. 25, assist by the assisting actuators 6 for the muscles 1b on the front and back sides of the right thigh is performed in the following manner, for example, under the control performed by the controller 8. The assist is performed by generating an assist power that is linked to movements of the muscles 1b detected by the myoelectric sensors 7. Here, a description will be given of only the assisting actuators 6 corresponding to the muscles 1b on the front and back sides of the right thigh for simplicity. The same applies to the assisting actuators 6 corresponding to the muscles 1b on the front and back sides of the left thigh.

First, when the state shifts from state G to state A, the user 1 takes a step forward with the right leg and starts waking. At this time, assist by the assisting actuators 6 corresponding to the muscles 1b on the front side of the right thigh is increased, whereas assist by the assisting actuators 6 corresponding to the muscles 1b on the back side of the right thigh is gradually decreased. To increase assist may mean to cause the assisting actuators 6 to contract when the muscles contract or to cause the assisting actuators 6 to expand when the muscles expand.

Subsequently, when the state shifts from state A to state B, the user 1 starts taking the left leg away from the ground while keeping his/her weight on the right leg to support the body. When the state shifts to state B, assist by the assisting actuators 6 corresponding to the muscles 1b on the front side of the right thigh is performed to a maximum extent until the assist value reaches a peak value. At this time, assist by the assisting actuators 6 corresponding to the muscles 1b on the back side of the right thigh is performed only to a small extent.

Subsequently, when the state shifts from state B to state C, the user 1 keeps his/her whole weight on the right leg to support the body and the left leg is not in contact with the ground. At this time, assist by the assisting actuators 6 corresponding to the muscles 1b on the front side of the right thigh is gradually decreased, and assist by the assisting actuators 6 corresponding to the muscles 1b on the back side of the right thigh is performed only to a small extent.

Subsequently, when the state shifts from state C to state D, the user 1 takes a step forward with the left leg and starts waking. At this time, assist by the assisting actuators 6 corresponding to the muscles 1b on the front and back sides of the right thigh is performed only to a small extent.

Subsequently, when the state shifts from state D to state E, the user 1 starts taking the right leg away from the ground while keeping his/her weight on the left leg to support the body. When the state shifts from state D to state E, assist by the assisting actuators 6 corresponding to the muscles 1b on the front side of the right thigh is increased. At this time, assist by the assisting actuators 6 corresponding to the muscles 1b on the back side of the right thigh is performed only to a small extent.

Subsequently, when the state shifts from state E to state F, the user 1 keeps his/her whole weight on the left leg to support the body and the right leg is not in contact with the ground. At this time, assist by the assisting actuators 6 corresponding to the muscles 1b on the front side of the right thigh is gradually decreased, and assist by the assisting actuators 6 corresponding to the muscles 1b on the back side of the right thigh is performed only to a small extent.

Subsequently, when the state shifts from state F to state G, the user 1 takes a step forward with the right leg and starts waking. When the state shifts from state F to state G, assist by the assisting actuators 6 corresponding to the muscles 1b on the back side of the right thigh is increased to a maximum extent until the assist value reaches the peak value. At this time, assist by the assisting actuators 6 corresponding to the muscles 1b on the front side of the right thigh is performed only to a small extent.

In this assist example, the assist power is gradually changed in conjunction with the movements of the muscles 1b, but the embodiment is not limited thereto, and a pulsed assist power may be generated at the timing when assist is necessary. In a case where assist is performed only slightly, no assist may be performed.

Assist Phase

Figure 26A:
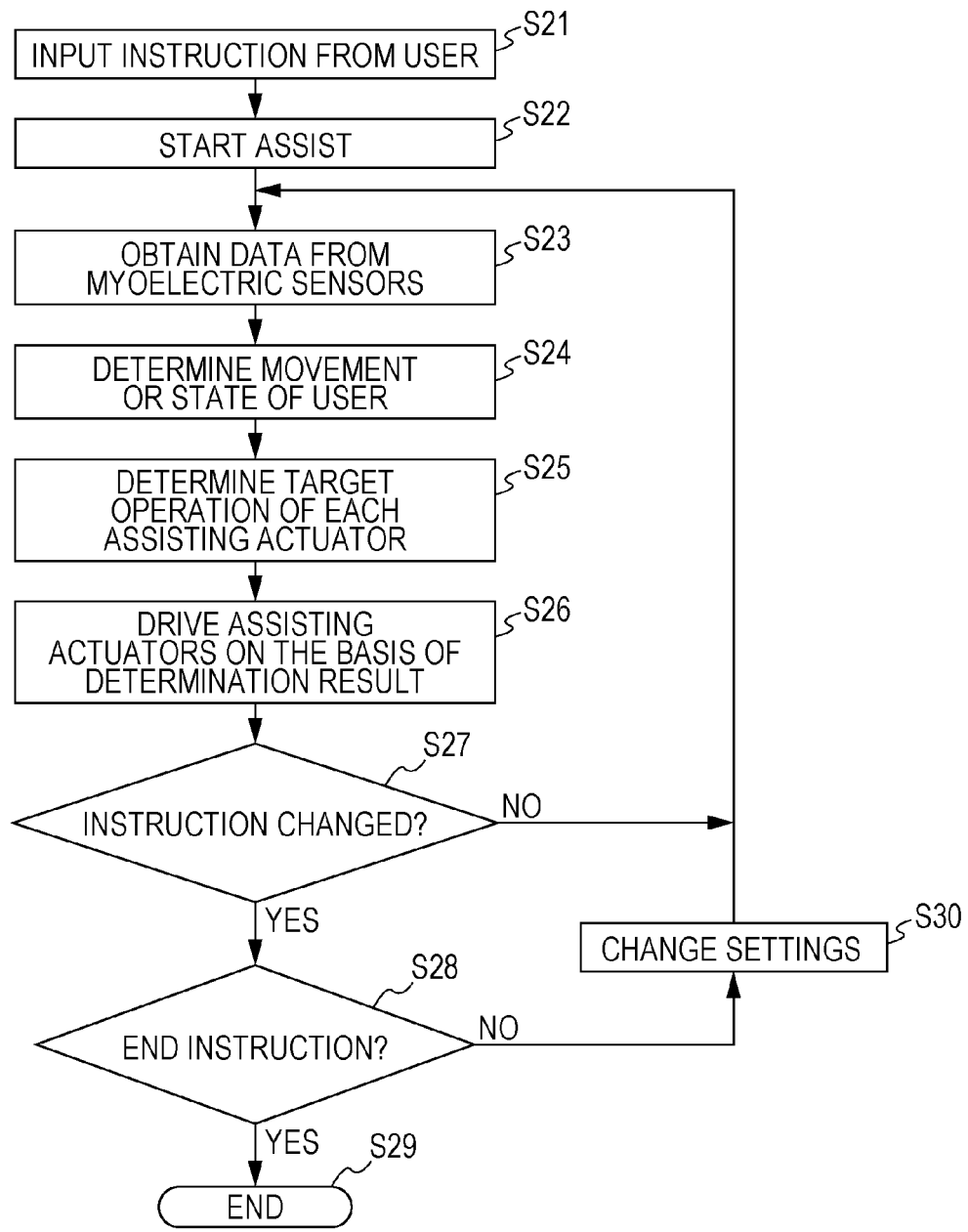
FIG. 26A is a flowchart of control of driving assisting actuators performed by a controller.

FIG. 26A is a flowchart of drive control of the assisting actuators 6 performed by the controller 8.

As illustrated in FIG. 26A, drive control of the assisting actuators 6 is performed by the controller 8 in the following manner. Here, the assisting actuators 6 to be used for assist vary depending on the walking state of the user 1. Pieces of information about movements of the muscles 1b can be obtained from the corresponding myoelectric sensors 7. As a result of comparing the pieces of information with walking patterns of a human by the controller 8, the walking state of the user 1 can be determined. Accordingly, the controller 8 is capable of selecting the assisting actuators 6 corresponding to the muscle 1b to be moved and performing assist in synchronization with the muscle 1b.

First, in step S21, the user 1 inputs an instruction about a walking mode or the like by using the input/output device 16.

Subsequently, in step S22, the controller 8 starts assist. That is, the controller 8 starts drive control of the assisting actuators 6 on the basis of a program stored in the storage unit 8a of the controller 8 in advance.

Subsequently, in step S23, the controller 8 obtains data from all the myoelectric sensors 7 before actually starting drive control of the assisting actuators 6.

Subsequently, in step S24, on the basis of the data obtained by the controller 8 from all the myoelectric sensors 7, the controller 8 determines the movement or state of the user 1. For example, the controller 8 determines whether the user 1 is now walking, and, if the user 1 is now walking, the controller 8 determines a walking state.

Subsequently, in step S25, on the basis of the determined movement or state of the user 1, the controller 8 determines the target operation of each assisting actuator 6. The target operation of the assisting actuator 6 may be when and how much the assisting actuator 6 is allowed to contract or when and how much the assisting actuator 6 is allowed to expand.

Subsequently, in step S26, on the basis of the target operations determined in step S25, the controller 8 performs drive control of the assisting actuators 6.

Subsequently, in step S27, the controller 8 determines whether or not an instruction has been changed by using the input/output device 16 or the like. If the controller 8 determines that an instruction has been changed, the processing proceeds to step S28. If the controller 8 determines that an instruction has not been changed, the processing returns to step S23.

Subsequently, in step S28, the controller 8 determines whether or not the change of instruction is an end instruction. If the controller 8 determines that the change of instruction is not an end instruction, the processing proceeds to step S30. If the controller 8 determines that the change of instruction is an end instruction, the processing proceeds to step S29.

Subsequently, in step S29, the series of operation processing ends.

In step S30, the controller 8 changes the settings on the basis of the change of instruction and then the processing returns to step S23.

Detailed Description of Operation of Preliminary Movement/Command Input Movement Determining Unit Next, a detailed description will be given of determination of a preliminary movement and a command input movement performed by the preliminary movement/command input movement determining unit 8h.

During a period in which the assisting actuators 6 are being driven to expand and contract by the driving unit 8d, detection results indicating a third contact as a preliminary movement are received from a plurality of pressure sensors 87. The period in which the assisting actuators 6 are being driven to expand and contract is actually a period in which the assisting actuators 6 are being driven to expand and contract or a period after a drive start signal for the assisting actuators 6 has been input. Specifically, when the drive start signal for the assisting actuators 6 is input from the driving unit 8d to the preliminary movement/command input movement determining unit 8h, the preliminary movement/command input movement determining unit 8h determines that the assisting actuators 6 are being driven to expand and contract.

The period of reception is limited for the following reason.

In many cases, when the user 1 wants to increase or decrease the driving power of expansion/contraction driving of the assisting actuators 6, the user 1 wants to fine-tune assist power when the user 1 is wearing the wear main body 2 and performing movements while receiving the assist power from the assist wear item 4. In other words, when the user 1 is not receiving assist power from the assist wear item 4, the user 1 is less likely to want to fine-tune the assist power, that is, want to increase or decrease the driving power of expansion/contraction driving of the assisting actuators 6.

In the embodiment, a detection result indicating a third contact is received while the assisting actuators 6 are driven to expand and contract, that is, while the user 1 is receiving assist power from the assist wear item 4. Accordingly, a detection result indicating a third contact is received while the user 1 is receiving assist power from the assist wear item 4 when the user 1 wants to fine-tune the assist power. As a result, in a situation where the user 1 is less likely to want to increase or decrease the driving power of expansion/contraction driving of the assisting actuators 6, reception of a detection result indicating a third contact is prevented, and accordingly an increase or decrease in the driving power not intended by the user 1 is prevented.

Whether or not a detection result is a detection result indicating a third contact as a preliminary movement and whether or not a detection result is a detection result indicating a first contact, an intermediate contact, and a second contact as a command input movement are determined on the basis of whether or not the movement at the time is a movement that can be accidentally performed by the user 1. This is because, for example, a movement of the user 1 of lightly tapping a portion of the wear main body 2 once or twice may be determined as both a movement of the user 1 in which the user's hand accidentally touches the portion and a movement of tapping the portion once or twice as an intended preliminary movement.

Thus, if the first threshold TH1 for determining a preliminary movement and a command input movement is set to a value that is equal to or larger than a pressure value detected when the user accidentally touches a portion, an increase or decrease in the driving power of expansion/contraction driving of the assisting actuators 6 not intended by the user 1 can be prevented. Alternatively, a preliminary movement may be formed of a plurality of touches, which is a movement that is less likely to be performed accidentally.

Specific examples of the preliminary movement performed by the user 1 include the following.

Figure 26B:
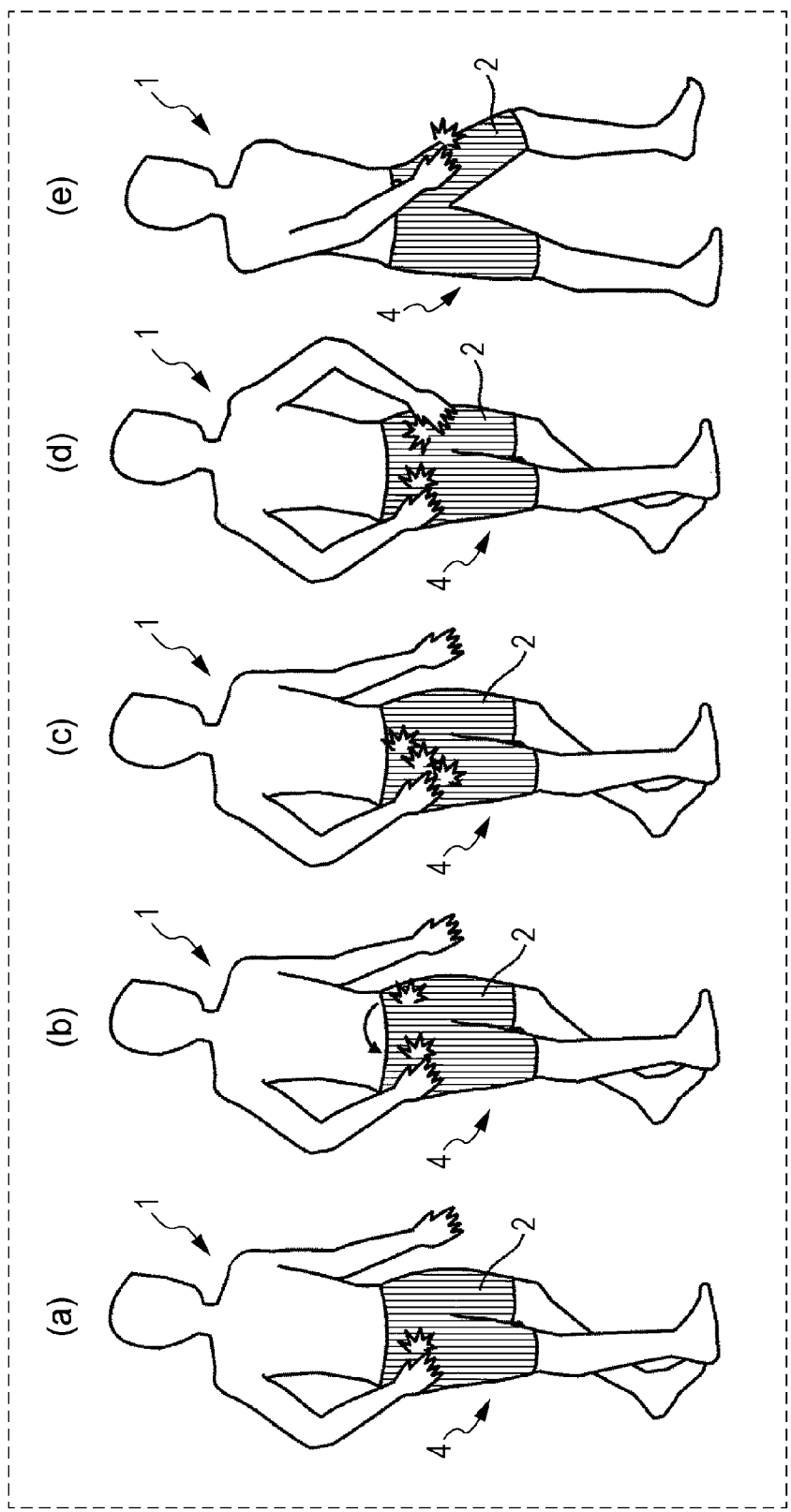
FIG. 26B is an explanatory diagram illustrating variation of a preliminary movement.

An example of the preliminary movement using one hand of the user 1 is movement in which the same position in the waist region is strongly tapped twice or more and a certain threshold (the first threshold) or more is output from the pressure sensors 87 at the same position twice or more (see part (a) of FIG. 26B). At this time, the time interval between the outputs may be set to a certain time interval (for example, one second) or less so as to prevent misrecognition more reliably. Alternatively, the outputs may be performed in certain rhythm (for example, the time interval between the first output and the second output is different from the time interval between the second output and the third output).

Another example of the preliminary movement using one hand of the user 1 is that different positions in the waist region are tapped a certain number of times (twice or more) and as a result a certain threshold (the first threshold) or more is output from the pressure sensors 87 at the same position or different positions the certain number of times. At this time, the order of the tapped positions may be determined (see part (b) of FIG. 26B) so as to prevent misrecognition more reliably.

Another example of the preliminary movement using one hand of the user 1 is that a movement of continuously and strongly pressing the same position or different positions for a certain time period is repeated twice or more and as a result a certain threshold (the first threshold) or more is output from the pressure sensors 87 at the same position or different positions twice or more in a certain time period or more.

Another example of the preliminary movement using one hand of the user 1 is that a certain position is tapped in specific rhythm (see part (c) of FIG. 26B) and as a result a certain threshold (the first threshold) or more is output from the pressure sensors 87 at a certain position at a certain interval within a certain time period.

Another example of the preliminary movement using one hand of the user 1 is a combination with a movement of the body of the user 1 (for example, a portion of a leg is tapped during a leg lift movement (see part (e) of FIG. 26B)) and as a result a certain threshold (the first threshold) or more is output from the pressure sensors 87 at the position where an operating assisting actuator 6 is located or the vicinity thereof twice or more.

An example of the preliminary movement using both hands of the user 1 is that a movement of simultaneously tapping once different positions by both hands or continuously pressing the different positions by both hands for a certain time period is repeated twice (see part (d) of FIG. 26B) and as a result simultaneous output of a certain threshold (the first threshold) or more from a plurality of pressure sensors 87 at the different positions occurs twice, or simultaneous output of the certain threshold (the first threshold) or more occurs twice in a certain time period or more.

Another example of the preliminary movement using both hands of the user 1 is that different positions are sequentially tapped by both hands (once by each hand) within a certain time period or the different positions are continuously pressed by both hands for a certain time period or more, and as a result a certain threshold (the first threshold) or more is output from a plurality of pressure sensors 87 at different positions within a certain time period or in the certain time period or more.

A command input movement is performed by making a touch within the first time period t1 from a preliminary movement so as to prevent misrecognition. With a method similar to the above-described preliminary movement, misrecognition can be prevented more reliably.

An example of the command input movement using one hand of the user 1 is that a linear up-down or down-up swipe movement along a vertical direction, which is an expansion/contraction direction of a muscle, is performed, and there are three or more outputs of a certain threshold (the first threshold) or more from three or more pressure sensors 87 at different positions. Another example of the command input movement using one hand of the user 1 is that a linear left-to-right or right-to-left swipe movement along a horizontal direction is performed (see the swipe movement indicated by an arrow X1 in FIG. 29), and there are three or more outputs of a certain threshold (the first threshold) or more from three or more pressure sensors 87 at different positions.

Figure 29:
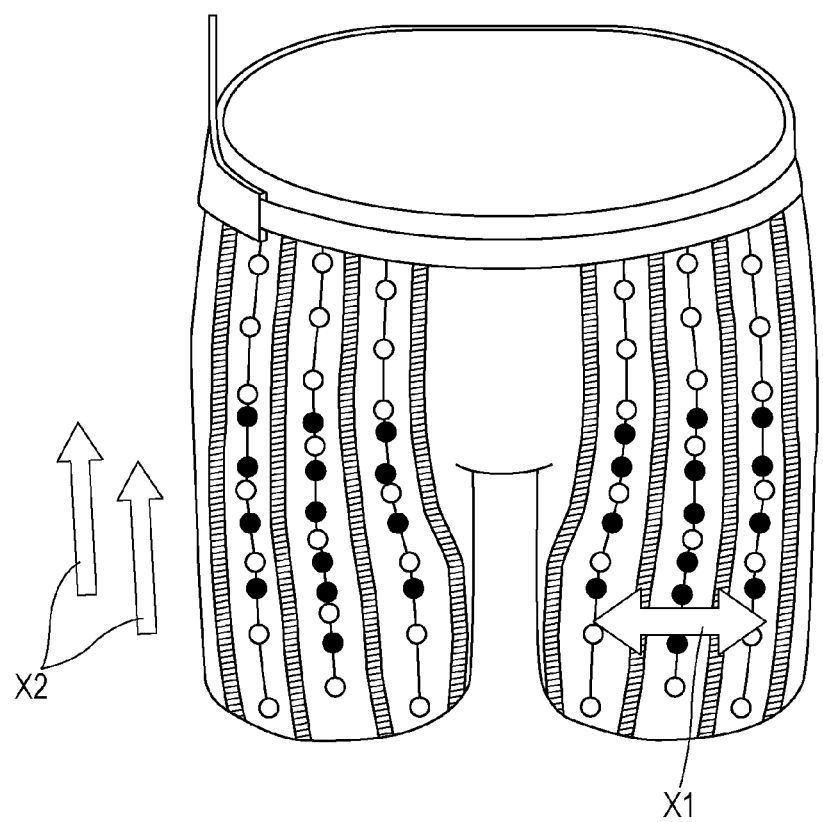
FIG. 29 is an explanatory diagram illustrating a relationship between the assist wear item and a swipe movement.
Figure 34C:
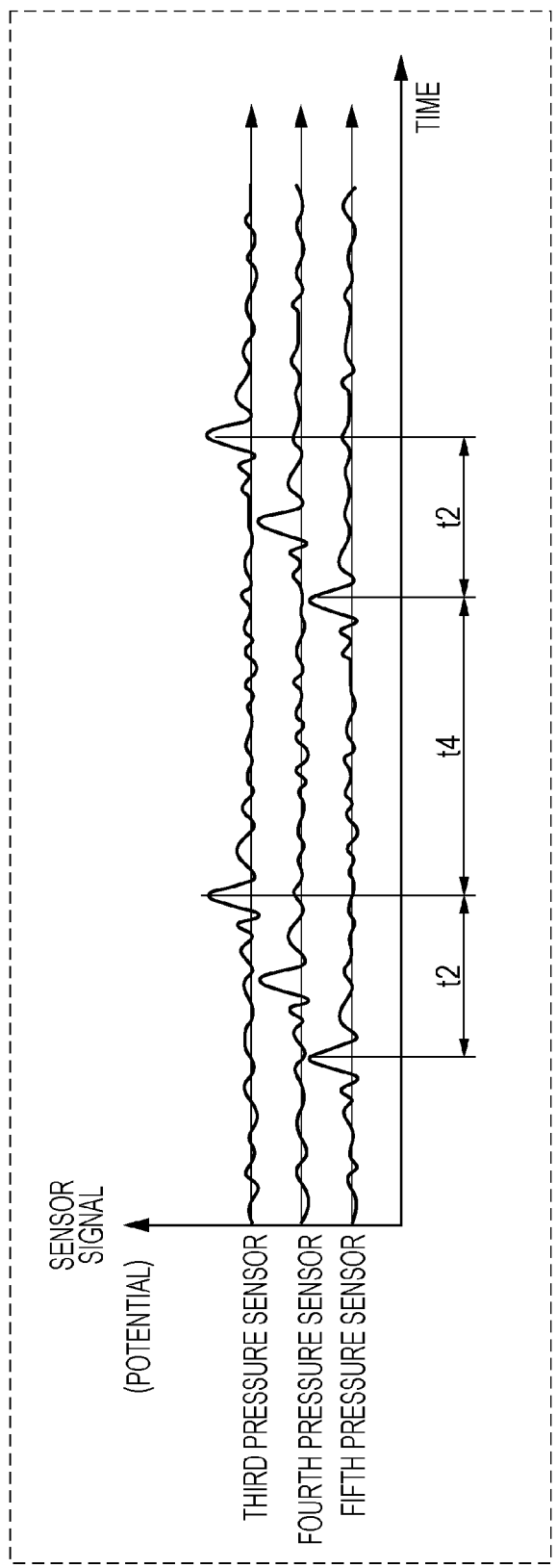
FIG. 34C is a graph for describing a relationship among sensor signals which are outputs from five pressure sensors in the case of performing a swipe operation twice, a first threshold, and a first time period.

Another example of the command input movement using one hand of the user 1 is a case where the above-described swipe movement in the vertical or horizontal direction is performed a plurality of times (see the swipe movement indicated by an arrow X2 in FIG. 29 and FIG. 34C). In this case, within a certain time period t4 after the second time period t2 has elapsed, a first contact is detected again, and then the second time period t2 starts and an intermediate contact and a second contact are received and counted, and thereby a determination can be made.

Another example of the command input movement using one hand of the user 1 is that, as a result of a combination with a movement of the body of the user 1 (for example, a portion of a leg is swiped during a leg lift movement), there are three or more outputs of a certain threshold (the first threshold) or more from three or more pressure sensors 87 at the position where the operating assisting actuator 6 is arranged or around the position.

The above-described preliminary movements and command input movements are merely examples, and a plurality of methods can be used in combination. In any of the movement examples, detection of a third contact as a preliminary movement and detection of a first contact, an intermediate contact, and a second contact as a command input movement are performed by using the processing method described above.

FIG. 27 is a graph for escribing the relationship among sensor signals, which are outputs from five pressure sensors 87 (first to fifth pressure sensors), the first threshold TH1, the first time period t1, and the second time period t2.

In this example, two positions in the waist region are touched, and then the preliminary movement/command input movement determining unit 8h determines whether or not both the outputs of the first pressure sensor and the second pressure sensor that detect the touches are a certain threshold (the first threshold TH1 in FIG. 27) or more (see parts (a) and (b) of FIG. 27) and match the preliminary movement pattern stored in the storage unit 8a (a signal pattern defined by the order of touched positions or time interval between the touches). If it is determined through the determination that a preliminary movement has been input, that is detected as a third contact. For example, if the preliminary movement/command input movement determining unit 8h determines that the output of the first pressure sensor is smaller than the certain threshold (the first threshold TH1 in FIG. 27, see part (c) of FIG. 27), that is not detected as a third contact.

If the preliminary movement/command input movement determining unit 8h determines, within a certain time period (the first time period t1 in FIG. 27) after the preliminary movement has been input (see part (b) of FIG. 27), that an output of the fifth pressure sensor (corresponding to the first contact sensor) is a certain threshold (the first threshold TH1 in FIG. 27) or more (see part (d) of FIG. 27), the preliminary movement/command input movement determining unit 8h determines that a first contact has been detected. After that, within a certain time period (the second time period t2) from the detection of the first contact, if a swipe movement is performed in the direction from the fifth pressure sensor toward the third pressure sensor (corresponding to the second contact sensor) and if outputs of a certain threshold (the first threshold TH1) or more (see parts (e) and (f) of FIG. 27) from the fourth pressure sensor (corresponding to at least one contact sensor between the first contact sensor and the second contact sensor) and the third pressure sensor are sequentially detected, the preliminary movement/command input movement determining unit 8h determines that a command has been input, which is detected as an intermediate contact. At this time, the number of pressure sensors that have detected the intermediate contact is counted, a control amount of assist power is set in accordance with the total number of contact detections counted in the second time period t2 from the detection of the first contact, and information representing the control amount is transmitted to the determining unit 8c. Note that, among contacts detected as an intermediate contact within the second time period t2, the last detected contact is the second contact. In FIG. 27, the total number of intermediate contacts and second contacts that have been detected is two.

Figure 28:
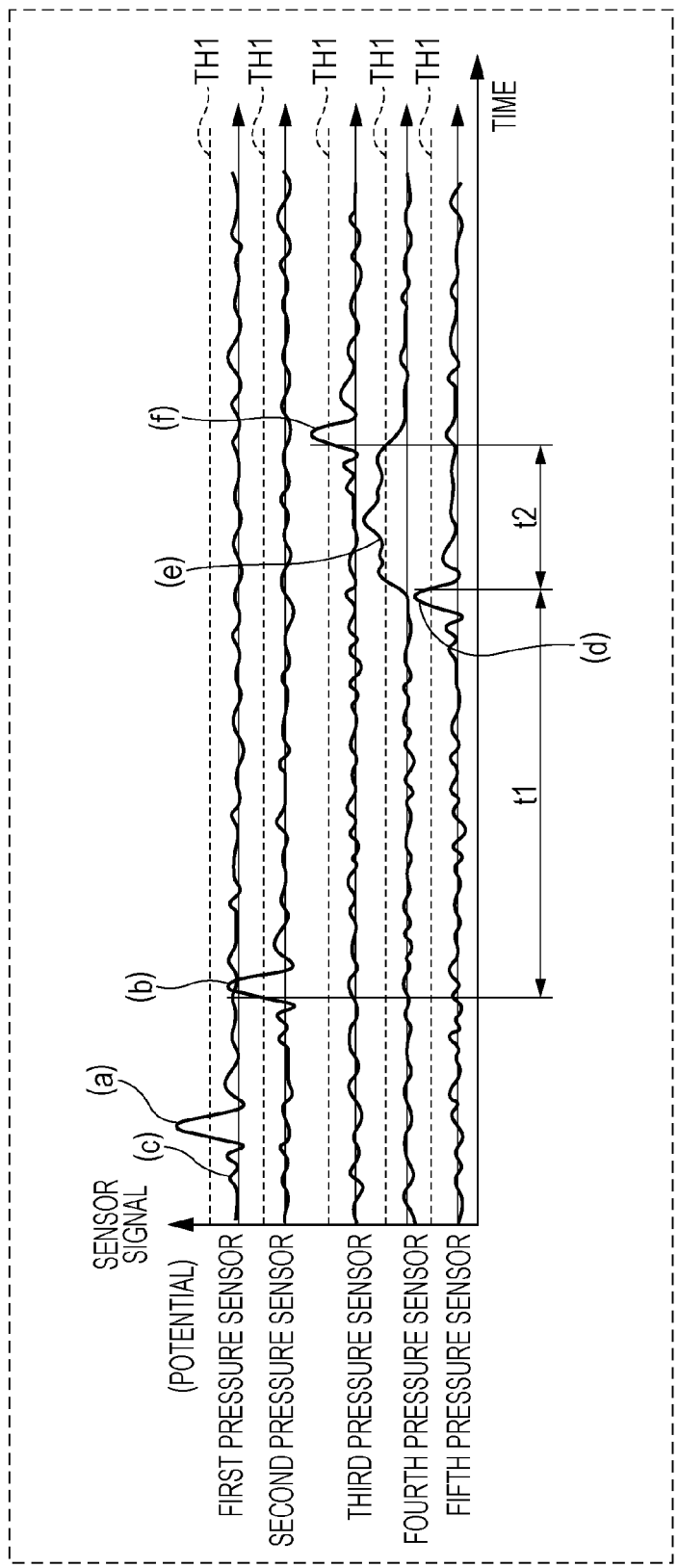
FIG. 28 is a graph for describing another example of a relationship among sensor signals which are outputs from five pressure sensors, a first threshold, and a first time period.

FIG. 27 illustrates a case where the second time period t2 is short. FIG. 28 illustrates a case where the second time period t2 is longer than that in FIG. 27 and where there are a plurality of waveforms in which an output of the fourth pressure sensor is a certain threshold (the first threshold TH1) or more (see (e) of FIG. 27).

Here, each of the first time period t1 and the second time period t2 may be, for example, about 3 seconds. If the time periods are longer, an incorrect input may occur due to an unintended contact by the user 1.

Figure 30:
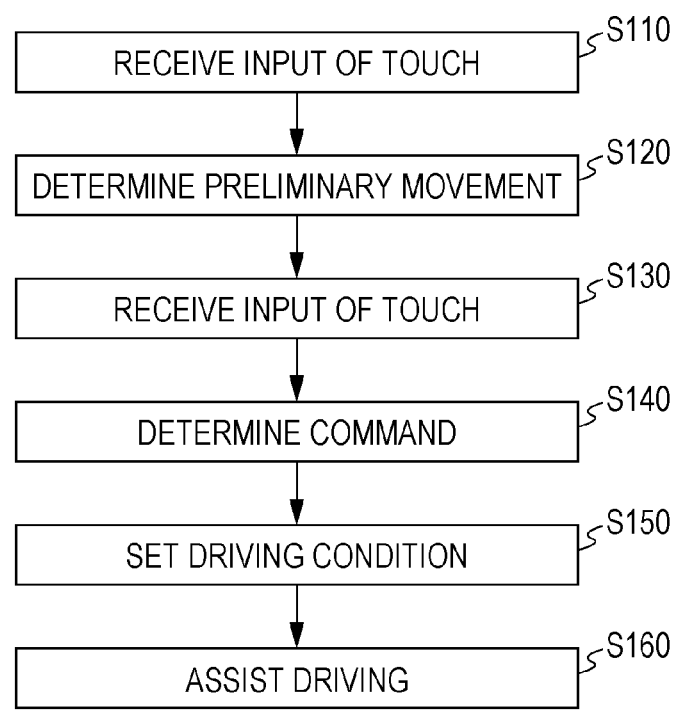
FIG. 30 is a flowchart illustrating processing of determination of a preliminary movement and a command input movement, and assist driving performed by a preliminary movement/command input movement determining unit and a driving unit.
Figure 31:
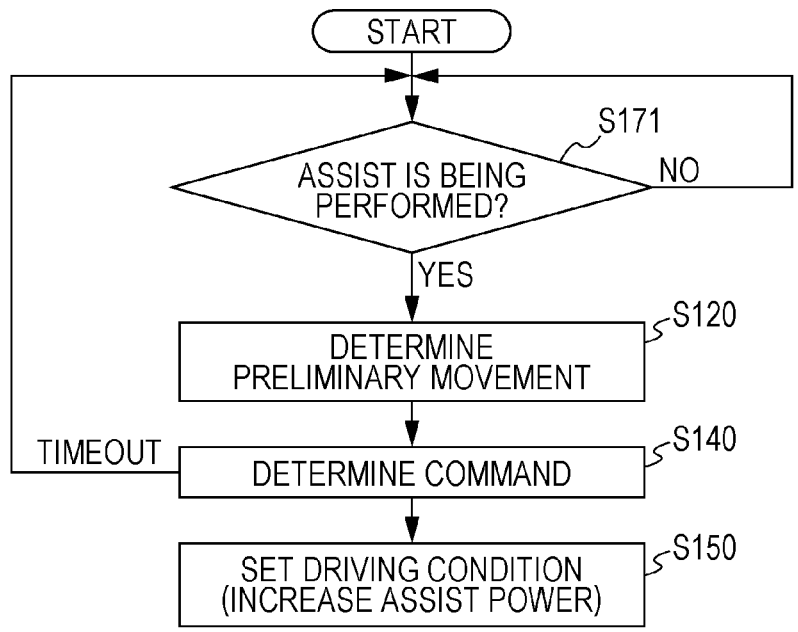
FIG. 31 is a flowchart illustrating processing performed by the preliminary movement/command input movement determining unit.
Figure 32:
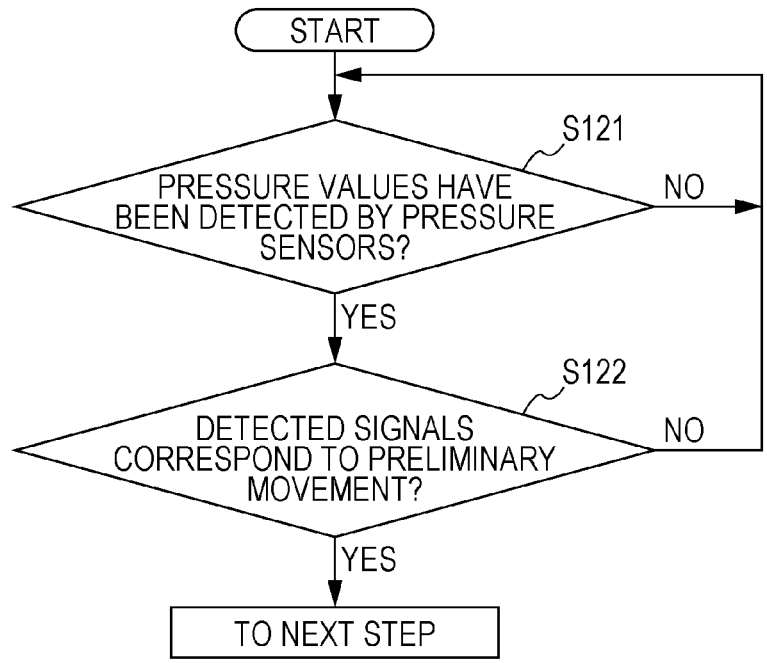
FIG. 32 is a flowchart illustrating processing for a preliminary movement in the processing performed by the preliminary movement/command input movement determining unit.
Figure 33A:
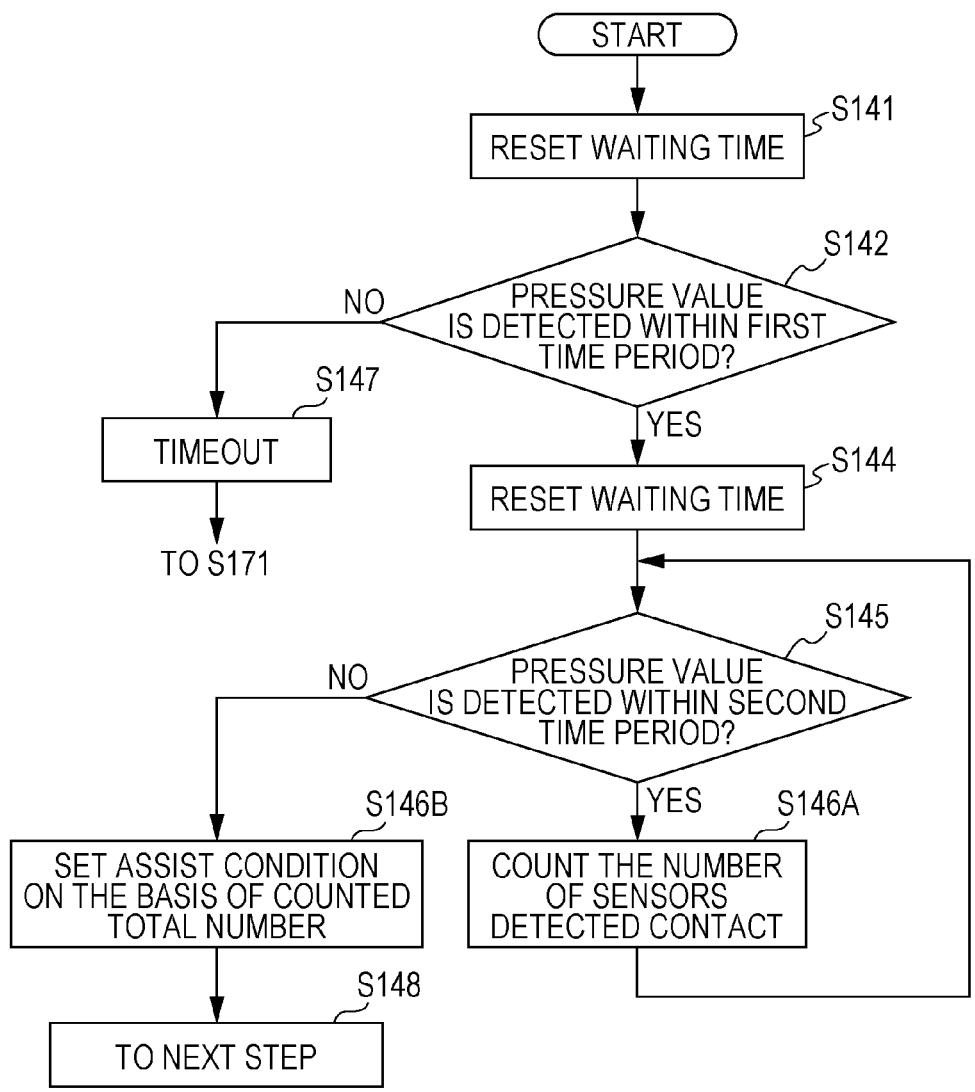
FIG. 33A is a flowchart illustrating processing for a command input movement in the processing performed by the preliminary movement/command input movement determining unit.

FIG. 30 illustrates processing of preliminary movement/command input movement determination and assist driving, which is performed by the preliminary movement/command input movement determining unit 8h and the driving unit 8d. FIG. 31 illustrates processing performed by the preliminary movement/command input movement determining unit 8h. FIG. 32 illustrates processing for a preliminary movement in the processing performed by the preliminary movement/command input movement determining unit 8h. FIG. 33A illustrates processing for a command input movement in the processing performed by the preliminary movement/command input movement determining unit 8h.

First, FIG. 30 will be described.

In step S110, the user 1 inputs a touch, and accordingly sensor signals are output from the pressure sensors 87.

Subsequently, in step S120, the preliminary movement/command input movement determining unit 8h determines whether or not the output of a pressure sensor 87a (pressure value (sensor signal)) obtained in step S110 is a certain threshold or more and whether or not the signal pattern matches the information stored in the storage unit 8a. The processing proceeds to the next step only if the output of the pressure sensor 87*a* (pressure value (sensor signal)) and the signal pattern represent a preliminary movement.

Subsequently, in step S130, the user performs swipe input, and accordingly a sensor signal is output from a pressure sensor 87*b*.

Subsequently, in step S140, the preliminary movement/command input movement determining unit 8*h* determines whether or not the output of the pressure sensor 87*b* (a first pressure value (sensor signal)) obtained in step S130 corresponds to a command input movement. The processing proceeds to the next step only if the output of the pressure sensor 87*b* (the first pressure value (sensor signal)) represents a command.

Subsequently, in step S150, the preliminary movement/command input movement determining unit 8*h* sets a driving condition on the basis of the information stored in the storage unit 8*a* and determination result information.

Subsequently, in step S160, the driving condition is output from the preliminary movement/command input movement determining unit 8*h* to the driving unit 8*d* via the determining unit 8*c* and the actuator selecting unit 8*e*, and the driving unit 8*d* drives the assisting actuators 6 on the basis of the driving condition. As a result, an increase or decrease in the assist power, that is, the driving power of expansion/contraction driving of the assisting actuators 6, is adjusted.

Next, processing performed by the preliminary movement/command input movement determining unit 8*h* will be described with reference to FIG. 31.

In step S171, the preliminary movement/command input movement determining unit 8*h* determines, on the basis of a signal that is input from the driving unit 8*d* and indicates whether or not the assisting actuators 6 are being driven, whether or not assist is being performed by the assisting actuators 6. If assist is being performed, the processing proceeds to step S120. If assist is not being performed, a waiting state continues until assist starts.

In step S120, the preliminary movement/command input movement determining unit 8*h* performs determination of a preliminary movement. The processing proceeds to step S140 only if the preliminary movement/command input movement determining unit 8*h* determines that a preliminary movement has been performed.

In step S140, the preliminary movement/command input movement determining unit 8*h* performs a command determination operation of determining whether or not a command input movement has been performed within a certain time period. The processing proceeds to step S150 only if the preliminary movement/command input movement determining unit 8*h* determines that a command input movement has been performed within the certain time period. If the preliminary movement/command input movement determining unit 8*h* determines that a command input movement has not been performed within the certain time period, the processing returns to step S171.

In step S150, as described above, the preliminary movement/command input movement determining unit 8*h* sets a driving condition on the basis of the information stored in the storage unit 8*a* and the determination result information.

Next, processing for a preliminary movement performed by the preliminary movement/command input movement determining unit 8*h* will be described with reference to FIG. 32.

In step S121, it is determined whether or not the pressure values (sensor signals) output from two pressure sensors 87*a* in step S110 have been received and detected by the preliminary movement/command input movement determining unit 8*h*. If the pressure values have not been detected, a waiting state continues until they are detected. If the pressure values (sensor signals) output from the two pressure sensors 87*a* have been received and detected by the preliminary movement/command input movement determining unit 8*h*, the processing proceeds to step S122.

Subsequently, in step S122, the preliminary movement/command input movement determining unit 8*h* determines whether or not each of the pressure values (sensor signals) output from the two pressure sensors 87*a* in step S110 is the first threshold TH1 or more and whether or not the signal pattern matches the information stored in the storage unit 8*a*. If it is determined that the detected signals correspond to a preliminary movement, the detection result indicating the two pressure values is received as a detection result indicating a third contact, and the processing proceeds to step S130. If the preliminary movement/command input movement determining unit 8*h* determines that either of the pressure values detected by the two pressure sensors 87*a* is smaller than the first threshold TH1 or that the detected signal pattern does not match the preliminary movement (see part (c) of FIG. 27), the processing returns to step S121.

The comparison with the signal pattern of the preliminary movement is not always necessary. Determination of the preliminary movement may be performed by using only the threshold.

Here, determination of the preliminary movement is performed by using two pressure sensors 87*a*, but the embodiment is not limited thereto. Determination of the preliminary movement may be performed by using one pressure sensor 87*a* or three or more pressure sensors 87*a*. Also, determination of the preliminary movement may be performed by using a pressure sensor 87 that is used for both a preliminary movement and a command input movement.

Next, processing for a command input movement performed by the preliminary movement/command input movement determining unit 8*h* will be described with reference to FIG. 33A.

In step S141, the waiting time is reset after determination of the preliminary movement in step S120, and measurement of the first time period t1 is started.

Subsequently, in step S142, if the preliminary movement/command input movement determining unit 8*h* determines that the pressure value of the pressure sensor 87 (see the fifth sensor in FIG. 27) that detects a pressure value the earliest among the plurality of pressure sensors 87 that output pressure values in step S130 is equal to or larger than the first threshold TH1 within the first time period t1 (see part (d) of FIG. 27), the detection result indicating the pressure value is received as a detection result indicating a first contact (it is determined that a command input movement has been performed), and the processing proceeds to step S144. If a pressure value equal to or larger than the first threshold TH1 is not detected within the first time period t1, the processing returns to step S171 (see step S147).

Subsequently, in step S144, the waiting time is reset and measurement of the second time period t2 is started.

Subsequently, in step S145, if the preliminary movement/command input movement determining unit 8*h* determines that each of the pressure values output from the pressure sensors 87*b* (see the fourth and third sensors in FIG. 27) in response to the swipe movement (swipe input) in step S130 is equal to or larger than the first threshold TH1 within the second time period t2 (see parts (e) and (f) of FIG. 27), the detection result indicating the pressure values is received as a detection result indicating an intermediate contact and a second contact (it is determined that a command input movement has been performed), and the processing proceeds to step S146A. If the preliminary movement/command input movement determining unit 8h determines that each of the pressure values detected by the pressure sensors 87b is smaller than the first threshold TH1, the processing proceeds to step S146B. Also, after the second time period t2 has elapsed, the processing proceeds to step S146B.

In step S146A, the preliminary movement/command input movement determining unit 8h counts the number of pressure sensors 87 that have detected the intermediate contact and the second contact (determined that a command input movement has been performed). In the example illustrated in FIG. 27, the number of pressure sensors 87 is two (the fourth and third sensors). After that, the processing returns to step S145.

In step S146B, on the basis of a value calculated by adding one, which is the number of pressure sensors 87 that have performed detection in step S142 to the number of pressure sensors 87 counted so far (zero if the number is not counted), the preliminary movement/command input movement determining unit 8h performs control so as to increase the driving power of expansion/contraction driving of the assisting actuators 6, or, if the number is zero, the driving power at the time is maintained (see FIG. 34A described below). After that, the processing proceeds to step S148.

In step S148, the preliminary movement/command input movement determining unit 8h transmits a signal for increasing the driving power to the determining unit 8c on the basis of the information obtained so far.

In this example, setting information is updated to increase the driving power of expansion/contraction driving of the assisting actuators 6 in accordance with the number of pressure sensors 87 that have detected an intermediate contact and a second contact (determined that a command input movement has been performed), but the embodiment is not limited thereto. For example, on the basis of position information about the pressure sensors 87 that have detected the intermediate contact and the second contact (determined that a command input movement has been performed), the maximum distance between two pressure sensors 87 among the pressure sensors 87 (the distance over which a swipe movement is performed) may be calculated, and the setting information may be updated to increase the driving power of expansion/contraction driving of the assisting actuators 6 on the basis of the distance.

Figure 33B:
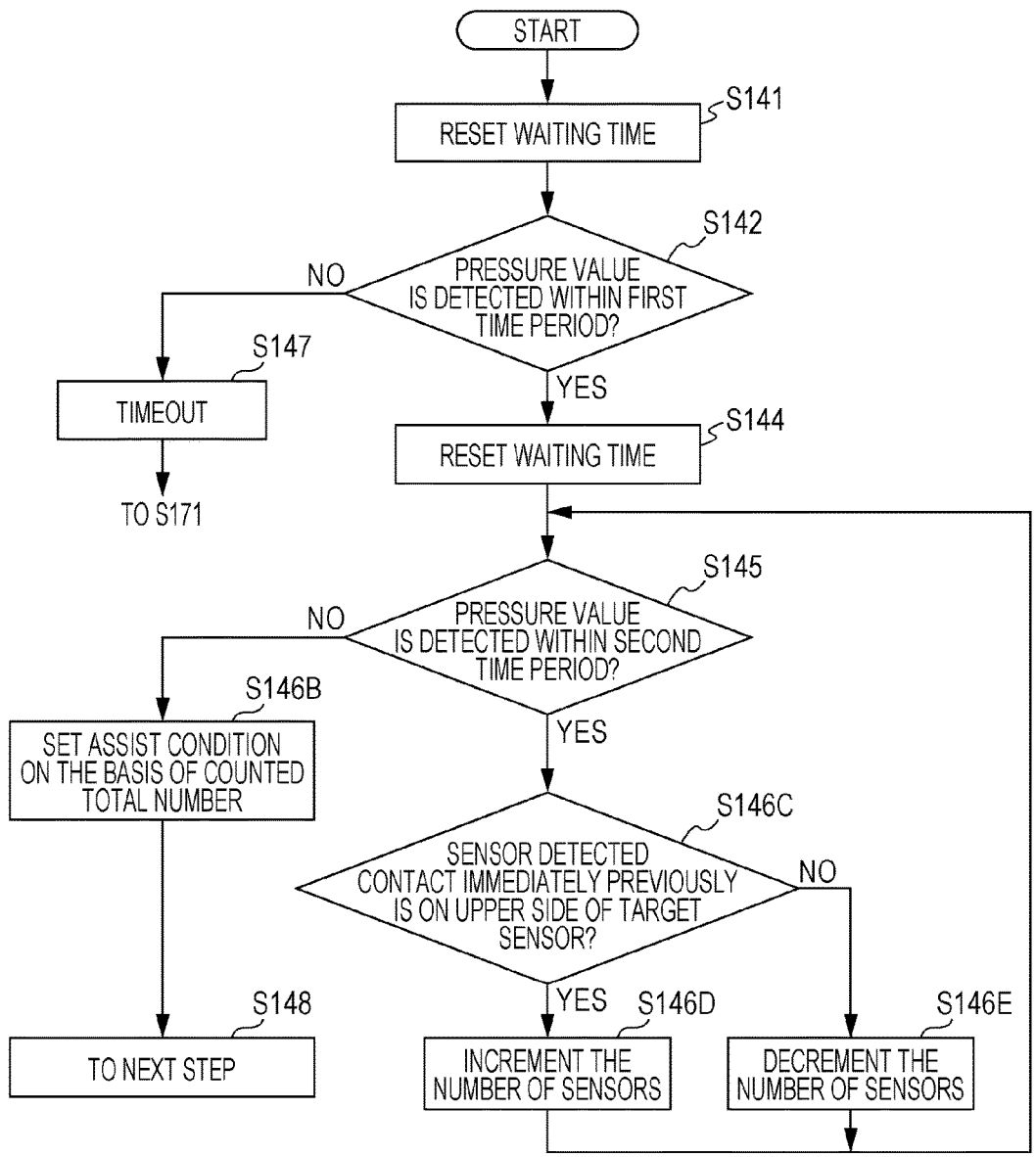
FIG. 33B is a flowchart illustrating processing of a command determination operation according to a modification example in the processing performed by the preliminary movement/command input movement determining unit.
Figure 33C:
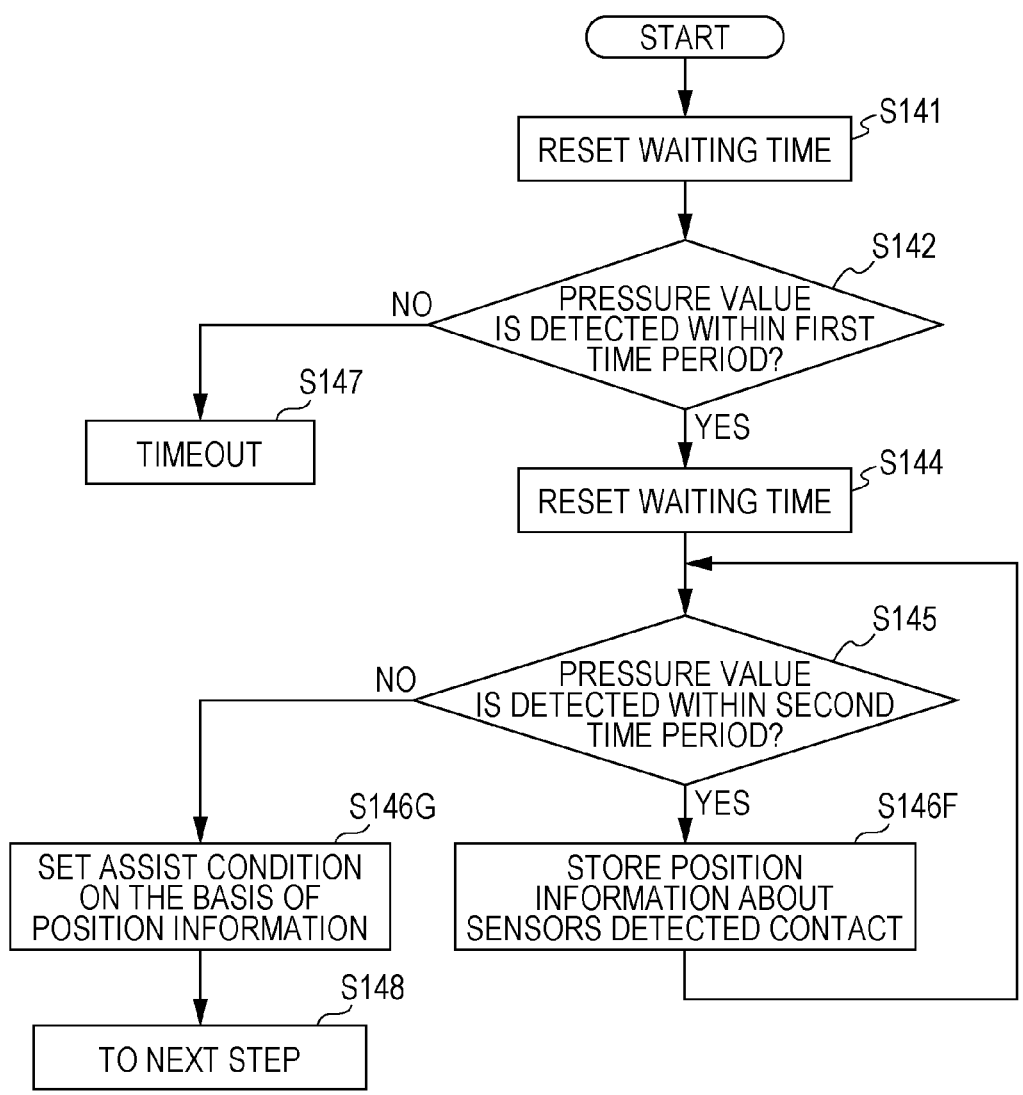
FIG. 33C is a flowchart illustrating processing of a command determination operation according to another example in the processing performed by the preliminary movement/command input movement determining unit.

An example of this is illustrated in FIG. 33C. Steps S141, S142, S147, S144, S145, and S148 are the same as those in FIG. 33A.

In step S145 in FIG. 33C, if the preliminary movement/command input movement determining unit 8h determines that each of the pressure values output from the two pressure sensors 87 (see the fourth and third sensors in FIG. 27) in response to the swipe movement in step S130 is equal to or larger than the first threshold TH1 within the second time period t2 (see parts (e) and (f) of FIG. 27), the detection result indicating the two pressure values is received as a detection result indicating an intermediate contact and a second contact (it is determined that a command input movement has been performed), and the processing proceeds to step S146F. Otherwise, the processing proceeds to step S146G.

In step S146F, position information about the pressure sensors 87 that have detected the intermediate contact and the second contact (determined that a command input movement has been performed) is temporarily stored, and the processing returns to step S145.

In step S146G, a combination of two pressure sensors 87 having a maximum distance therebetween is calculated by using the position information about the pressure sensors 87 stored so far. On the basis of the information about the maximum distance, the preliminary movement/command input movement determining unit 8h updates the setting information to increase the driving power of expansion/contraction driving of the assisting actuators 6, and the processing proceeds to step S148.

A more specific example is illustrated in FIG. 34B. FIG. 34B is an explanatory diagram in the form of a table illustrating the relationship between distances and set values of assist power in the case of increasing the assist power of the assisting actuators 6 in proportion to a maximum distance L (a distance over which a swipe movement is performed), which is calculated on the basis of the position information about the pressure sensors 87 that have detected an intermediate contact and a second contact. FIG. 34B indicates that, if the maximum distance L between two pressure sensors 87 among the pressure sensors 87 that have detected the intermediate contact and the second contact is expressed by 0 cm<L≤4 cm, the preliminary movement/command input movement determining unit 8h increases the assist power of the assisting actuators 6 by 10%, and that, if the maximum distance L is expressed by 4 cm<L≤8 cm, the preliminary movement/command input movement determining unit 8h increases the assist power of the assisting actuators 6 by 20%.

The preliminary movement/command input movement determining unit 8h or the receiving unit 8f according to the third modification example described below controls driving of the assisting actuators 6 on the basis of information about the number of pressure sensors 87 related to detection of a second contact and detection of an intermediate contact and information about the relationship between the number of pressure sensors 87 and set values of assist power stored in the storage unit 8a (see FIG. 34A, which is a table showing the relationship between the numbers of pressure sensors and set values of assist power). Specifically, the preliminary movement/command input movement determining unit 8h or the command determination controller 88 according to the third modification example described below controls an increase or decrease in the driving power of expansion/contraction driving of the assisting actuators 6 on the basis of the number of pressure sensors 87 related to an intermediate contact and a second contact detected by the pressure sensors 87 after the preliminary movement/command input movement determining unit 8h or the receiving unit 8f has received a detection result indicating a third contact. Specifically, the preliminary movement/command input movement determining unit 8h or the command determination controller 88 controls an increase or decrease in the driving power of expansion/contraction driving of the assisting actuators 6 on the basis of the number of pressure sensors 87 related to detection of an intermediate contact and a second contact having a pressure value which is the first threshold or larger within the second time period t2 after detection by the pressure sensors 87 is started within the first time period t1 after the preliminary movement/command input movement determining unit 8h or the receiving unit 8f receives a detection result indicating a pressure value which is the first threshold TH1 or larger. FIG. 34A is an explanatory diagram in the form of a table showing the relationship between the numbers of pressure sensors and set values of assist power in the case of increasing the assist power of the assisting actuators 6 in proportion to the number of pressure sensors 87 that have detected an intermediate contact and a second contact. In FIG. 34A, if the number of pressure sensors 87 that have detected an intermediate contact and a second contact is one to four, for example, the assist power of the assisting actuators 6 is increased by 10% by the preliminary movement/command input movement determining unit 8h, and, if the number of pressure sensors 87 that have detected an intermediate contact and a second contact is five to eight, the assist power of the assisting actuators 6 is increased by 20% by the preliminary movement/command input movement determining unit 8h.

The assist power may be increased or decreased by taking a swiping direction into consideration. An example of this is illustrated in FIG. 33B. Steps S141, S142, S147, S144, S145, S146B, and S148 are the same as those in FIG. 33A.

In step S145 in FIG. 33B, if the preliminary movement/command input movement determining unit 8h determines that each of the pressure values of two pressure sensors 87 (see the fourth sensor and the third sensor in FIG. 27) output in response to the swipe movement in step S130 is the first threshold TH1 or larger within the second time period t2 (see parts (e) and (f) of FIG. 27), the detection result indicating the two pressure values is received as a detection result indicating an intermediate contact and a second contact (it is determined that a command input movement has been performed), and the processing proceeds to step S146C.

In step S146C, the preliminary movement/command input movement determining unit 8h determines whether or not the sensor that detected a contact immediately previously (the fourth sensor in state (e) of FIG. 27) is on the upper side of the target sensor (the third sensor in state (f) of FIG. 27).

If the preliminary movement/command input movement determining unit 8h determines in step S146C that the sensor that detected a contact immediately previously is on the upper side of the target sensor, the preliminary movement/command input movement determining unit 8h increments the number of sensors related to the detection of a contact by one (step S146D). After that, the processing returns to step S145.

If the preliminary movement/command input movement determining unit 8h determines in step S146C that the sensor that detected a contact immediately previously is not on the upper side of the target sensor, the preliminary movement/command input movement determining unit 8h decrements the number of sensors related to the detection of a contact by one (step S146E). After that, the processing returns to step S145.

In this way, the driving power of expansion/contraction driving of the assisting actuators 6 can be easily increased or decreased in accordance with a swiping direction.

Here, as an example, the assist power is increased by a certain amount if a command input movement is performed. The method for adjusting the assist power is not limited thereto.

As an example of controlling an increase or decrease in the driving power of expansion/contraction driving of the assisting actuators 6, the preliminary movement/command input movement determining unit 8h is capable of increasing the assist power of the assisting actuators 6 in proportion to the number of pressure sensors 87 that have detected an intermediate contact and a second contact. In this way, the assist power is increased in proportion to the number of pressure sensors 87 that have detected the intermediate contact and the second contact, and thus, if the user 1 wants to increase the assist power, the user 1 only has to touch the wear main body 2 until a desired assist power is obtained, and thus an increase or decrease in the driving power of the expansion/contraction driving of the assisting actuators 6 can be adjusted more easily.

Finally, the method for avoiding incorrect input of a command according to the embodiment will be described. First, in the already described method, a detection result indicating a third contact is received only during expansion/contraction driving of the assisting actuators 6. Only in a case where the user 1 wants to fine-tune the assist power, the user 1 is allowed to perform a touch input or swipe input. In determination of a preliminary movement or a command input movement, a threshold which is equal to or larger than a pressure value that is detected in response to an unintended touch is set and a pressure value is detected. Further, the preliminary movement is formed of a plurality of touches, which is a movement that is less likely to be performed accidentally.

If a contact is detected within a certain time period after a third contact as a preliminary movement is detected, the contact is determined to be command input, which is regarded as detection of a first contact. If the third contact is a contact that is not intended by the user 1, there is a low possibility that a first contact as the next contact is performed within the first time period t1. That is, if the user 1 wants to change (increase or decrease) the driving power of expansion/contraction driving of the assisting actuators 6, it is natural that the time interval between the third contact and the first contact is short to some extent. Thus, in the embodiment, it is determined that a command input has been performed only in a case where a first contact is detected within the first time period t1 from the time point when a third contact is detected. Accordingly, the driving power of expansion/contraction driving of the assisting actuators 6 is not changed (increased or decreased) by a first contact that is not detected within the first time period t1. Further, it can be determined whether or not a third contact is a contact intended by the user 1.

In a command input movement, only in a case where a detection result indicating an intermediate contact is received from at least one contact sensor arranged between the first contact sensor and the second contact sensor in the entire time period (second time period t2) after a detection result indicating a first contact is received from the first contact sensor until a detection result indicating a second contact is received from the second contact sensor, the detection result is received as a control instruction for the driving power of expansion/contraction driving of the assisting actuators 6, and an increase or decrease in the assist power is controlled. Even if the user 1 has finished input of a command, the driving power of expansion/contraction driving of the assisting actuators 6 may be changed (increased or decreased) if the assist wear item 4 receives some contact not intended by the user 1. However, in this embodiment, command input starts at the moment when a first contact is detected, and reception of the command input is finished at the moment when the user 1 takes his/her hand off the assist wear item 4 even if the second time period t2 has not elapsed. Thus, even if the second time period t2 is set to be relatively long, there is a low possibility that command input not intended by the user 1 is received.

Advantages

According to the above-described embodiment, the following advantages can be obtained.

In a configuration in which a dedicated terminal (the information terminal 15 or the input/output device 16) is used to increase or decrease the driving power of expansion/contraction driving of the assisting actuators 6, it is necessary to operate the terminal to specify the part where the driving power is to be increased or decreased and input an amount of increase or decrease of the driving power every time the driving power is to be increased or decreased, which is inconvenient.

According to the above-described embodiment, in a case where a detection result indicating an intermediate contact is continuously received from at least one contact sensor arranged between the first contact sensor and the second contact sensor in the entire time period after a detection result indicating a first contact is received from the first contact sensor until a detection result indicating a second contact is received from the second contact sensor (the entire time period until reception of a detection result indicating the second contact ends), the driving power of expansion/contraction driving of the assisting actuators 6 corresponding to the region ranging from the first contact sensor to the second contact sensor among the plurality of assisting actuators 6 is increased or decreased.

Accordingly, the user 1 who is wearing the assist wear item 4 is able to increase or decrease the driving power of expansion/contraction driving of the assisting actuators 6 only by swiping the assist wear item 4 at the position where the driving power of the assisting actuators 6 is to be increased or decreased, that is, without using a dedicated terminal.

First Modification Example

The controller 8 may control an increase or decrease in the driving power of expansion/contraction driving of the assisting actuators 6 by changing the expansion/contraction length of the assisting actuators 6. That is, for example, in the case of increasing the driving power, the expansion/contraction length of the assisting actuators 6 may be increased. On the other hand, in the case of decreasing the driving power, the expansion/contraction length of the assisting actuators 6 may be decreased.

Alternatively, the controller 8 may control an increase or decrease in the driving power of the expansion/contraction driving of the assisting actuators 6 by changing the spring constant of the assisting actuators 6. That is, for example, in the case of increasing the driving power, the spring constant of the assisting actuators 6 may be increased. On the other hand, in the case of decreasing the driving power, the spring constant of the assisting actuators 6 may be decreased.

Second Modification Example

The first threshold TH1 may be automatically increased when the movement of a muscle of the user 1 is large. In many cases, a pressure value detected when the user 1 is moving hard is larger than a pressure value detected when the user 1 is not moving hard. For example, it is assumed that a pressure value detected when a hand of the user 1 who is running touches the wear main body 2 is larger than a pressure value detected when a hand of the user 1 who is walking touches the wear main body 2. In this case, if the first threshold TH1 is a specific fixed value, the touch may be detected or not detected as a third contact depending on the degree of movement of the user 1.

To avoid such variations, the controller 8 may increase the first threshold TH1 when the amount of change in the expansion/contraction length of the assisting actuators 6 per certain time period is a certain threshold or larger. Such a second modification example will be described in detail below.

Figures 35, 36:
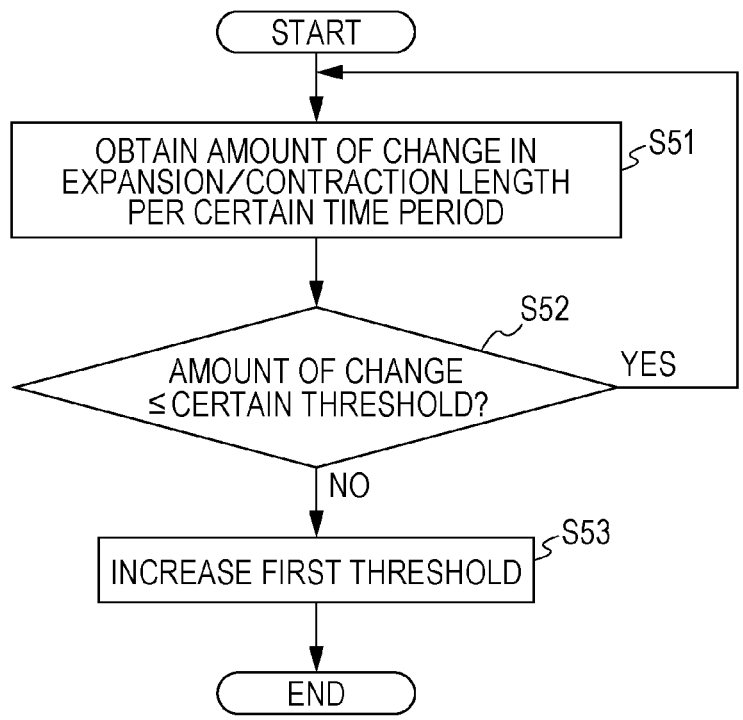
FIG. 35 is a flowchart of processing performed by the preliminary movement/command input movement determining unit or a receiving unit according to a second modification example.
FIG. 36 illustrates, in the form of a table, new thresholds set for amounts of change in an expansion/contraction length of assisting actuators.

FIG. 35 is a flowchart of processing in the preliminary movement/command input movement determining unit 8h or the receiving unit 8f according to the second modification example. FIG. 36 illustrates, in the form of a table, new thresholds set for the amounts of change in the expansion/contraction length of the assisting actuators 6. This piece of information is stored in the storage unit 8a.

Here, as in FIG. 37 described below, the pressure sensors 87, the driving unit 8d, and the storage unit 8a are connected to the preliminary movement/command input movement determining unit 8h or the receiving unit 8f. Information representing the amount of change in the expansion/contraction length of the assisting actuators 6 is input from the driving unit 8d to the preliminary movement/command input movement determining unit 8h or the receiving unit 8f.

In a case where the amount of change in the expansion/contraction length of the assisting actuators 6 per certain time period is equal to or larger than the fifth threshold TH5 stored in the storage unit 8a, it is estimated that the assisting actuators 6 are operating hard, and thus the preliminary movement/command input movement determining unit 8h or the receiving unit 8f sets the first threshold TH1 for determination of a preliminary movement to be increased. Specifically, the preliminary movement/command input movement determining unit 8h or the receiving unit 8f performs the following processing.

First, in step S51 in FIG. 35, the preliminary movement/command input movement determining unit 8h or the receiving unit 8f obtains an amount of change in the expansion/contraction length of the assisting actuators 6 per certain time period.

Subsequently, in step S52, the preliminary movement/command input movement determining unit 8h or the receiving unit 8f determines whether or not the obtained amount of change in the expansion/contraction length of the assisting actuators 6 per certain time period is equal to or smaller than a certain threshold (the fifth threshold TH5). If the preliminary movement/command input movement determining unit 8h or the receiving unit 8f determines that the amount of change in the expansion/contraction length of the assisting actuators 6 is larger than the fifth threshold TH5, it is estimated that the assisting actuators 6 are operating hard, and the processing proceeds to step S53. If the preliminary movement/command input movement determining unit 8h or the receiving unit 8f determines that the amount of change in the expansion/contraction length of the assisting actuators 6 is equal to or smaller than the fifth threshold TH5, it is estimated that the assisting actuators 6 are not operating hard, and the processing returns to step S51.

In step S53, the preliminary movement/command input movement determining unit 8h or the receiving unit 8f sets the first threshold TH1 to a larger value on the basis of the table stored in the storage unit 8a and the obtained amount of change in the expansion/contraction length. An example of the table stored in the storage unit 8a is illustrated in FIG. 36. In FIG. 36, new thresholds for obtained amounts of change in the expansion/contraction length are stored. In FIG. 36, "A" represents a value of the first threshold TH1 that is initially set. It means that the value A of the first threshold TH1 is not increased when the amount of change is 10% or less, and that the value A of the first threshold TH1 is increased 1.5 times when the amount of change is larger than 10%.

According to the second modification example, the value of the first threshold TH1 is increased when the amount of change per certain time period in the voltage value generated when a muscle is moved is a certain threshold (the fifth threshold TH5) or larger, that is, when the user 1 is moving hard. Accordingly, even when the user is moving hard, an increase or decrease in the driving power of expansion/contraction driving of the assisting actuators 6 that is not intended by the user 1 can be effectively prevented.

Third Modification Example

Figure 37:
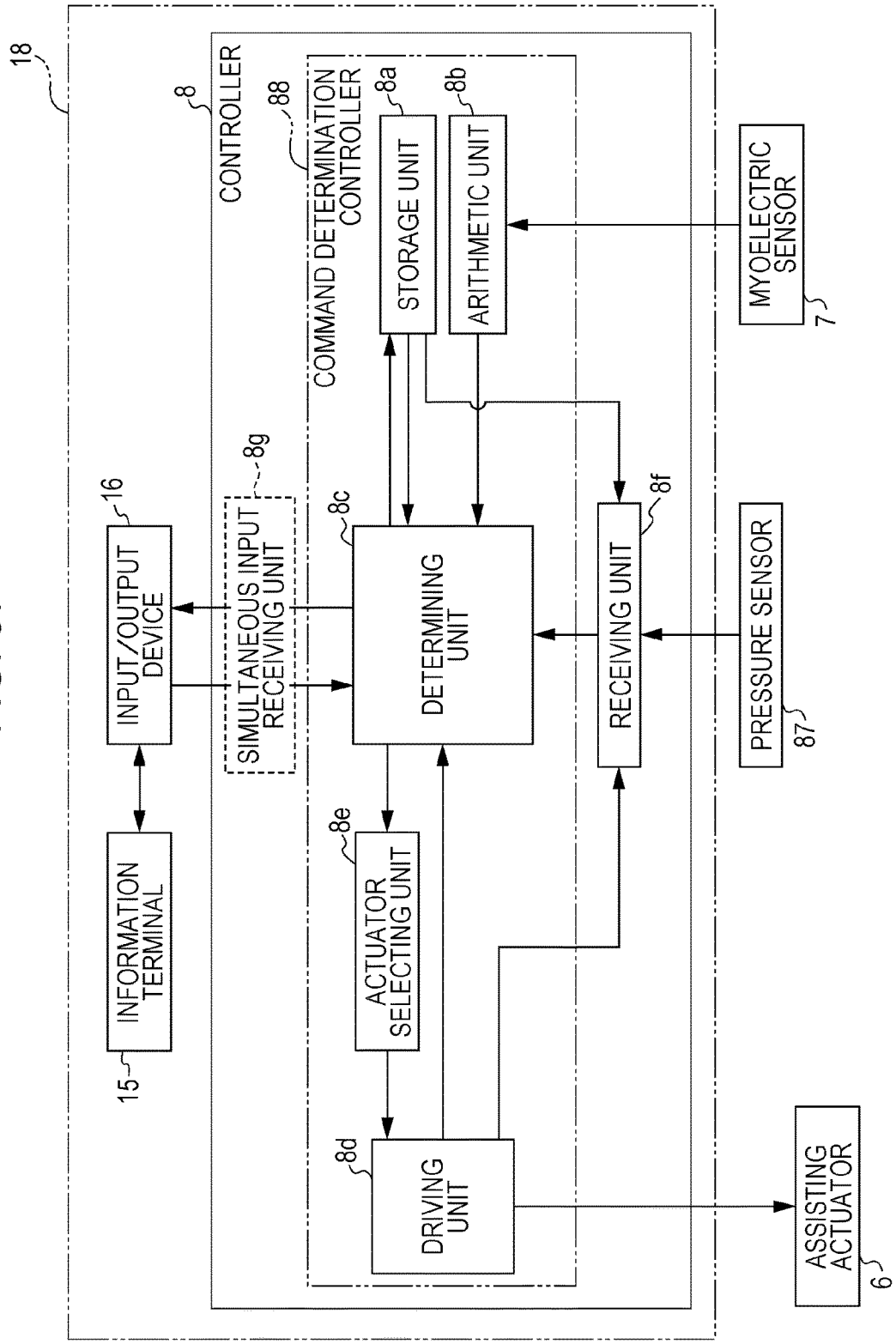
FIG. 37 is a block diagram related to an assist wear item according to a third modification example.

FIG. 37 is a block diagram related to an assist wear item 4 according to a third modification example. The difference from the block diagram in FIG. 4A is that the controller 8 is separated into the receiving unit 8f for determination of a preliminary movement (reception operation) and the command determination controller 88 for determination of a command input movement. Other than this point, the configuration and operation of the components illustrated in FIG. 37 are the same as those in FIG. 4A.

As illustrated in FIG. 37, the controller 8 includes the receiving unit 8f and the command determination controller 88. The command determination controller 88 includes the storage unit 8a, the arithmetic unit 8b, the determining unit 8c, the actuator selecting unit 8e, and the driving unit 8d.

The receiving unit 8f is capable of receiving outputs from all the pressure sensors 87, and determines, on the basis of the outputs from the pressure sensors 87, whether or not a third contact as a reception operation has been detected by the pressure sensors 87 and whether or not a second contact and an intermediate contact as an assist power adjustment operation have been detected by the pressure sensors 87. In the determination of whether or not the second contact and the intermediate contact have been detected, if it is determined that the second contact and the intermediate contact have been detected, the receiving unit 8f also determines the number of sensors that have detected the second contact and the intermediate contact. The determination of whether or not the second contact and the intermediate contact have been detected and determination of the number of sensors may be performed by the command determination controller 88, instead of the receiving unit 8f.

More specifically, the receiving unit 8f receives, as a reception operation, a detection result indicating a third contact by a plurality of pressure sensors 87 while the assisting actuators 6 are driven to expand and contract by the driving unit 8d of the command determination controller 88. While the assisting actuators 6 are driven to expand and contract actually means a period in which the assisting actuators 6 are driven to expand and contract or a period after a drive start signal for the assisting actuators 6 has been input. Specifically, when the drive start signal for the assisting actuators 6 is input from the driving unit 8d to the receiving unit 8f, the receiving unit 8f is able to determine that the assisting actuators 6 are being driven to expand and contract.

The reception period is limited in this way for the following reason.

A case where the user 1 wants to change (increase or decrease) the driving power of expansion/contraction driving of the assisting actuators 6 is, in many cases, a case where the user 1 wants to fine-tune the driving power of the expansion/contraction driving of the assisting actuators 6 when receiving assist power from the assist wear item 4. In other words, the user 1 is less likely to want to change (increase or decrease) the driving power of expansion/contraction driving of the assisting actuators 6 when not receiving assist power from the assist wear item 4.

Thus, a setting is made so that a detection result indicating a third contact can be received while the assisting actuators 6 are being driven to expand and contract, that is, while the user 1 is receiving assist power from the assist wear item 4. Accordingly, a detection result indicating a third contact is received while the user 1 is receiving assist power from the assist wear item 4, when the user 1 wants to fine-tune the assist power. As a result, in a situation where the user 1 is less likely to want to change (increase or decrease) the driving power of expansion/contraction driving of the assisting actuators 6, reception of a detection result indicating a third contact is prevented, and accordingly change (increase or decrease) in the driving power of expansion/contraction driving of the assisting actuators 6 not intended by the user 1 can be prevented.

Whether a detection result is a detection result indicating a third contact as a preliminary movement and whether a detection result is a detection result indicating a second contact and an intermediate contact as an assist power adjustment operation is determined by determining whether the movement of the user 1 is a movement that is not accidentally performed. For example, when the user 1 taps a portion of the wear main body 2 once, that movement may be determined as both an accidental light touch of a hand of the user 1 and an intended tap movement as a reception operation.

Thus, for example, if the first threshold TH1 for determination of a preliminary movement and the first threshold TH1 for determination of a command input movement are set to values equal to or larger than a pressure value that is detected in response to an unintended touch, change (increase or decrease) in the driving power of expansion/contraction driving of the assisting actuators 6 not intended by the user 1 can be prevented.

Fourth Modification Example

Figure 41:
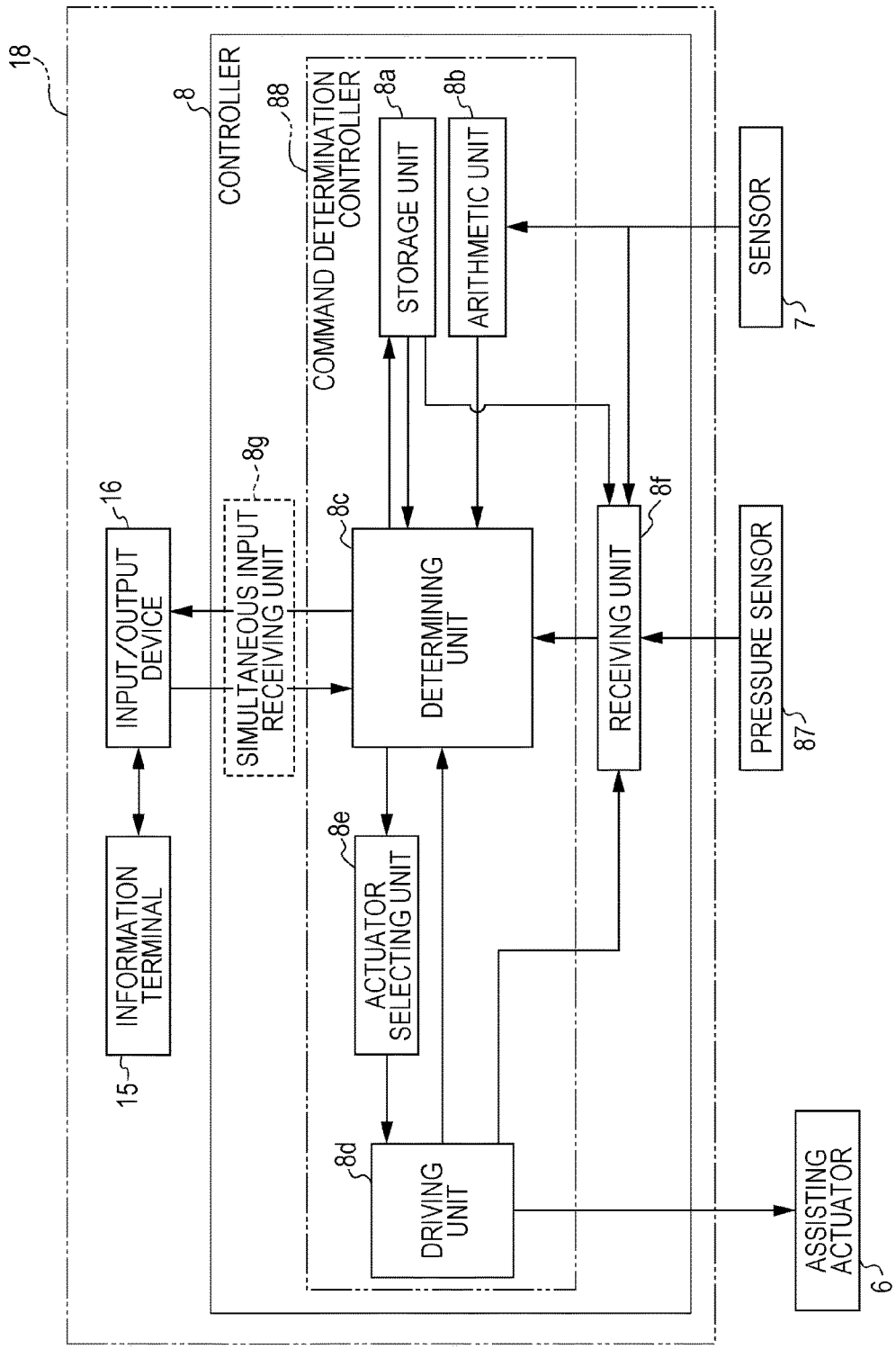
FIG. 41 is a block diagram related to an assist wear item according to a fourth modification example.

FIG. 41 is a block diagram related to an assist wear item 4 according to a fourth modification example. The difference from the block diagram in FIG. 37 is that a sensor 7 is provided instead of the myoelectric sensor 7 and that an output from the sensor 7 can be transmitted to the receiving unit 8f. The sensor 7 may be a myoelectric sensor, a distortion sensor, a gyro sensor, or an acceleration sensor. The assist wear item 4 may include both a myoelectric sensor and a distortion sensor, both a myoelectric sensor and a gyro sensor, or both a myoelectric sensor and an acceleration sensor. In FIG. 37, 7 denotes a myoelectric sensor. On the other hand, in FIG. 41, 7 denotes a sensor, not a myoelectric sensor.

The receiving unit 8f is configured to be able to detect a posture of a target portion to be assisted by using sensors, such as gyro sensors, selects a pressure sensor 87 on the basis of the detected posture, and determines, on the basis of an output of the selected pressure sensor 87, whether or not a first contact for starting an assist power adjustment operation has been detected. In the detection of a second contact and an intermediate contact performed thereafter, only the output of the pressure sensor 87 selected based on the detected posture may be used or the outputs of all the pressure sensors 87 may be used. In the case of a periodic movement such as a walking movement, a current posture can be estimated on the basis of change in the waveform by using output of a myoelectric sensor or acceleration sensor alone, and determination can be performed similarly. For example, in the walking movement illustrated in FIG. 25, signal waveforms in the individual states A to G can be obtained from myoelectric sensors or acceleration sensors, and thus a current state can be determined through continuous monitoring. In FIG. 41, the components denoted by the same reference numerals except the receiving unit 8f have the same configuration and function as those described above.

Here, arrangement positions for various postures during an assist operation are assigned to the pressure sensors 87 that detect a first contact. For example, regarding a certain posture, the pressure sensors 87 arranged at positions where the driving power of the actuator is large are associated with that posture.

More specifically, while the assisting actuators 6 are being driven to expand and contract by the driving unit 8d of the command determination controller 88, the receiving unit 8f receives a detection result indicating a third contact from a plurality of pressure sensors 87 as a reception operation. Subsequently, a posture of a target portion to be assisted is detected on the basis of outputs from the sensors 7, outputs of the pressure sensors 87 associated with the detected posture are received by the receiving unit 8f, and it is determined whether or not a first contact has been detected. That is, only when the target portion to be assisted has a specific posture, adjustment of the driving power of the actuators corresponding to the posture can be started. After that, whether or not a second contact and an intermediate contact as an assist power adjustment operation have been detected is determined. During this time, a posture is not necessarily limited.

A description will be given by using the walking assist operation as an example with reference to FIG. 25. After a third contact has been detected, the current state, that is, which of the states A to G in walking, is detected by the sensors 7. For example, if it is configured to adjust the driving power of each actuator after the peak of the driving power, a first contact with the pressure sensors corresponding to the actuators on the front side of the right thigh is received only in the states B to C and the states E to F, a first contact with the pressure sensors corresponding to the actuators on the back side of the right thigh is received only in the states G to A, and determination of the contact is performed. After the first contact has been detected, detection of a second contact and an intermediate contact is performed. The detection of a second contact and an intermediate contact may be performed in any of the states A to G, and outputs of all the pressure sensors 87 can be input. After the first contact has been detected, the second contact may be performed after one period or more of the walking movement.

As described above, a case where the user 1 wants to change (increase or decrease) the driving power of expansion/contraction driving of the assisting actuators 6 is often a case where the user 1 wants to fine-tune the driving power of expansion/contraction driving of the assisting actuators 6 when receiving assist power from the assist wear item 4. At this time, the timing to start input of an amount of adjustment of the driving power may be limited to further reduce incorrect input.

If the detection of a first contact to a second contact is performed only in a section of a certain posture, for example, the section between state B and state C in FIG. 25, incorrect input can be significantly reduced. However, a swipe movement enables fine tuning but takes longer time than a tap movement or the like, and it is difficult to complete an intended input within a specific time period. In this modification example, only the position and timing of a first contact, which is a movement to start adjustment, are limited, and the position and timing of a swipe movement performed thereafter are not limited. Thus, the driving power can be adjusted even if an input operation is performed over one period or more of the periodic movement, and incorrect input can be effectively reduced.

Further, with use of a posture to determine the timing to receive a first contact, a determination can be made while eliminating the influence on the movement speed. For example, in the walking movement illustrated in FIG. 25, control can be performed in which a first contact on the front side of the right thigh is received only in a specific time period from state B or state E. However, if the specific time period is short, it is difficult to perform input. If the specific time period is long, the next peak comes within the specific time period if the walking speed is high. In such a case, there is no effect of reducing incorrect input by limiting the input timing. In this modification example, the input timing is determined on the basis of a posture, and thus incorrect input can be reduced while allowing appropriate input in accordance with the walking speed.

Fifth Modification Example

A plurality of contact sensors are not limited to pressure sensors and may be a plurality of small touch sensors that are arranged on the outer surface of the wear main body 2 and that detect an amount of change in capacitance. The touch sensors according to a fifth modification example can be illustrated in a small shape like the pressure sensors 87 illustrated in FIGS. 2 and 3. In the fifth modification example, the preliminary movement/command input movement determining unit 8h or the receiving unit 8f receives, as a detection result indicating a third contact, a detection result indicating an amount of change in a third capacitance which is a third threshold TH3 or larger from a plurality of touch sensors (not illustrated). Also, if the preliminary movement/command input movement determining unit 8h or the command determination controller 88 receives, as a detection result indicating a second contact and an intermediate contact, a detection result indicating an amount of change in a fourth capacitance which is a fourth threshold TH4 or larger from the touch sensors a certain number of times within the second time period t2 after the preliminary movement/command input movement determining unit 8h or the receiving unit 8f has received a detection result indicating a third contact, the preliminary movement/command input movement determining unit 8h or the command determination controller 88 performs control to increase or decrease the driving power of expansion/contraction driving of the assisting actuators 6.

With this configuration, touch sensors are used as contact sensors, an amount of change in the third capacitance which is the third threshold TH3 or larger is detected as a third contact, and an amount of change in the fourth capacitance which is the fourth threshold TH4 or larger is detected as a second contact and an intermediate contact. Here, in the case of increasing or decreasing the driving power of expansion/contraction driving of the assisting actuators 6, the user 1 is likely to touch the wear main body 2 more strongly than in the case of touching it accidentally. Thus, for example, if the third threshold TH3 and the fourth threshold TH4 are set to values that are equal to or larger than an amount of change in capacitance that is detected when the user 1 accidentally touches the wear main body 2, an increase or decrease in the driving power can be prevented when the user 1 accidentally touches the wear main body 2.

Sixth Modification Example

A simultaneous input receiving unit 8g may further be provided in the controller 8, and a simultaneous input mode may be provided so that the assist power for the left leg is automatically adjusted when the assist power for the right leg is adjusted through an assist power adjustment operation performed on the right leg.

That is, the assist wear item 4 includes a pair of attachments 20*a* and 20*b* that are worn on two symmetrical portions of the user 1. In the assist wear item 4, the individual assisting actuators 6 arranged in the attachment 20*a* (one of the symmetrical portions of the user 1) are associated with the individual assisting actuators 6 arranged in the attachment 20*b* (the other of the symmetrical portions of the user 1). The correspondence is stored in, for example, the storage unit 8*a*.

The controller 8 may include the simultaneous input receiving unit 8*g* whose function is turned on when a simultaneous input mode is selected by using the input/output device 16 in the operation device 18 and which performs a simultaneous input control operation. The simultaneous input control operation of the simultaneous input receiving unit 8*g* is enabled when the simultaneous input mode is selected by using the input/output device 16 in the operation device 18. In the simultaneous input control operation, the determining unit 8*c* is operated so that, when control is performed to increase or decrease the driving power of expansion/contraction driving of first assisting actuators 6 arranged in the attachment 20*a* (one of the symmetrical portions of the user 1), control is performed to increase or decrease the driving power of expansion/contraction driving of second assisting actuators 6 arranged in the attachment 20*b* (the other of the symmetrical portions of the user 1).

When a second contact and an intermediate contact are detected by third pressure sensors 87 that are arranged in the region corresponding to the attachment 20*a* (one of the symmetrical portions) after the simultaneous input receiving unit 8*g* has received a simultaneous input reception operation and when the determining unit 8*c* controls an increase or decrease in the driving power of expansion/contraction driving of the first assisting actuators 6 corresponding to the third pressure sensors 87, the determining unit 8*c* controls an increase or decrease in the driving power of expansion/contraction driving of the second assisting actuators 6 corresponding to the first assisting actuators 6 in the attachment 20*b* (the other of the symmetrical portions).

Figure 38:
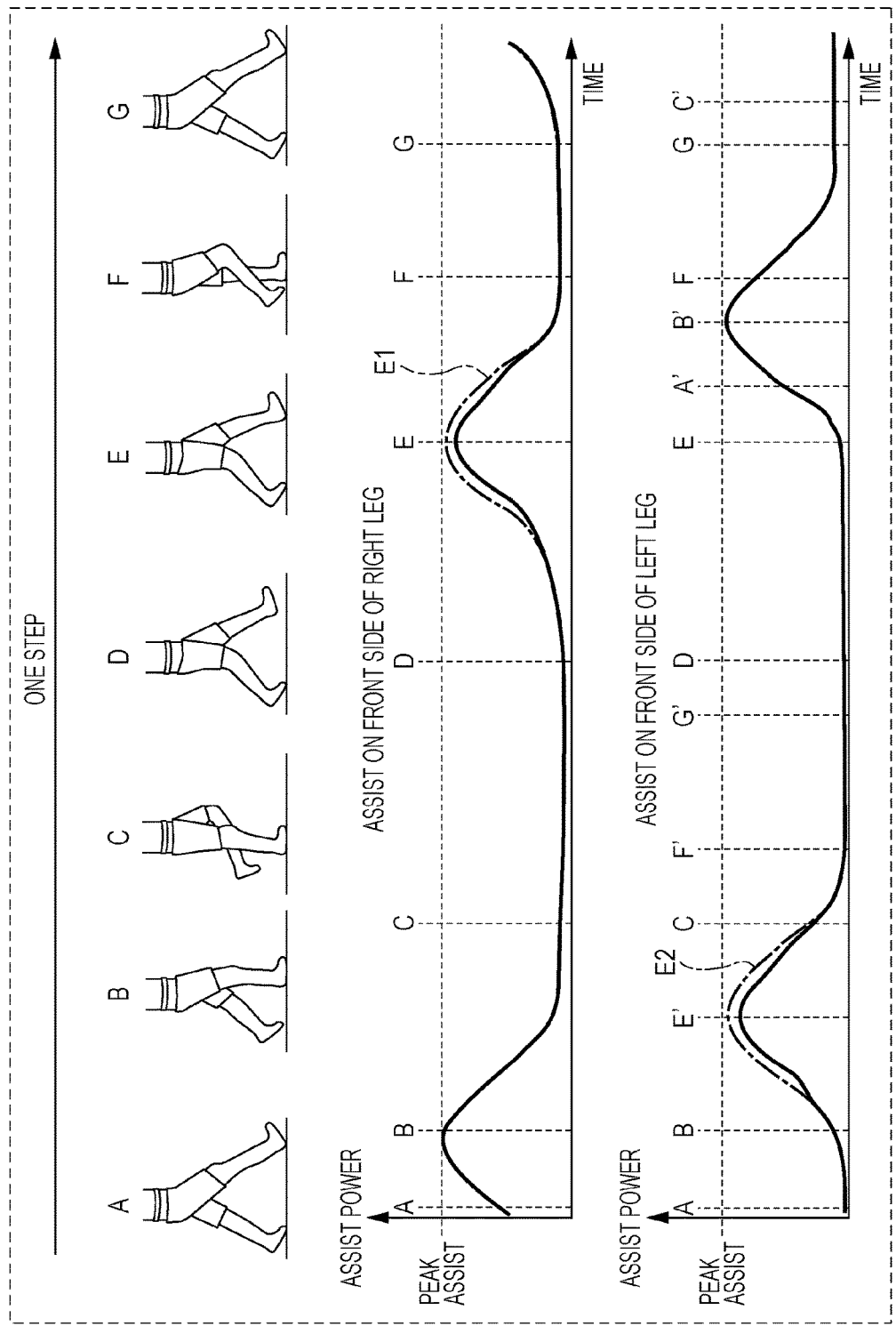
FIG. 38 is an explanatory diagram of a process of assisted walking using assist on the front side of a right leg and a left leg.

For example, in response to an assist power adjustment input for the assisting actuators 6 of one of the right and left legs, an assist power adjustment output for the assisting actuators 6 of the other leg is automatically generated, the generated output is transmitted to the corresponding assisting actuators 6, and an increase or decrease in the driving power of expansion/contraction driving of the assisting actuators 6 is controlled similarly. A specific example is illustrated in FIG. 38. FIG. 38 illustrates a process of assisted walking (phases A' to G') on the front side of the left leg corresponding to a process of assisted walking (phases A to G) on the front side of the right leg using the assist wear item 4 illustrated in FIG. 25. As illustrated in FIG. 38, the assist power reaches a peak in phase B in the process of assisted walking (phases A to G) on the front side of the right leg using the assist wear item 4, but the assist power is not at the peak in phase E. At this time, it is assumed that a preliminary movement and a command input movement are performed to increase the assist power in phase E to the peak, and control is performed to increase the assist power in phase E to the peak (see the chained line E1 in FIG. 38). With such control being performed, the determining unit 8*c* performs control to increase the assist power in phase E' on the front side of the left leg, corresponding to phase E on the front side of the right leg, to the peak, in response to an instruction provided from the simultaneous input receiving unit 8*g* (see the chained line E2 in FIG. 38).

With this configuration, in a case where assist pants that are worn to cover both legs are used as the assist wear item 4, if the driving power for one of the legs is increased or decreased, the driving power for the other leg is also increased or decreased. Accordingly, if an input is given for one of the legs, an input can also be given for the other leg simultaneously, and thus an input operation can be performed more easily.

Seventh Modification Example

Figure 39:
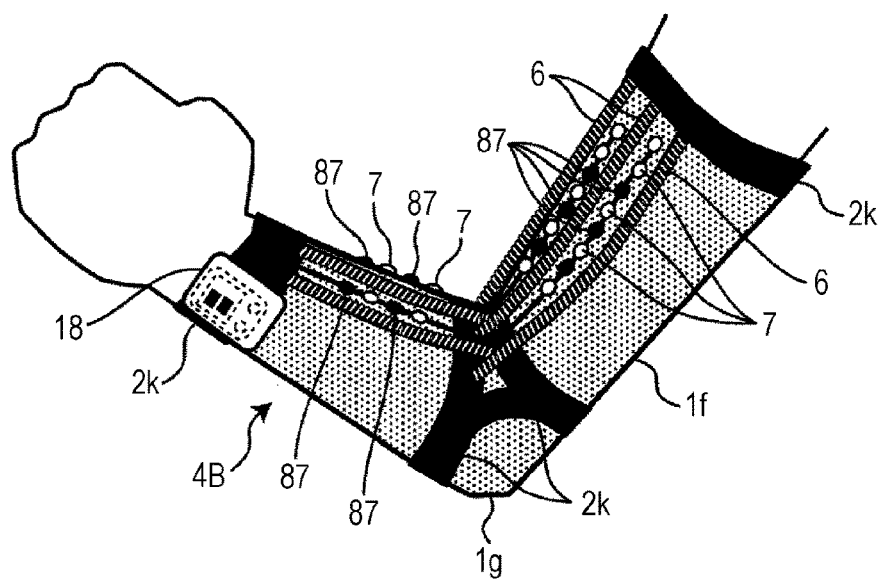
FIG. 39 is an explanatory diagram of an assist wear item for an elbow according to a seventh modification example.
Figure 40:
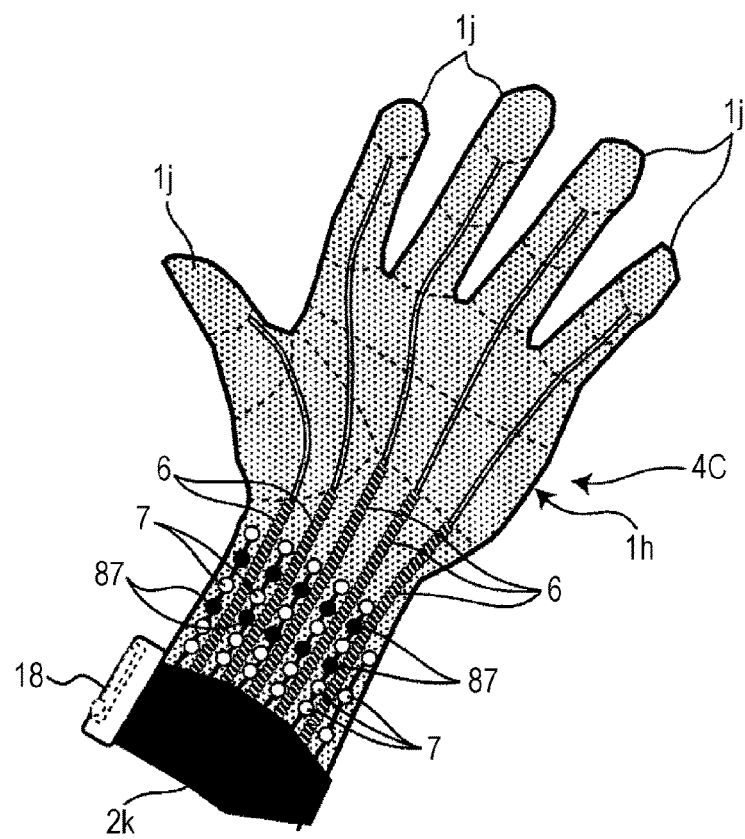
FIG. 40 is an explanatory diagram of an assist wear item for fingers according to the seventh modification example.

In the above-described embodiment, pants are used as an example of the wear main body 2, but the wear main body 2 is not limited thereto. As illustrated in FIGS. 39 and 40, an assist wear item 4B for an elbow that is worn on an arm if and assists bending and stretching movements of an elbow 1*g*, or an assist wear item 4C for fingers that is worn on a hand 1*h* and assists bending and stretching movements of fingers 1*j*, may be used. Also, the controller belt 3 is not limited to the one provided separately from the wear main body 2 as illustrated in FIG. 2. As illustrated in FIG. 39, the operation device 18 may be provided at an end portion of a wear main body 2B of the assist wear item 4B for an elbow.

As illustrated in FIG. 39, the assist wear item 4B for an elbow includes a plurality of assisting actuators 6 arranged along an axis direction of the arm 1*f*.

As illustrated in FIG. 40, the assist wear item 4C for fingers includes a plurality of assisting actuators 6 arranged along an axis direction of the arm if and the fingers 1*j*.

In FIGS. 39 and 40, black band portions are restraining portions 2*k* such as rubber belts.

Other than these examples, an assist wear item may also be applied to a knee, an ankle, toes, and so forth.

The present disclosure has been described on the basis of the embodiment and modifications. The present disclosure is of course not limited to the embodiment and modifications. The following is also included in the present disclosure.

Part of the controller 8 or the entire controller 8 is specifically a computer system constituted by a microprocessor, a read only memory (ROM), a random access memory (RAM), a hard disk unit, a display unit, a keyboard, a mouse, and so forth. The RAM or the hard disk unit stores a computer program. When the microprocessor operates in accordance with the computer program, the individual units implement their functions. Here, the computer program is constituted by combining a plurality of command codes indicating instructions for the computer to implement certain functions.

For example, a software program recorded on a recording medium such as a hard disk or a semiconductor memory is read and executed by a program executing unit such as a central processing unit (CPU), and thereby the individual components can be implemented.

The software that implements some or all of the components constituting the controller according to the embodiment or modification examples is the following program. That is, the program is executed by the controller of an assist wear item that is worn on a portion of a living body and that has an inner surface which is brought into contact with the portion, the assist wear item including a plurality of assisting actuators each of which is driven to expand and contract, the plurality of assisting actuators being linearly arranged along an expansion/contraction direction of a muscle at the portion in a case where the assist wear item is worn on the portion, a plurality of contact sensors each of which detects a contact with an outer surface of the assist wear item, and the controller, the program including:

receiving a detection result indicating a first contact from a first contact sensor among the plurality of contact sensors; and if a detection result indicating a contact is continuously received from a contact sensor arranged between the first contact sensor and a second contact sensor that is arranged at a certain distance or more from the first contact sensor during a time period after the receiving until a detection result indicating a second contact is received from the second contact sensor, increasing or decreasing a driving power of expansion/contraction driving of an assisting actuator corresponding to a region ranging from the first contact sensor to the second contact sensor among the plurality of assisting actuators.

This program may be executed after being downloaded from a server or the like, or may be executed after being read out from a certain recording medium (for example, an optical disc such as a CD-ROM, a magnetic disk, or a semiconductor memory).

The program may be executed by a single computer or a plurality of computers. That is, centralized processing may be performed or distributed processing may be performed.

Among the above-described various embodiments and modification examples, certain embodiments or certain modification examples may be appropriately combined so as to obtain respective effects. A combination of embodiments, a combination of modification examples, and a combination of an embodiment and a modification example are acceptable, and also a combination of features of different embodiments or modification examples is acceptable.

An assist wear item, a method for controlling a controller of an assist wear item, and a recording medium according to an embodiment of the present disclosure are capable of easily adjusting an increase or decrease in the driving power of expansion/contraction driving of assisting actuators in the case of assisting movements of a living body. Thus, the assist wear item, the method for controlling a controller of an assist wear item, and the recording medium according to the embodiment of the present disclosure can be used to adjust the assist power for various assist operations for assisting movements, such as an assist operation for lifting or carrying a heavy object, in which biceps brachii, back muscles, gluteus maximus, or femoral muscles are assisted to reduce heavy burden; a gripping power assist operation for assisting bending and stretching of fingers or a walking assist operation for assisting gluteus maximus or femoral muscles for rehabilitation or assist of reduced muscular power; an assist operation for muscles of the neck, shoulders, or back for massage; a muscle assist operation for a golf swing lesson or the like, in which muscles of the whole body are assisted for skill assist; and a muscle assist operation for developing muscles by imposing a load in the opposite direction of movements of the muscles for training.

What is claimed is:

1. An assist wear item configured to be worn on a portion of a living body and that has an inner surface which is brought into contact with the portion, comprising:

a plurality of assisting actuators each being configured to be driven to expand and contract, the plurality of assisting actuators being linearly arranged along an expansion or contraction direction of a muscle at the portion in a case where the assist wear item is worn on the portion;

a plurality of contact sensors each being configured to detect a contact with an outer surface of the assist wear item, the plurality of contact sensors including a first contact sensor and two or more other contact sensors, the two or more other contact sensors including a second contact sensor and at least one of the two or more other contact sensors except for the second contact sensor being arranged between the first contact sensor and the second contact sensor; and a controller that increases or decreases a driving power for expanding or contracting of a first assisting actuator corresponding to a region ranging from the first contact sensor to the second contact sensor when the controller receives at least one detection result indicating at least one contact from the two or more other contact sensors during a time period after the controller determines that the controller receives a detection result indicating a first contact from the first contact sensor, wherein the controller determines that the controller receives the detection result indicating the first contact from the first contact sensor when conditions including a first condition and a second condition are satisfied, the first condition is satisfied when the controller receives a detection result indicating a contact with the outer surface of the assist wear item from the first contact sensor during expansion or contraction driving of the first assisting actuator, and the controller increases or decreases the driving power for expanding or contracting a range of the first assisting actuator corresponding to the region ranging from the first contact sensor to the second contact sensor to assist movement of the portion corresponding to the region.

2. The assist wear item according to claim 1, wherein the two or more other contact sensors includes a third contact sensor, and the second condition is satisfied when the controller receives a detection result indicating a contact with the outer surface of the assist wear item from the first contact sensor within a first time period after the controller receives a detection result indicating a third contact from the third contact sensor.

3. The assist wear item according to claim 2, wherein the third contact sensor is identical to the first contact sensor.

4. The assist wear item according to claim 1, wherein the controller increases the driving power of the expansion or contraction driving of the first assisting actuator as the distance between the first contact sensor and the second contact sensor increases.

5. The assist wear item according to claim 1, wherein, when the controller receives a detection result indicating a contact with the outer surface of the assist wear item from the first contact sensor during expansion driving of the first assisting actuator, the controller increases a driving power of the expansion driving of the first assisting actuator.

6. The assist wear item according to claim 1, wherein, when the controller receives a detection result indicating a contact with the outer surface of the assist wear item from the first contact sensor during contraction driving of the first assisting actuator, the controller increases a driving power of the contraction driving of the first assisting actuator.

7. The assist wear item according to claim 1, wherein an increase or decrease in the driving power of the expansion or contraction driving of the first assisting actuator is controlled by changing an expansion or contraction range of the first assisting actuator.

8. The assist wear item according to claim 1, wherein a spring constant of the first assisting actuator is controlled based on an increase or decrease in the driving power of the first assisting actuator.

9. The assist wear item according to claim 1, wherein
the plurality of contact sensors are a plurality of pressure sensors each of which detects a pressure value of a pressure applied to the outer surface of the assist wear item, and
when the controller receives a detection result indicating a pressure value which is a first threshold or larger from each of the plurality of pressure sensors, the controller determines that there has been a contact with the outer surface of the assist wear item.

10. The assist wear item according to claim 1, further comprising:
a plurality of myoelectric sensors each of which detects a voltage value of a voltage generated when the muscle at the portion is moved, the plurality of myoelectric sensors being arranged at positions where the plurality of assisting actuators are arranged or around the positions,
wherein the controller causes the plurality of assisting actuators to be driven to expand and contract in accordance with the individual voltage values detected by the plurality of myoelectric sensors.

11. The assist wear item according to claim 10, wherein, when an amount of change in the voltage value per unit time detected by a first myoelectric sensor among the plurality of myoelectric sensors is equal to or larger than a second threshold, the controller increases a first threshold that is used by a pressure sensor corresponding to the first myoelectric sensor to detect a pressure value.

12. The assist wear item according to claim 1, wherein
the plurality of contact sensors are a plurality of touch sensors each of which detects an amount of change in capacitance, the plurality of touch sensors being arranged on the outer surface of the assist wear item, and
when the controller receives a detection result indicating an amount of change in capacitance that is equal to or larger than a third threshold from each of the plurality of touch sensors, the controller determines that there has been a contact with the outer surface of the assist wear item.

13. The assist wear item according to claim 1, wherein
the assist wear item includes a pair of attachments that are configured to be respectively worn on two symmetrical portions of the living body,
each of the plurality of assisting actuators arranged on a first attachment in the pair of attachments is associated with a corresponding one of the plurality of assisting actuators arranged on a second attachment in the pair of attachments, and
when a driving power of expansion or contraction driving of the first assisting actuator arranged on the first attachment is increased, the controller increases together with the increase in the first assisting actuator, a driving power of expansion or contraction driving of a second assisting actuator arranged on the second attachment and corresponding to the first assisting actuator.

14. A control method for a controller of an assist wear item configured to be worn on a portion of a living body and that has an inner surface which is brought into contact with the portion, the assist wear item including
a plurality of assisting actuators each being configured to be driven to expand and contract, the plurality of assisting actuators being linearly arranged along an expansion or contraction direction of a muscle at the portion in a case where the assist wear item is worn on the portion,
a plurality of contact sensors each being configured to detect a contact with an outer surface of the assist wear item, the plurality of contact sensors including a first contact sensor and two or more other contact sensors, the two or more other contact sensors including a second contact sensor and at least one of the two or more other contact sensors except for the second contact sensor being arranged between the first contact sensor and the second contact sensor, and
the controller,
the control method comprising:
increasing or decreasing a driving power for expanding or contracting of an assisting actuator corresponding to a region ranging from the first contact sensor to the second contact sensor when the controller receives at least one detection result indicating at least one contact from the two or more other contact sensors during a time period after the controller determines that the controller receives a detection result indicating a first contact from the first contact sensor,
wherein the controller determines that the controller receives a detection result indicating a first contact from the first contact sensor when conditions including a first condition and a second condition are satisfied,
the first condition is satisfied when the controller receives a detection result indicating a contact with the outer surface of the assist wear item from the first contact sensor during expansion or contraction driving of the assisting actuator, and
the controller increases or decreases the driving power for expanding or contracting a range of the assisting actuator corresponding to the region ranging from the first contact sensor to the second contact sensor to assist movement of the portion corresponding to the region.

15. A non-transitory computer readable storage medium storing a program that causes a device including a processor to perform processing executed by a controller of an assist wear item configured to be worn on a portion of a living body and that has an inner surface which is brought into contact with the portion,
the recording medium being nonvolatile and computer-readable,
the assist wear item including
a plurality of assisting actuators each of which is driven to expand and contract, the plurality of assisting actuators being linearly arranged along an expansion or contraction direction of a muscle at the portion in a case where the assist wear item is worn on the portion,
a plurality of contact sensors each being configured to detect a contact with an outer surface of the assist wear item, the plurality of contact sensors including a first contact sensor and two or more other contact sensors, the two or more other contact sensors including a second contact sensor and at least one of the two or more other contact sensors except for the second contact sensor being arranged between the first contact sensor and the second contact sensor, and the controller, the processing performed by the controller comprising:

increasing or decreasing a driving power for expanding or contracting of an assisting actuator corresponding to a region ranging from the first contact sensor to the second contact sensor when the controller receives at least one detection result indicating at least one contact from the two or more other contact sensors during a time period after the controller determines that the controller receives a detection result indicating a first contact from the first contact sensor, wherein the controller determines that the controller receives a detection result indicating a first contact from the first contact sensor when conditions including a first condition and a second condition are satisfied, the first condition is satisfied when the controller receives a detection result indicating a contact with the outer surface of the assist wear item from the first contact sensor during expansion or contraction driving of the assisting actuator, and the controller increases or decreases the driving power for expanding or contracting a range of the assisting actuator corresponding to the region ranging from the first contact sensor to the second contact sensor to assist movement of the portion corresponding to the region.

16. The assist wear item according to claim 1, further comprising:

a sensor that detects a posture of the portion, wherein, based on an output from the sensor, the controller selects the first contact sensor in accordance with the posture detected by the sensor, and detects the first contact based on an output from the selected first contact sensor.

17. The assist wear item according to claim 16, further comprising:

a myoelectric sensor, wherein the posture of the portion is detected based on a waveform of a voltage detected by the myoelectric sensor, and the plurality of assisting actuators are caused to periodically expand and contract.

18. An assist wear item configured to be worn on a portion of a living body and that has an inner surface which is brought into contact with the portion, the assist wear item comprising:

a first sensor that detects a first contact with the assist wear item and outputs a first signal;

a second sensor that detects a second contact with the assist wear item and outputs a second signal;

a third sensor that detects a third contact with the assist wear item and outputs a third signal;

an actuator that changes a degree of contraction in a contraction direction of a muscle at the portion, in response to a control signal including information indicating the degree of contraction; and a controller that receives the first signal, the second signal, and the third signal, and outputs the control signal, the controller generating the control signal when the controller receives the first signal after the controller receives an instruction to start driving the actuator, the controller receives the second signal after the controller receives the first signal, and the controller receives the third signal after the controller receives the second signal, wherein the controller determines the information in a manner that the degree of contraction of the actuator increases as a sum of a first distance between the first sensor and the second sensor and a second distance between the second sensor and the third sensor increases, and the controller controls the degree of contraction of the actuator based on the information to assist movement of portion.

* * * * *